US011707590B2

United States Patent
Eves et al.

(10) Patent No.: US 11,707,590 B2
(45) Date of Patent: Jul. 25, 2023

(54) PATIENT INTERFACE WITH A SEAL-FORMING STRUCTURE HAVING VARYING THICKNESS

(71) Applicant: ResMed Pty Ltd, Bella Vista (AU)

(72) Inventors: Matthew Eves, Sydney (AU); Lemmy Nga, Sydney (AU); Gerard Michael Rummery, Woodford (AU); Rupert Christian Scheiner, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 283 days.

(21) Appl. No.: 17/002,244

(22) Filed: Aug. 25, 2020

(65) Prior Publication Data
US 2020/0384230 A1    Dec. 10, 2020

Related U.S. Application Data

(63) Continuation of application No. 15/759,985, filed as application No. PCT/AU2016/050896 on Sep. 23, 2016, now Pat. No. 10,799,661.
(Continued)

(30) Foreign Application Priority Data

Mar. 24, 2016   (WO) ................ PCT/AU2016/050228

(51) Int. Cl.
*A61M 16/06*    (2006.01)
*A61M 16/00*    (2006.01)
(Continued)

(52) U.S. Cl.
CPC .... *A61M 16/0622* (2014.02); *A61M 16/0066* (2013.01); *A61M 16/0616* (2014.02);
(Continued)

(58) Field of Classification Search
CPC .............. A61M 16/06; A61M 16/0605; A61M 16/0611; A61M 16/0616; A61M 16/0622; A61M 2016/0661
See application file for complete search history.

(56) References Cited

U.S. PATENT DOCUMENTS

| | | |
|---|---|---|
| 4,782,832 A | 11/1988 | Trimble et al. |
| 4,907,584 A | 3/1990 | McGinnis et al. |

(Continued)

FOREIGN PATENT DOCUMENTS

| | | |
|---|---|---|
| CN | 101198379 A | 6/2008 |
| CN | 101242866 A | 8/2008 |

(Continued)

OTHER PUBLICATIONS

Extended European Search Report dated Jul. 18, 2022 issued in European Application No. 22150043.2 (9 pages).
(Continued)

*Primary Examiner* — Joseph D. Boecker
(74) *Attorney, Agent, or Firm* — Nixon & Vanderhye P.C.

(57) ABSTRACT

A cushion assembly for a patient interface includes an elastomeric seal-forming portion with a dome-shaped superior region that is intersected by the sagittal plane in the vicinity of a superior tangent point. The seal-forming portion further including a saddle-shaped inferior region that is intersected by the sagittal plane and includes an inferior tangent point. A first support region is located on one side of the sagittal plane between the inferior region and the superior region, the exterior surface of the elastomeric seal forming portion at the first support region being cylinder-shaped and/or saddle-shaped. In addition, a blowout prevention system is configured to counter a force acting on the unsupported edge of the elastomeric seal-forming portion due to a pressure within the chamber, the blowout prevention system being attached to the elastomeric seal-forming por-
(Continued)

tion at the first support region of the elastomeric seal-forming portion.

28 Claims, 78 Drawing Sheets

Related U.S. Application Data

(60) Provisional application No. 62/377,217, filed on Aug. 19, 2016, provisional application No. 62/222,503, filed on Sep. 23, 2015.

(51) Int. Cl.
    *A61M 16/08*     (2006.01)
    *A61M 16/16*     (2006.01)

(52) U.S. Cl.
    CPC .... *A61M 16/0633* (2014.02); *A61M 16/0666* (2013.01); *A61M 16/0683* (2013.01); *A61M 16/16* (2013.01); *A61M 16/0069* (2014.02); *A61M 16/06* (2013.01); *A61M 16/0875* (2013.01); *A61M 2205/3344* (2013.01); *A61M 2210/0618* (2013.01); *A61M 2210/0625* (2013.01)

(56) References Cited

U.S. PATENT DOCUMENTS

| | | | |
|---|---|---|---|
| 4,907,854 A | 3/1990 | McGinnis | |
| 4,944,310 A | 7/1990 | Sullivan | |
| 6,467,483 B1 | 10/2002 | Kopacko et al. | |
| 6,532,959 B1 | 3/2003 | Berthon-Jones | |
| 6,581,594 B1 | 6/2003 | Drew et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 10,188,820 B2 | 1/2019 | Edwards | |
| 10,926,050 B2 | 2/2021 | Eves et al. | |
| 11,052,210 B2 * | 7/2021 | Eves | A61M 16/0666 |
| 2001/0020474 A1 | 9/2001 | Hecker et al. | |
| 2003/0019496 A1 | 1/2003 | Kopacko | |
| 2003/0196656 A1 | 10/2003 | Moore et al. | |
| 2004/0118406 A1 * | 6/2004 | Lithgow | A61M 16/08 128/206.26 |
| 2006/0096598 A1 | 5/2006 | Ho | |
| 2006/0130844 A1 | 6/2006 | Ho et al. | |
| 2007/0267017 A1 | 11/2007 | McAuley et al. | |
| 2008/0006277 A1 * | 1/2008 | Worboys | A61M 16/0605 128/207.13 |
| 2008/0110464 A1 * | 5/2008 | Davidson | A61M 16/06 128/206.26 |
| 2008/0302366 A1 | 12/2008 | McGinnis et al. | |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0006101 A1 | 1/2010 | McCauley | |
| 2010/0170516 A1 | 7/2010 | Grane | |
| 2012/0067349 A1 | 3/2012 | Barlow | |
| 2012/0080035 A1 | 4/2012 | Guney | |
| 2012/0138062 A1 | 6/2012 | Ho et al. | |
| 2012/0222680 A1 | 9/2012 | Eves et al. | |
| 2012/0285464 A1 | 11/2012 | Birch et al. | |
| 2013/0139822 A1 | 6/2013 | Gibson et al. | |
| 2013/0146060 A1 | 6/2013 | Ho | |
| 2013/0199537 A1 | 8/2013 | Formica et al. | |
| 2013/0340763 A1 | 12/2013 | Eifler et al. | |
| 2014/0144448 A1 | 5/2014 | Eifler | |
| 2014/0174446 A1 * | 6/2014 | Prentice | A61M 16/0633 128/205.25 |
| 2014/0216462 A1 | 8/2014 | Law et al. | |
| 2014/0326243 A1 * | 11/2014 | Znamenskiy | A61M 16/0633 128/205.25 |
| 2014/0326246 A1 | 11/2014 | Chodkowski et al. | |
| 2014/0366886 A1 * | 12/2014 | Chodkowski | A61M 16/06 128/206.24 |
| 2015/0040911 A1 * | 2/2015 | Davidson | A61M 16/06 128/206.24 |
| 2015/0090266 A1 | 4/2015 | Melidis | |
| 2015/0144140 A1 | 5/2015 | Eury | |
| 2015/0151067 A1 | 6/2015 | Eury | |
| 2015/0246198 A1 | 9/2015 | Bearne et al. | |
| 2015/0250971 A1 | 9/2015 | Bachelder et al. | |
| 2015/0328423 A1 | 11/2015 | Siew | |
| 2015/0335845 A1 | 11/2015 | Baiko | |
| 2015/0352306 A1 | 12/2015 | Scheiner | |
| 2016/0082213 A1 | 3/2016 | Eifler | |
| 2016/0339196 A1 * | 11/2016 | Bowsher | A61M 16/0622 |
| 2018/0185598 A1 * | 7/2018 | Olsen | A61M 16/0825 |
| 2018/0272094 A1 | 9/2018 | Eves et al. | |
| 2018/0272095 A1 | 9/2018 | Eves | |
| 2018/0280649 A1 | 10/2018 | Eves | |
| 2019/0151590 A1 | 5/2019 | Guney et al. | |
| 2020/0121880 A1 | 4/2020 | Olsen et al. | |
| 2020/0246571 A1 | 8/2020 | Prentice et al. | |

FOREIGN PATENT DOCUMENTS

| | | |
|---|---|---|
| CN | 101301505 A | 11/2008 |
| CN | 103945890 A | 7/2014 |
| CN | 104587580 A | 5/2015 |
| EP | 1258266 A1 | 11/2002 |
| EP | 1982740 A2 | 10/2008 |
| EP | 3095478 A1 | 11/2016 |
| JP | 2008-518718 A | 6/2008 |
| JP | 2009-195758 A | 9/2009 |
| JP | 2012-530561 | 12/2012 |
| JP | 2014-517735 | 7/2014 |
| JP | 2014-520587 | 8/2014 |
| JP | 2015-126945 | 7/2015 |
| JP | 2016-504940 | 2/2016 |
| JP | 2017-527365 | 9/2017 |
| JP | 2018-527155 | 9/2018 |
| JP | 2018-527156 | 9/2018 |
| WO | 98/04310 | 2/1998 |
| WO | 98/34665 | 8/1998 |
| WO | 00/78381 | 12/2000 |
| WO | 2004/073778 | 9/2004 |
| WO | 2005/063328 | 7/2005 |
| WO | 2006/074513 | 7/2006 |
| WO | 2006/130903 | 12/2006 |
| WO | 2007/009182 A1 | 1/2007 |
| WO | 2009/052560 | 4/2009 |
| WO | 2010/009877 A1 | 1/2010 |
| WO | 2010/135785 | 12/2010 |
| WO | 2010/148453 A | 12/2010 |
| WO | 2012/140514 A1 | 10/2012 |
| WO | 2012/171072 A1 | 12/2012 |
| WO | 2013/020167 A1 | 2/2013 |
| WO | 2014/038959 A1 | 3/2014 |
| WO | 2014/062070 A1 | 4/2014 |
| WO | 2014/091360 A1 | 6/2014 |
| WO | 2014/110626 A1 | 7/2014 |
| WO | 2014/117227 A1 | 7/2014 |
| WO | 2014/117227 A9 | 8/2014 |
| WO | 2014/141029 A1 | 9/2014 |
| WO | 2014/155329 A2 | 10/2014 |
| WO | 2015/009172 A1 | 1/2015 |
| WO | 2015/063283 A1 | 5/2015 |
| WO | 2016/032343 A1 | 3/2016 |
| WO | 2016/041019 A1 | 3/2016 |
| WO | 2016/097948 | 6/2016 |
| WO | 2016/103138 A1 | 6/2016 |
| WO | 2017/049361 A1 | 3/2017 |

OTHER PUBLICATIONS

Office Action dated Sep. 5, 2022 issued in Japanese Application No. 2021-133423 with English translation (16 pages).
Office Action dated Dec. 8, 2020 issued in Chinese Application No. 201680066661.1 with English translation (11 pages).

(56) References Cited

OTHER PUBLICATIONS

Office Action dated Feb. 3, 2020 issued in Chinese Application No. 201680056156.9 with English translation (15 pages).
Office Action dated Feb. 3, 2020 issued in Chinese Application No. 201680061003.3 with English translation (21 pages).
Office Action dated Nov. 27, 2019 issued in U.S. Appl. No. 15/762,150 (17 pages).
Office Action dated Feb. 25, 2020 issued in U.S. Appl. No. 15/761,168 (22 pages).
Extended European Search Report dated Aug. 14, 2019 issued in European Application No. 16847659.6 (13 pages).
Extended European Search Report dated May 10, 2019 issued in European Application No. 16847657.0 (8 pages).
International Search Report for PCT/AU2016/050894, dated Dec. 12, 2016, 7 pages.
Written Opinion of the ISA for PCT/AU2016/050894, dated Dec. 12, 2016, 4 pages.
Written Opinion of the IPEA for PCT/AU2016/050894, dated Oct. 27, 2017, 6 pages.
International Preliminary Report on Patentability for PCT/AU2016/050894, dated Jan. 16, 2018, 11 pages.
International Search Report for PCT/AU2016/050895, dated Jan. 12, 2017, 15 pages.
Written Opinion of the Isa PCT/AU2016/050895, dated Jan. 12, 2017, 12 pages.
Written Opinion of the IPEA for PCT/AU2016/050895, dated Oct. 23, 2017, 10 pages.
International Preliminary Report on Patentability for PCT/AU2016/050895, dated Jan. 22, 2018, 221 pages.
Extended European Search Report dated May 13, 2019 issued in European Application No. 16847658.8 (11 pages).
Partial Supplementary European Search Report dated May 13, 2019 issued in European Application No. 16847659.6 (15 pages).
International Search Report for PCT/AU2016/050896, dated Jan. 3, 2017, 9 pages.
Written Opinion for PCT/AU2016/050896, dated Jan. 3, 2017, 7 pages.
International Preliminary Report on Patentability for PCT/AU2016/050896, dated Jan. 9, 2018, 189 pages.
West, John, "Respiratory Physiology", Lippincott Williams & Wilkins, 9$^{th}$ edition, pub. 2012.

Office Action dated Oct. 15, 2020 issued in European Application No. 16847657.0 (5 pages).
Notice of Reasons for Rejection dated Oct. 12, 2020 issued in Application No. 2018-533977 with English translation (15 pages).
Office Action dated Apr. 28, 2021 issued in Chinese Application No. 201680066661.1 with English translation (16 pages).
Office Action dated Jun. 28, 2021 issued in Japanese Application No. 2018-533976 with English translation (6 pages).
Notice of Allowance dated Jun. 21, 2021 issued in Japanese Application No. 2018-533977 (3 pages).
Notice of Allowance dated Jul. 19, 2021 issued in Japanese Application No. 2018-533978 (3 pages).
Office Action dated Oct. 5, 2020 issued in Japanese Application No. 2018-533976 with English translation (8 pages).
Office Action dated Oct. 19, 2020 issued in Japanese Application No. 2018-533978 with English translation (8 pages).
Office Action dated Oct. 26, 2020 issued in European Application No. 16847658.8 (5 pages).
Office Action dated May 9, 2022 issued in Japanese Application No. 2021-119633 with English translation (15 pages).
Examination Report dated Jul. 5, 2022 issued in New Zealand Application No. 740229 (3 pages).
Extended European Search Report dated Jul. 18, 2022 issued in European Application No. 21214534.6 (8 pages).
Examination Report dated Jul. 12, 2022 issued in New Zealand Application No. 769765 (3 pages).
Office Action dated Jan. 12, 2023 issued in U.S. Appl. No. 17/124,578 (29 pages).
Examination Report dated Nov. 25, 2022 issued in New Zealand Application No. 740229 (3 pages).
Extended European Search Report dated Oct. 11, 2022 issued in European Application No. 22176256.0 (10 pages).
Notice of Allowance dated Oct. 24, 2022 issued in Japanese Application No. 2021-119633 (3 pages).
Office Action dated Oct. 3, 2022 issued in Japanese Application No. 20210175495 with English translation (15 pages).
Notice of Allowance dated Apr. 24, 2023 issued in Japanese Application No. 2021-175495 (3 pages).
Examination Report dated May 12, 2023 issued in New Zealand Application No. 778730 (3 pages).
Examination Report dated May 12, 2023 issued in New Zealand Application No. 740770 (3 pages).

* cited by examiner

Relatively Large Positive Curvature

Relatively Small Positive Curvature

Zero Curvature

Relatively Small Negative Curvature

Relatively Large Negative Curvature

Copyright 2015 ResMed Limited

Copyright 2015 ResMed Limited

Left-hand rule           Right-hand rule

FIG. 3O           FIG. 3P

Left ear helix           Right ear helix

FIG. 3Q    Right-hand helix / Right-hand positive    FIG. 3R

Copyright 2015 ResMed Limited

PATIENT INTERFACE WITH A SEAL-FORMING STRUCTURE HAVING VARYING THICKNESS

1 BACKGROUND OF THE TECHNOLOGY

This application is a continuation of U.S. application Ser. No. 15/759,985, filed Mar. 14, 2018, now allowed, which is the U.S. national phase of International Application No. PCT/AU2016/050896 filed Sep. 23, 2016 which designated the U.S. and claims priority U.S. Application No. 62/222,503 filed Sep. 23, 2015, International Application No. PCT/AU2016/050228 filed Mar. 24, 2016 and U.S. Application No. 62/377,217 filed Aug. 19, 2016, the entire contents of each of which are incorporated herein by reference.

1.1 FIELD OF THE TECHNOLOGY

The present technology relates to one or more of the detection, diagnosis, treatment, prevention and amelioration of respiratory-related disorders. The present technology also relates to medical devices or apparatus, and their use.

1.2 DESCRIPTION OF THE RELATED ART

1.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise a first sub-portion to form a seal around the left naris and a second sub-portion to form a seal around the right naris. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

1.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisee™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

1.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

1.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

1.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

1.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |

-continued

| Mask name | Mask type | A-weighted sound power level dB(A) (uncertainty) | A-weighted sound pressure dB(A) (uncertainty) | Year (approx.) |
|---|---|---|---|---|
| ResCare standard (*) | nasal | 31.5 | 23.5 | 1993 |
| ResMed Mirage (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH₂O)Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

1.2.4 Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculography (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home sleep testing.

Clinical experts may be able to diagnose or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One aspect of the present technology is directed to a patient interface that comprises: a plenum chamber pressurisable to a therapeutic pressure of at least 6 cmH2O above ambient air pressure, said plenum chamber including a plenum chamber inlet port, said plenum chamber inlet port being sized and structured to receive a flow of air at the therapeutic pressure for breathing by a patient; a sealing structure constructed and arranged to have a shape to form a seal with a region of the patient's face surrounding an entrance to the patient's airways such that the flow of air at said therapeutic pressure is delivered to at least an entrance to the patient's nares, said seal being formed to prevent air exiting from the plenum chamber between the sealing structure and said region of the patient's face, the sealing structure structured and arranged to maintain said therapeutic pressure in the plenum chamber throughout the patient's respiratory cycle in use; a positioning and stabilising structure to maintain the sealing structure in a therapeutically effective position on the patient's head while the patient is lying in a side sleeping position and while the patient is lying in a supine sleeping position said positioning and stabilising structure including a low-profile side portion and a low-profile rear portion; and a washout vent structure configured to allow a continuous vent flow from an interior of the plenum chamber to ambient whilst the pressure within the plenum chamber is positive with respect to ambient, said vent structure being configured such that the vent flow rate has a magnitude sufficient to help reduce rebreathing of exhaled CO2 by the patient during both patient inhalation and patient exhalation while maintaining the therapeutic pressure in the plenum chamber in use, wherein the sealing structure comprises a sealing surface that forms the seal against the patient's face in use, wherein the sealing structure comprises a tie that extends between a first interior surface region of the sealing structure that is opposite the sealing surface and a second interior surface region of the patient interface such that the tie resists deformation of the sealing structure.

In examples, (a) the sealing structure may comprise the second interior surface region, the second interior surface region being spaced from the first interior surface region, (b) the plenum chamber may comprise the second interior surface region, the second interior surface region being spaced from the first interior surface region, (c) the tie and the sealing structure may comprise a unitary structure formed from a homogeneous material, (d) the homogeneous material may be silicone rubber, (e) the silicone rubber may be liquid silicone rubber or compression molded silicone rubber, (f) the sealing structure may comprises a sealing flap at an edge region, the sealing flap being shaped and positioned to seal at least against a side of the patient's nose in use, and the sealing flap being thinner than adjacent regions of the sealing structure, (g) the first interior surface region may be adjacent to the sealing flap such that the tie is spaced inwardly from the sealing flap, (h) the tie may extend contiguously from the sealing structure at an edge region such that the tie forms an extension of the sealing surface, (i) the tie may comprise an inner surface and the sealing structure may comprise an interior surface, (j) the inner surface of the tie being adjacent to and separated from the interior surface of the sealing structure, (k) the plenum chamber may be constructed from a transparent material, (l) the patient interface may be configured so that no part of the patient interface structure enters the mouth in use, (m) the sealing structure may be configured so as to not extend internally of the patient's airways in use, (n) the sealing structure may be configured so as not to not extend below a mental protuberance region in use, and/or (o) the plenum chamber may be configured so as not to cover the eyes in use.

Another aspect of the present technology is directed to an assembly for a patient interface that comprises: a plenum chamber pressurisable to a therapeutic pressure of at least 6 cmH2O above ambient air pressure, said plenum chamber including a plenum chamber inlet port, said plenum chamber inlet port being sized and structured to receive a flow of air at the therapeutic pressure for breathing by a patient; and a sealing structure constructed and arranged to have a shape to form a seal with a region of the patient's face surrounding an entrance to the patient's airways such that the flow of air at said therapeutic pressure is delivered to at least an entrance to the patient's nares, said seal being formed to prevent air exiting from the plenum chamber between the sealing structure and said region of the patient's face, the sealing structure structured and arranged to maintain said therapeutic pressure in the plenum chamber throughout the patient's respiratory cycle in use; wherein the sealing structure comprises a sealing surface that forms the seal against the patient's face in use, wherein the sealing structure comprises a connecting portion that extends between a first interior surface region of the sealing structure that is opposite the sealing surface and a second interior surface region of the assembly such that the connecting portion resists deformation of the sealing structure.

In examples, (a) the sealing structure may comprise the second interior surface region, the second interior surface region being spaced from the first interior surface region, (b) the plenum chamber may comprise the second interior surface region, the second interior surface region being spaced from the first interior surface region, (c) the connecting portion and the sealing structure may comprise a unitary structure formed from a homogeneous material, (d) the homogeneous material may be silicone rubber, (e) the silicone rubber may liquid silicone rubber or compression molded silicone rubber, (f) the sealing structure may comprise a sealing flap at an edge region, the sealing flap being shaped and positioned to seal at least against a side of the patient's nose in use, and the sealing flap being thinner than adjacent regions of the sealing structure, (g) the first interior surface region may be adjacent to the sealing flap such that the connecting portion is spaced inwardly from the sealing flap, (h) the connecting portion may extend contiguously from the sealing structure at an edge region such that the connecting portion forms an extension of the sealing surface, (i) the connecting portion may comprise an inner surface and the sealing structure may comprise an interior surface, the inner surface of the connecting portion being adjacent to and separated from the interior surface of the sealing structure, (j) the plenum chamber may be constructed from a transparent material, (k) the assembly may be configured so that no part of the assembly enters the mouth in use, (l the sealing structure may be configured so as to not extend internally of the patient's airways in use, (m) the sealing structure may be configured so as not to not extend below a mental protuberance region in use, and/or (n) the plenum chamber is configured so as not to cover the eyes in use.

One form of the present technology comprises a sealing structure to seal against a user's face around the user's airways. The sealing structure includes a flap or membrane that extends inward towards the user's airways and includes an attachment structure that prevents an inner boundary of the flap or membrane from being blown outwards (e.g., folded backwards upon itself) due to internal pressurization.

In examples, the attachment structure may comprise: one or more ribs/ties/connecting portions/connecting structures, a flap that extends from the membrane and folds inwards and attaches to another structure to form a tube or loop, or a tube underlying and attached to the membrane.

Another aspect of one form of the present technology is a sealing structure for a patient interface for sealed delivery of a flow of air at a continuously positive pressure with respect to ambient air pressure to an entrance to the patient's airways including at least entrance of a patient's nares. The patient interface is configured to maintain a therapy pressure in a range of about 3 cmH2O to about 40 cmH2O above ambient air pressure in use, throughout the patient's respiratory cycle, while the patient is sleeping, to ameliorate sleep disordered breathing. The sealing structure comprises: a sealing surface configured to form a seal around a periphery of the entrance to the patient's airways, and a loop that folds the sealing structure inwards of an outer perimeter of the sealing structure to form a substantially tube-shaped structure so that the loop is continuous, the loop comprising a portion of the sealing surface.

In examples, (a) the sealing structure further comprising a sealing flap protruding towards an inner perimeter of the sealing structure, (b) the sealing flap is configured to form a seal against the sides of the nose above the nasal bones of the patient, (c) the sealing flap is configured to avoid sealing against the alar, (d) the portion of the sealing surface has increased flexibility relative to a remaining portion of the loop the portion of the sealing surface comprises a thinner wall section than a remaining portion of the loop, (e) the portion of the sealing surface comprises a thicker wall section than a remaining portion of the loop, (f) the loop is located to contact the side wall of the nose including the alar, (g) the loop provides a continuous surface configured to maintain contact with the sides of the nose, above the nasal bones of the patient, (h) the loop comprises at least one closed end, (i) the loop folds the sealing structure inwards to form a connection point on an inner surface of the sealing structure, (j) the connection point is positioned relative to the sealing surface to provide sufficient tension to the loop to counteract outward blowout of the sealing surface when the therapy pressure is applied to an interior surface of the loop, (k) the loop forms a predetermined angle at the connection point and the predetermined angle determines tension in the loop when the therapy pressure is applied, (l) the connection point is adjustable, (m) the connection point is a releasable connection, (n) the sealing structure further comprising a second connection point (o) the sealing surface comprises a region of reduced friction to reduce adherence with the patient's face, (p) the region of reduced friction is a frosted surface, (q) the region of reduced friction is adapted to allow the sides of the nose of the patient to slide freely against the sealing surface, and/or (r) the loop provides an edgeless sealing surface.

Another aspect of one form of the present technology is a patient interface for sealed delivery of a flow of air at a continuously positive pressure with respect to ambient air pressure to an entrance to the patient's airways including at least entrance of a patient's nares. The patient interface is configured to maintain a therapy pressure in a range of about 3 cmH2O to about 40 cmH2O above ambient air pressure in use, throughout the patient's respiratory cycle, while the patient is sleeping, to ameliorate sleep disordered breathing. The patient interface comprises a sealing structure to seal the patient interface against the patient's face. The sealing structure comprises a sealing surface configured to form a seal around a periphery of the entrance to the patient's airways, and a loop that folds the sealing structure inwards of an outer perimeter of the sealing structure to form a substantially tube-shaped structure so that the loop is continuous, the loop comprising a portion of the sealing surface. The patient interface further comprises a positioning and stabilising structure to maintain the sealing structure in sealing contact with an area surrounding an entrance to the patient's airways while maintaining a therapeutic pressure at the entrance to the patient's airways; a plenum chamber pressurised at a pressure above ambient pressure in use; and a gas washout vent configured to allow a flow of patient exhaled CO2 to an exterior of the patient interface to minimise rebreathing of exhaled CO2 by the patient.

In examples, (a) a sealing flap protrudes towards an inner perimeter of the sealing structure, (b) the sealing flap is configured to form a seal against the sides of the nose above the nasal bones and adjacent the sides of the nose above the maxilla, in the depression adjacent the endocanthion of the patient, (c) the sealing flap is configured to avoid sealing against the alar, (d) the portion of the sealing surface has increased flexibility relative to a remaining portion of the loop, (e) the portion of the sealing surface comprises a thinner wall section than a remaining portion of the loop, (f) the portion of the sealing surface comprises a thicker wall section than a remaining portion of the loop, (g) the sealing surface comprises a region of reduced friction to reduce adherence with the patient's face, (h) the region of reduced friction is a frosted surface, (i) the region of reduced friction is adapted to allow the sides of the nose of the patient to slide freely against the sealing surface, (j) the first loop defines an area of the sealing structure adapted to contact the patient's face, (k) the first portion and the second portion are part of the area of the sealing structure adapted to contact the patient's face, (l) the first loop is continuous, (m) the second loop is located to contact or be alongside the patient's nose, (n) the second loop is located so that the substantially tube-shaped structure is adapted to contact or be located alongside the patient's nose, (o) the substantially tube-shaped structure is adapted to be located substantially parallel to a side of the patient's nose, (p) the sealing structure further comprises a second one of the second loop, (q) the substantially tube-shaped structure comprises a hollow interior that is adapted to be in fluid communication with the pressure above ambient pressure, (r) the substantially tube-shaped structure comprises two open ends, and/or (s) the second loop is adapted to prevent the second loop from a blowout when the patient interface is internally pressurized and adjusted by the patient.

Another aspect of one form of the present technology is a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 3 cmH2O to about 40 cmH2O above ambient air pressure in use, throughout the patient's respiratory cycle, while the patient is sleeping, to ameliorate sleep disordered breathing. The patient interface comprises a sealing structure to seal the patient interface against the patient's face. The sealing structure comprises a face contacting portion adapted to contact around a periphery of the entrance to the patient's airways, and at least a first substantially cylindrical region that has an uninterrupted circumference, wherein a portion of the cylindrical region comprises a portion of the face contacting portion. The patient interface further comprises a positioning and stabilising structure to maintain the sealing structure in sealing contact with an area surrounding an entrance to the patient's airways while maintaining a therapeutic pressure at the entrance to the patient's airways; a plenum chamber pressurised at a pressure above ambient pressure in use; and a gas washout vent configured to allow a flow of patient exhaled CO2 to an exterior of the patient interface to minimise rebreathing of exhaled CO2 by the patient.

In examples, (a) the sealing structure comprises unrestrained edges adjacent to ends of the first substantially cylindrical region, (b) the sealing structure comprises an unrestrained edge all around the periphery of the entrance to the patient's airways except at the first substantially cylindrical region, (c) the portion of the face contacting portion forms a convex surface adapted to contact the patient's face, (d) the first substantially cylindrical region is located to contact or be alongside the patient's ala, (e) the first substantially cylindrical region is located to be substantially parallel to the patient's ala, (f) the patient interface further comprises a second one of the cylindrical region, (g) the cylindrical region comprises a second substantially cylindrical region that has a second uninterrupted circumference, wherein a portion of the second cylindrical region comprises a second portion of the face contacting portion, (h) wherein the first substantially cylindrical region comprises a hollow interior that is adapted to be in fluid communication with the pressure above ambient pressure, (i) the first substantially cylindrical region comprises two open ends, and/or (j) the first substantially cylindrical region is adapted to prevent the face contacting portion from a blowout when the patient interface is internally pressurized and adjusted by the patient.

Another aspect of one form of the present technology is a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 3 cmH2O to about 40 cmH2O above ambient air pressure in use, throughout the patient's respiratory cycle, while the patient is sleeping, to ameliorate sleep disordered breathing. The patient interface comprises a sealing structure comprising material folded upon itself to form an uninterrupted tubular shape, where only a portion of a circumference of the tubular shape is configured to contact the patient's face; a positioning and stabilising structure to maintain the sealing structure in sealing contact with an area surrounding an entrance to the patient's airways while maintaining a therapeutic pressure at the entrance to the patient's airways; a plenum chamber pressurised at a pressure above ambient pressure in use; and a gas washout vent configured to allow a flow of patient exhaled CO2 to an exterior of the patient interface to minimise rebreathing of exhaled CO2 by the patient, wherein an interior of the tubular shape is adapted to be in fluid communication with the pressure above ambient pressure.

In examples, (a) the uninterrupted tubular shape has an interior surface of the tube and an exterior surface of the tube, the interior surface of the tube is adapted to be exposed to the pressure above ambient pressure in use, a first portion of the exterior surface of the tube is adapted to be exposed to ambient pressure in use, and a second portion of the exterior surface of the tube is adapted to be exposed to the pressure above ambient pressure in use, (b) the sealing structure further comprises a surface that contacts around a periphery of the patient's airways and the portion of the uninterrupted tubular shape is part of the surface, (c) the uninterrupted tubular shape is open on at least one end, (d) the uninterrupted tubular shape is open on two ends, (e) the uninterrupted tubular shape is adapted to be alongside the patient's ala, (f) the uninterrupted tubular shape is adapted to contact the patient's ala, (g) the material is folded to form a second uninterrupted tubular shape where only a portion of a circumference of the second uninterrupted tubular shape is configured to contact the patient's face, (h) the uninterrupted tubular shapes are adapted to be on opposite sides of the patient's nose, and/or (i) the uninterrupted tubular shape is adapted to prevent the material from a blowout when the patient interface is internally pressurized and adjusted by the patient.

Another aspect of one form of the present technology is a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 3 cmH2O to about 40 cmH2O above ambient air pressure in use, throughout the patient's respiratory cycle, while the patient is sleeping, to ameliorate sleep disordered breathing. The patient interface comprises a sealing structure to seal the patient interface against the patient's face. The sealing structure comprises a first face contacting portion with an unconnected edge at an inner boundary of the sealing structure, a second face contacting portion that is part of a tubular structure, and the first face contacting portion and the second face contacting portion each form part of a continuous membrane that is configured to contact the patient's face around a periphery of the entrance to the patient's airways. The patient interface further comprises a positioning and stabilising structure to maintain the sealing structure in sealing contact with an area surrounding an entrance to the patient's airways while maintaining a therapeutic pressure at the entrance to the patient's airways; a plenum chamber pressurised at a pressure above ambient pressure in use; and a gas washout vent configured to allow a flow of patient exhaled CO2 to an exterior of the patient interface to minimise rebreathing of exhaled CO2 by the patient.

In examples, (a) the patient interface further comprises a plurality of the second face contacting portion, (b) the second face contacting portion is adapted to contact the patient's face adjacent to or on the patient's ala, and/or (c) the tubular structure is adapted to prevent the continuous membrane from a blowout when the patient interface is internally pressurized and adjusted by the patient.

Another aspect of one form of the present technology is a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 3 cmH2O to about 40 cmH2O above ambient air pressure in use, throughout the patient's respiratory cycle, while the patient is sleeping, to ameliorate sleep disordered breathing. The patient interface comprises a sealing structure to seal the patient interface against the patient's face. The sealing structure comprises a sealing membrane, and a flap attached on a first end to the sealing membrane and attached on a second end to another structure to prevent the sealing membrane from blowing outward due to the therapy pressure. The patient interface further comprises a positioning and stabilising structure to maintain the sealing structure in sealing contact with an area surrounding an entrance to the patient's airways while maintaining a therapeutic pressure at the entrance to the patient's airways; a plenum chamber pressurised at a pressure above ambient pressure in use; and a gas washout vent configured to allow a flow of patient exhaled CO2 to an exterior of the patient interface to minimise rebreathing of exhaled CO2 by the patient.

In examples, (a) the sealing membrane and the flap form part of a tubular structure, and/or (b) the sealing membrane is adapted to contact all around a periphery of the entrance to the patient's airways and the flap is only provided for a portion of the periphery.

Another aspect of one form of the present technology is a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 3 cmH2O to about 40 cmH2O above ambient air pressure in use, throughout the patient's respiratory cycle, while the patient is sleeping, to ameliorate sleep disordered breathing. The patient interface comprises a sealing structure to seal the patient interface against the patient's face. The sealing structure comprises a sealing membrane adapted to contact the patient's face around a periphery of the entrance to the patient's airways, and a cylindrical region underlying and attached to the sealing membrane. The patient interface further comprises a positioning and stabilising structure to maintain the sealing structure in sealing contact with an area surrounding an entrance to the patient's airways while maintaining a therapeutic pressure at the entrance to the patient's airways; a plenum chamber pressurised at a pressure above ambient pressure in use; and a gas washout vent configured to allow a flow of patient exhaled CO2 to an exterior of the patient interface to minimise rebreathing of exhaled CO2 by the patient.

In examples, (a) the cylindrical region is located adjacent to the patient's ala, (b) the cylindrical region includes an axis that is substantially parallel to the patient's ala, (c) the cylindrical region is adapted to prevent the sealing membrane from blowing away from the entrance to the patient's airways when the plenum chamber is pressurized at the pressure above ambient pressure, and/or (d) the sealing membrane includes an unconnected edge all around a periphery of the entrance to the patient's airways.

Another aspect of one form of the present technology is a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 3 cmH2O to about 40 cmH2O above ambient air pressure in use, throughout the patient's respiratory cycle, while the patient is sleeping, to ameliorate sleep disordered breathing. The patient interface comprises a sealing structure to seal the patient interface against the patient's face. The sealing structure comprises a sealing membrane comprising an interior surface and an exterior surface adapted to contact the patient's face around a periphery of the entrance to the patient's airways, and a rib underlying and attached to the interior surface such that the rib resists deformation of the sealing membrane when pressure is applied to the interior surface. The patient interface further comprises a positioning and stabilising structure to maintain the sealing structure in sealing contact with an area surrounding an entrance to the patient's airways while maintaining a therapeutic pressure at the entrance to the patient's airways; a plenum chamber pressurised at a pressure above ambient pressure in use; and a gas washout vent configured to allow a flow of patient exhaled CO2 to an exterior of the patient interface to minimise rebreathing of exhaled CO2 by the patient.

In examples, (a) the exterior surface includes a convex portion, (b) the interior surface has a concave portion, (c) the concave portion and the convex portion are located directly opposite one another on the exterior surface and interior surface, respectively, and the rib is attached to the interior surface at the concave portion, (d) the rib is readily crushed by a forced applied to the patient interface to hold the patient interface to the patient, (e) the patient interface further comprises a plurality of the rib, (f) the rib is adapted to be adjacent the patient's nose, (g) the rib is adapted to prevent the sealing membrane from a blowout when the patient interface is internally pressurized and adjusted by the patient, and/or (h) the rib is substantially orthogonal to the interior surface.

Another aspect of one form of the present technology is a cushion assembly for a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing. The cushion assembly may include an elastomeric seal-forming portion shaped to be bisected by a sagittal plane that includes a line tangent to the elastomeric seal-forming portion at a superior tangent point and an inferior tangent point. The elastomeric seal-forming portion may include a dome-shaped superior region that straddles the sagittal plane in the vicinity of the superior tangent point and a saddle-shaped inferior region that straddles the sagittal plane and includes the inferior tangent point. The elastomeric seal-forming portion may also include a first support region extending from the saddle-shaped inferior region to the dome-shaped superior region, the first support region having a consistent elastomeric wall thickness that is greater than the elastomeric wall thickness of the dome-shaped superior region and the saddle-shaped inferior region. The elastomeric seal-forming portion may further include a second support region adjacent the first support region that extends from the saddle-shaped inferior region to the dome-shaped superior region, the second support region being bounded by the first support region on a proximal side and having a distal side opposite the proximal side, the elastomeric wall thickness in the second support region increases from the distal side to the proximal side.

Another aspect of one form of the present technology is a cushion assembly for a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing. The cushion assembly may include an elastomeric seal-forming structure shaped to be bisected by a sagittal plane that includes a line tangent to the elastomeric seal-forming structure at a superior tangent point and an inferior tangent point. The elastomeric seal-forming structure may include a posterior central opening and an anterior central opening opposite the posterior central opening and may include a plurality closed path concentric to the posterior central opening. A dome-shaped superior region may straddle the sagittal plane in the vicinity of the superior tangent point, the dome-shaped superior region being positioned on the outermost closed path. A saddle-shaped superior region may straddle the sagittal plane in the vicinity of the superior tangent point, the saddle-shaped superior region being positioned on the innermost closed path. A saddle-shaped inferior region may straddle the sagittal plane and may include the inferior tangent point, the saddle-shaped inferior region being on both the innermost closed path and the outermost closed path. An elastomeric wall thickness of the elastomeric seal-forming structure may be invariable along a portion of the outermost closed path extending from the saddle-shaped inferior region to the dome-shaped superior region. The elastomeric wall thickness of the elastomeric seal-forming structure may vary along a portion of the innermost closed path that extends from saddle-shaped inferior region to the saddle-shaped superior region.

Another aspect of one form of the present technology is a cushion assembly for a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing. The cushion assembly may include an elastomeric seal-forming structure that is shaped to be bisected by a sagittal plane that has a line that is tangent to the elastomeric seal-forming structure at a superior tangent point and at an inferior tangent point. A first nasal bridge region of the elastomeric seal-forming structure may straddle the sagittal plane in the vicinity of the superior tangent point. A second nasal bridge region of the elastomeric seal-forming structure may straddle the sagittal plane in the vicinity of the superior tangent point and is configured to seal against the patient's nasal bridge when the cushion is mounted on the patient's face, the second nasal bridge region having a thinner elastomeric wall than the first nasal bridge region. A chin region of the elastomeric seal-forming structure may straddle the sagittal plane and includes the inferior tangent point, the chin region being configured to engage the patient's chin when the cushion is mounted on the patient's face, the chin region having the same elastomeric wall thickness as the first nasal bridge region. A first support region and a second support region may be positioned side by side and both extend from the chin region to the first nasal bridge region, the first support region having a consistent elastomeric wall thickness, and the second support region having a varied elastomeric wall thickness.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described herein can provide improved functioning in a processor, such as of a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 TREATMENT SYSTEMS

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 RESPIRATORY SYSTEM AND FACIAL ANATOMY

Figure 1A:
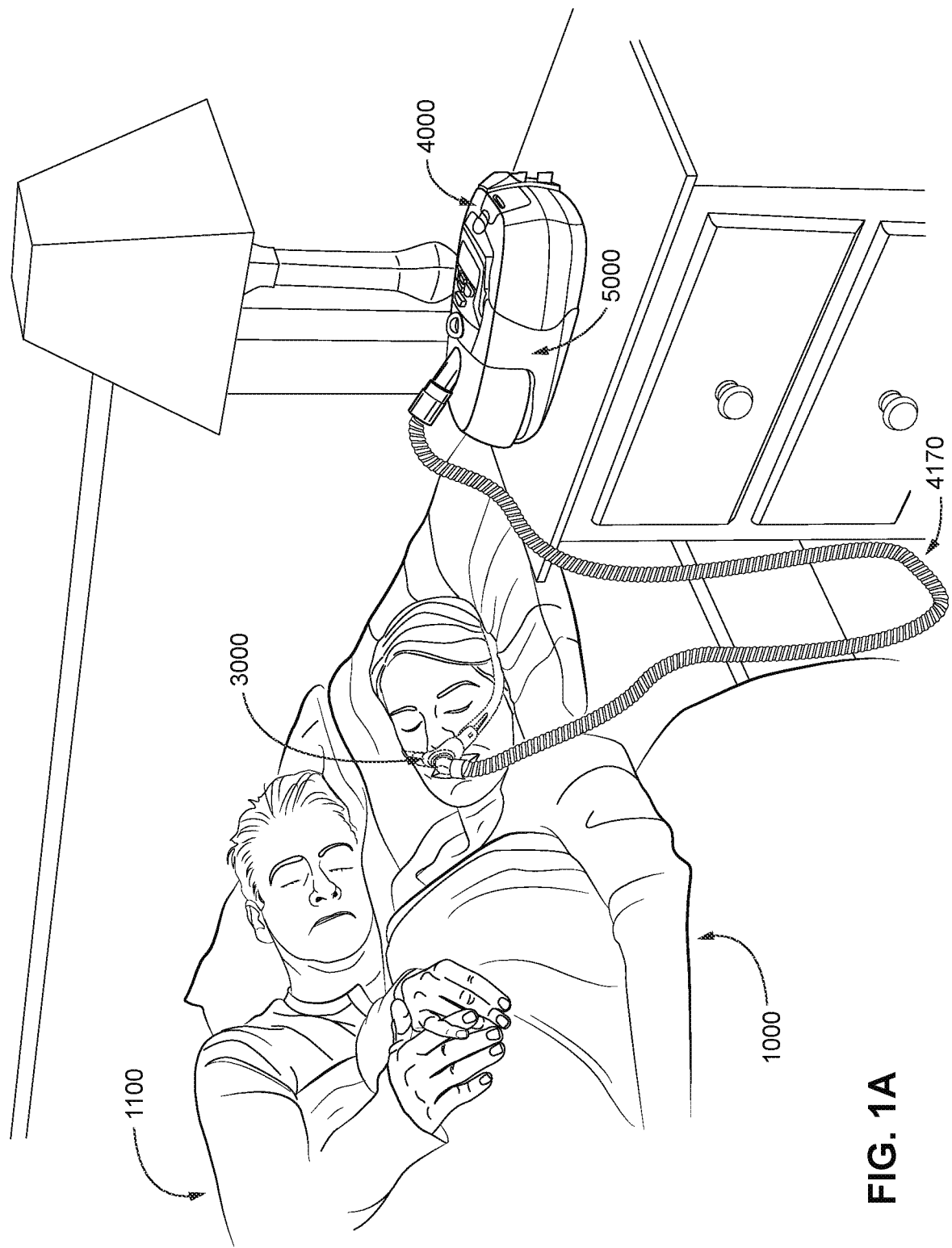
Figure 1B:
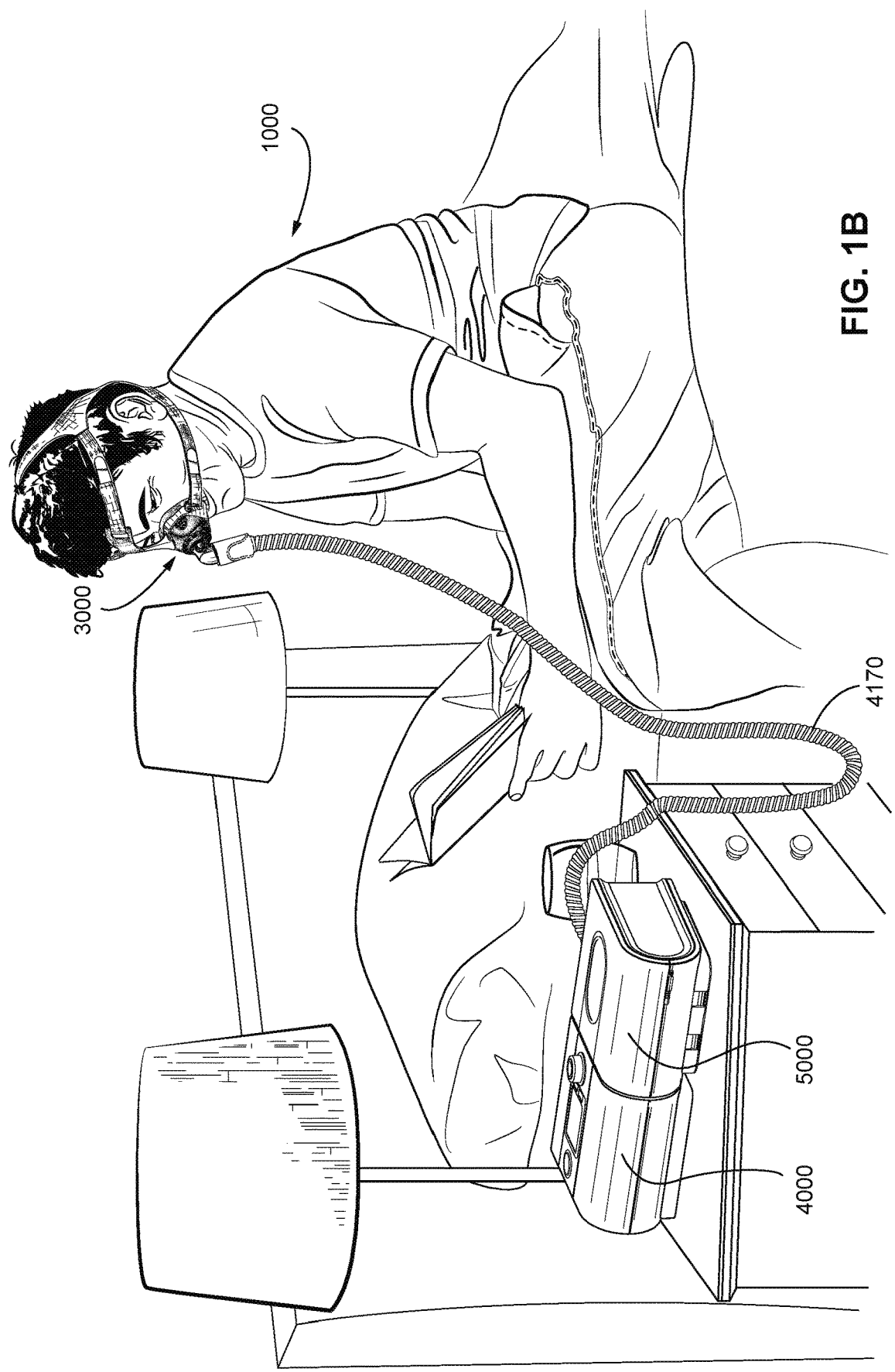
Figure 1C:
Figure 2A:
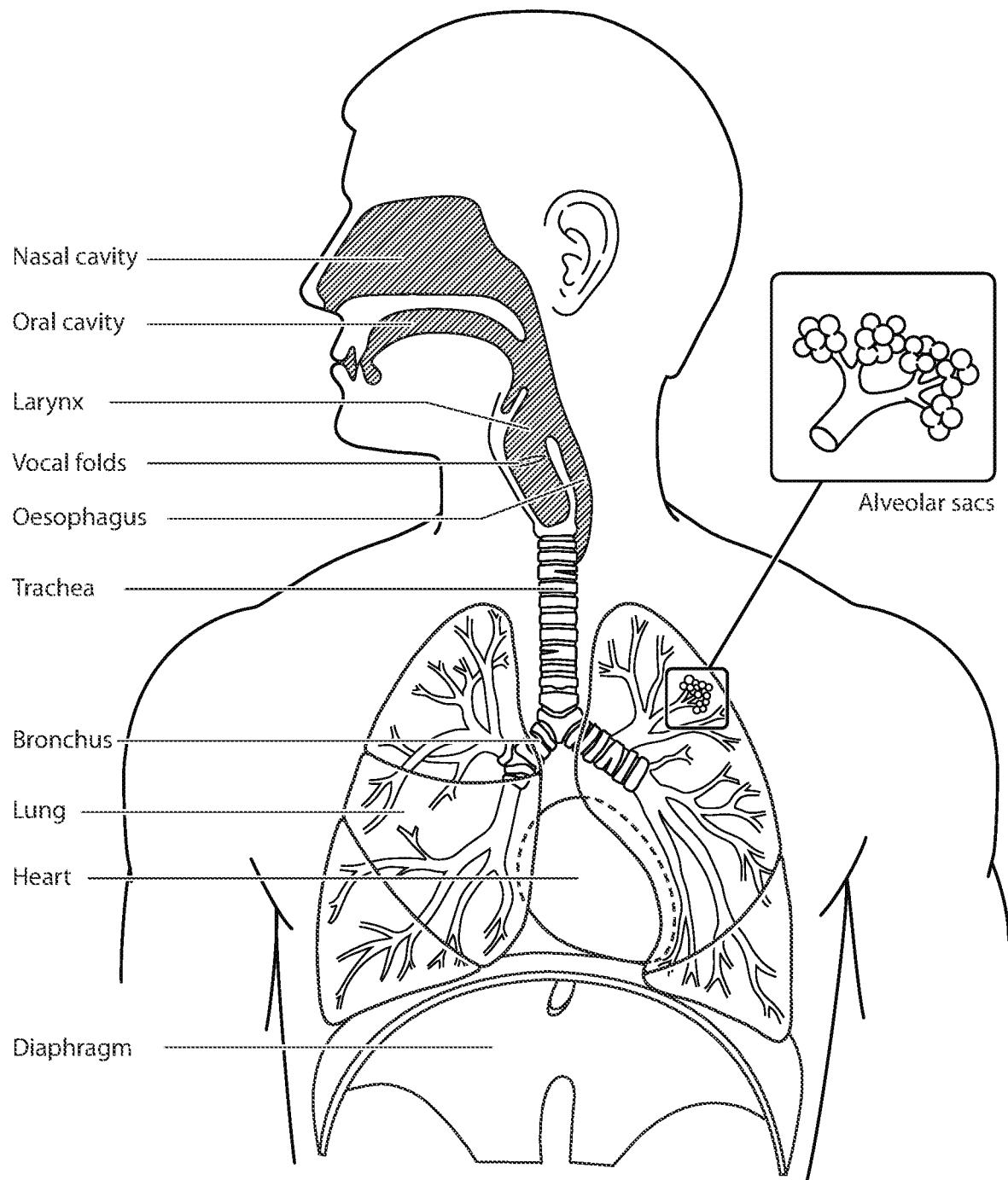
FIG. 2A shows an overview of a human respiratory system including the nasal and oral cavities, the larynx, vocal folds, oesophagus, trachea, bronchus, lung, alveolar sacs, heart and diaphragm.
Figure 2B:
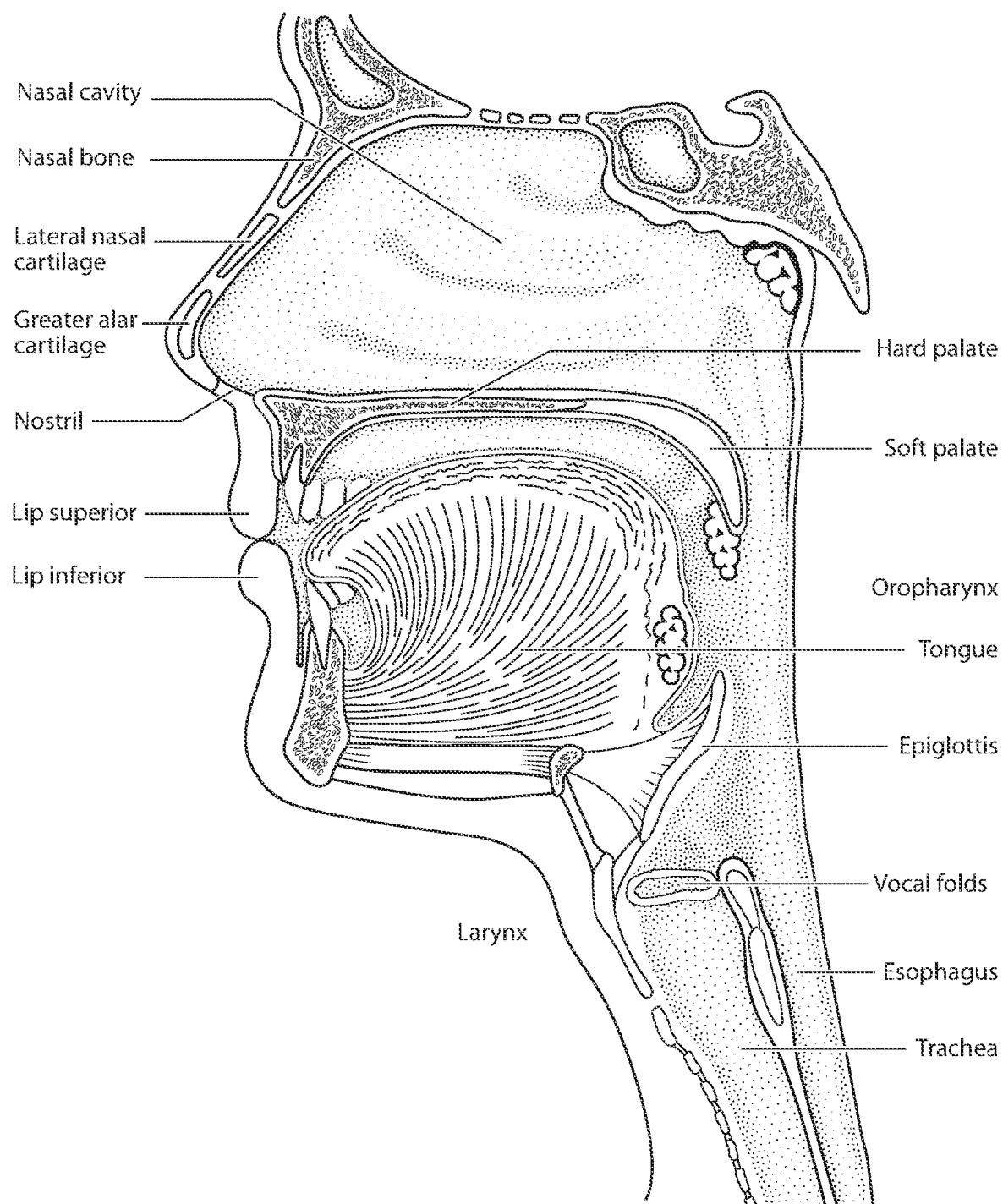
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
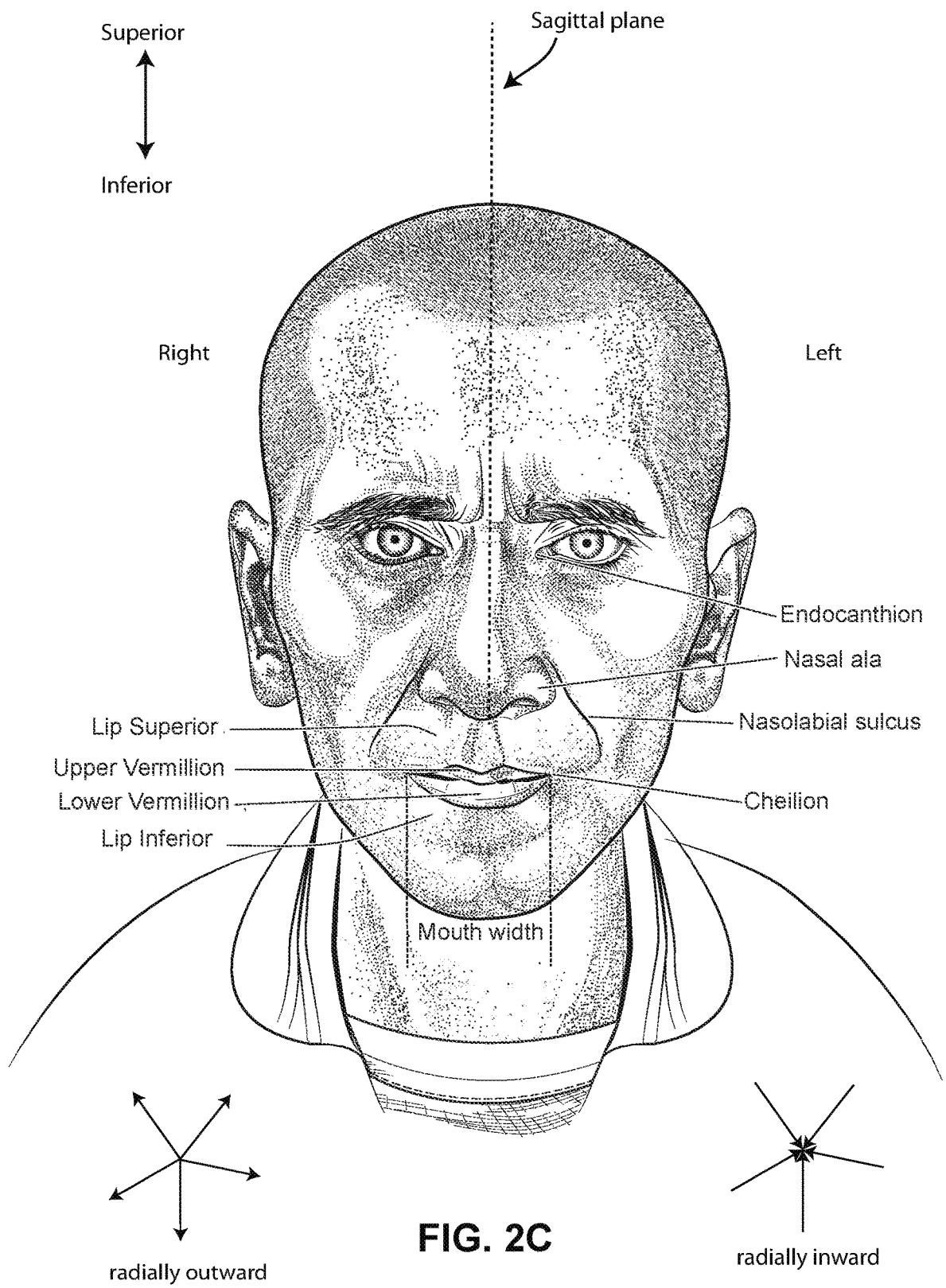
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
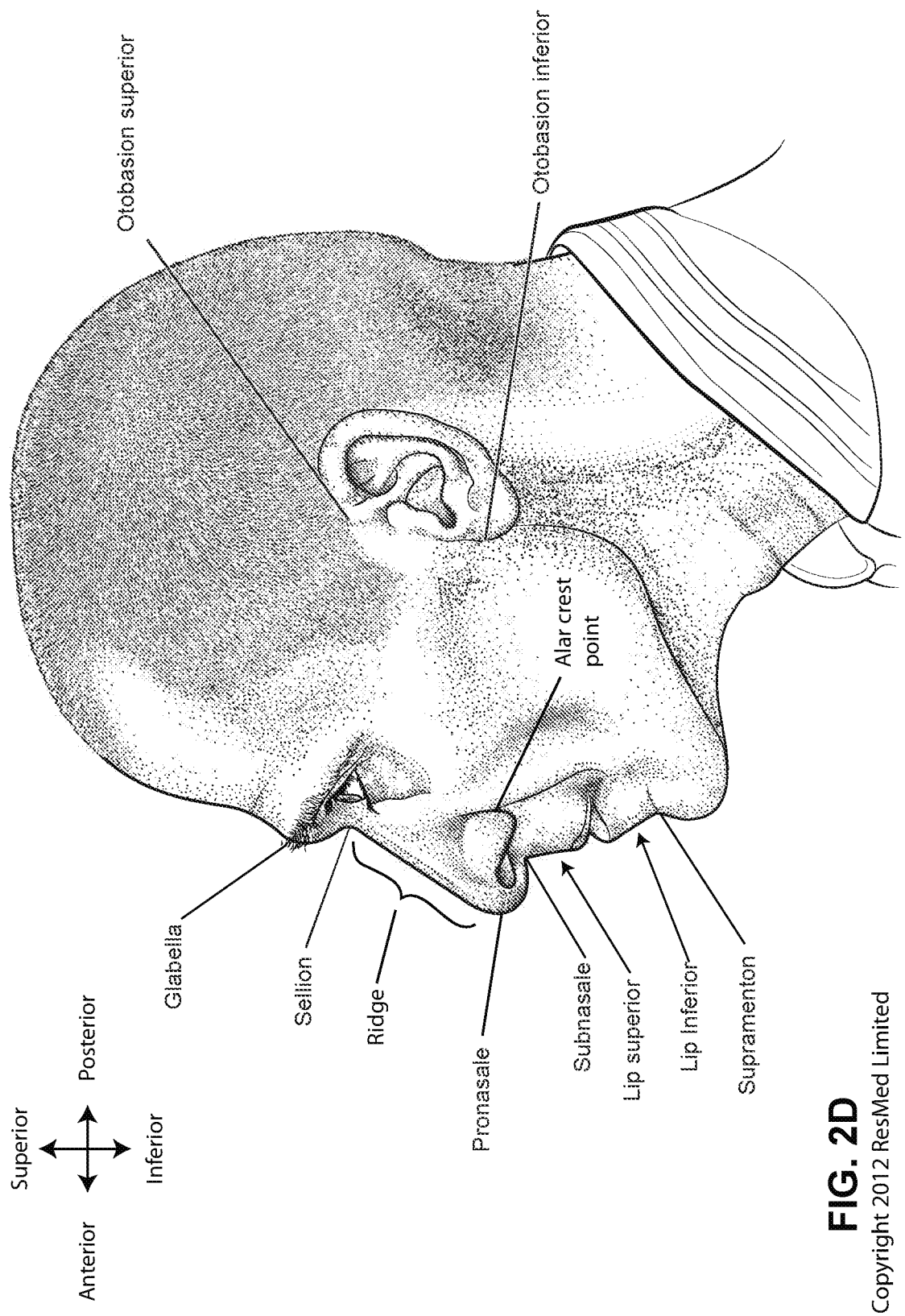
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
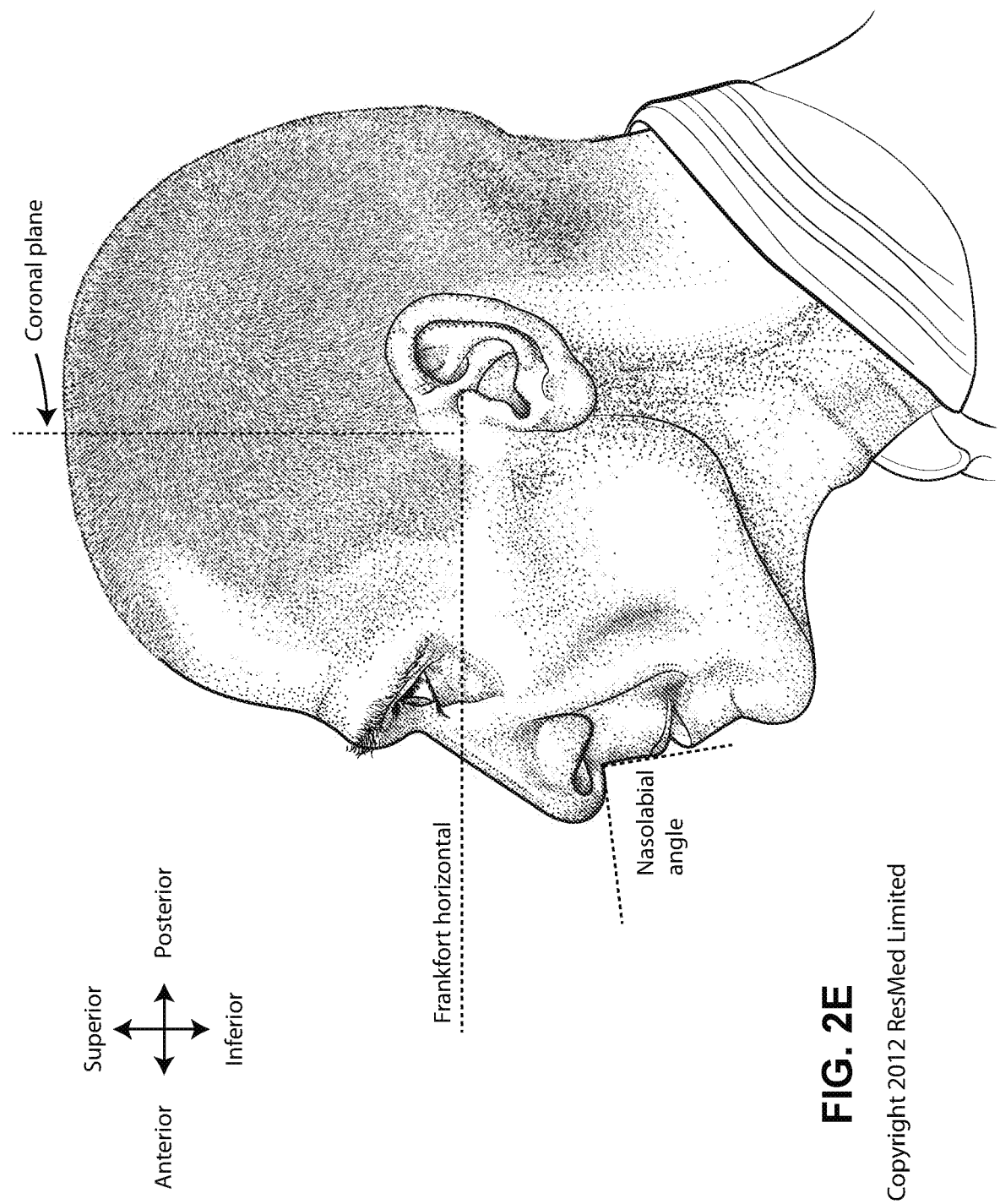

FIG. 2E is a further side view of a head. The approximate locations of the Frankfort horizontal and nasolabial angle are indicated. The coronal plane is also indicated.

Figure 2F:
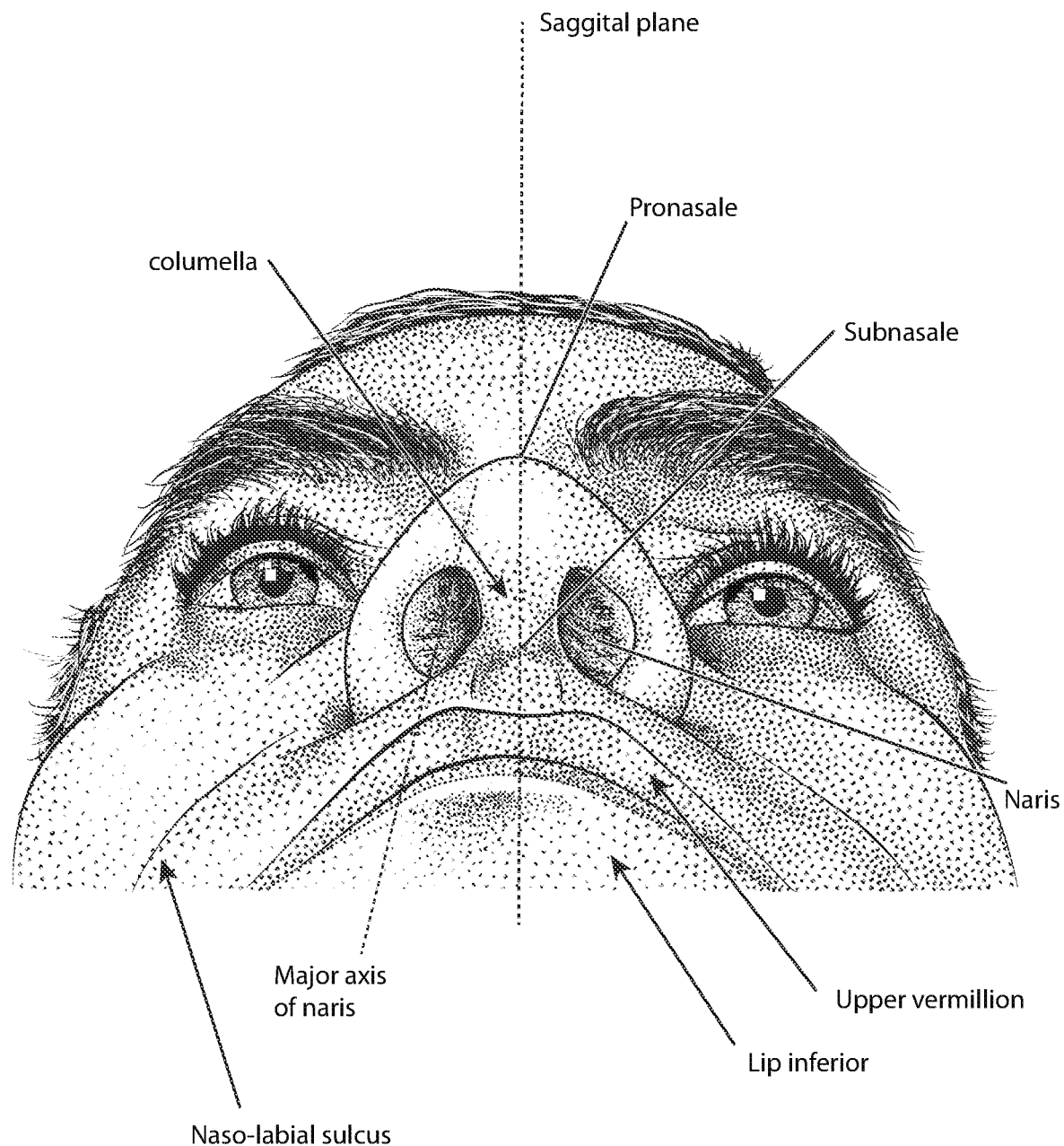

FIG. 2F shows a base view of a nose with several features identified including naso-labial sulcus, lip inferior, upper Vermilion, naris, subnasale, columella, pronasale, the major axis of a naris and the sagittal plane.

Figures 2G, 2H, 2I:
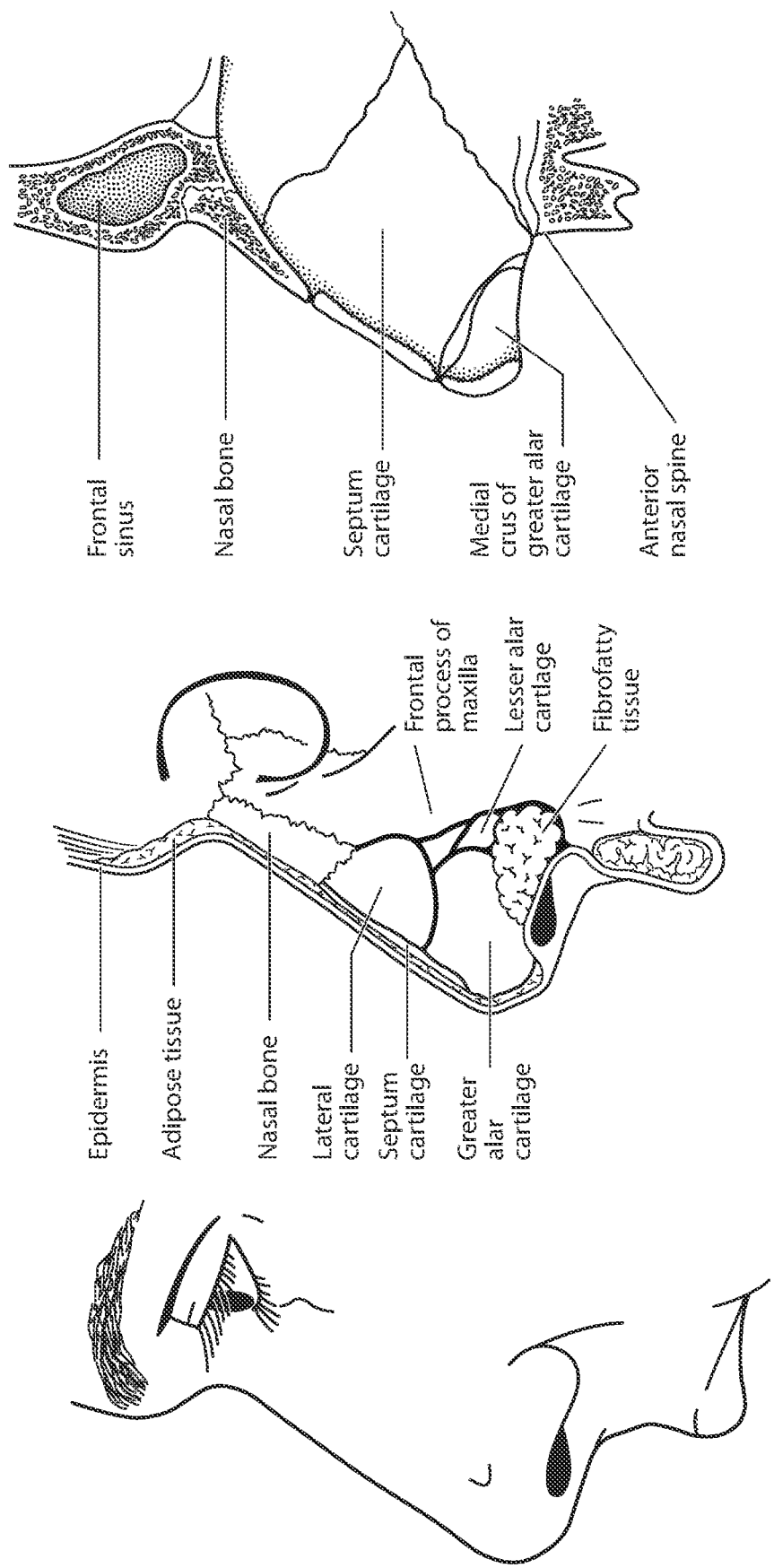

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
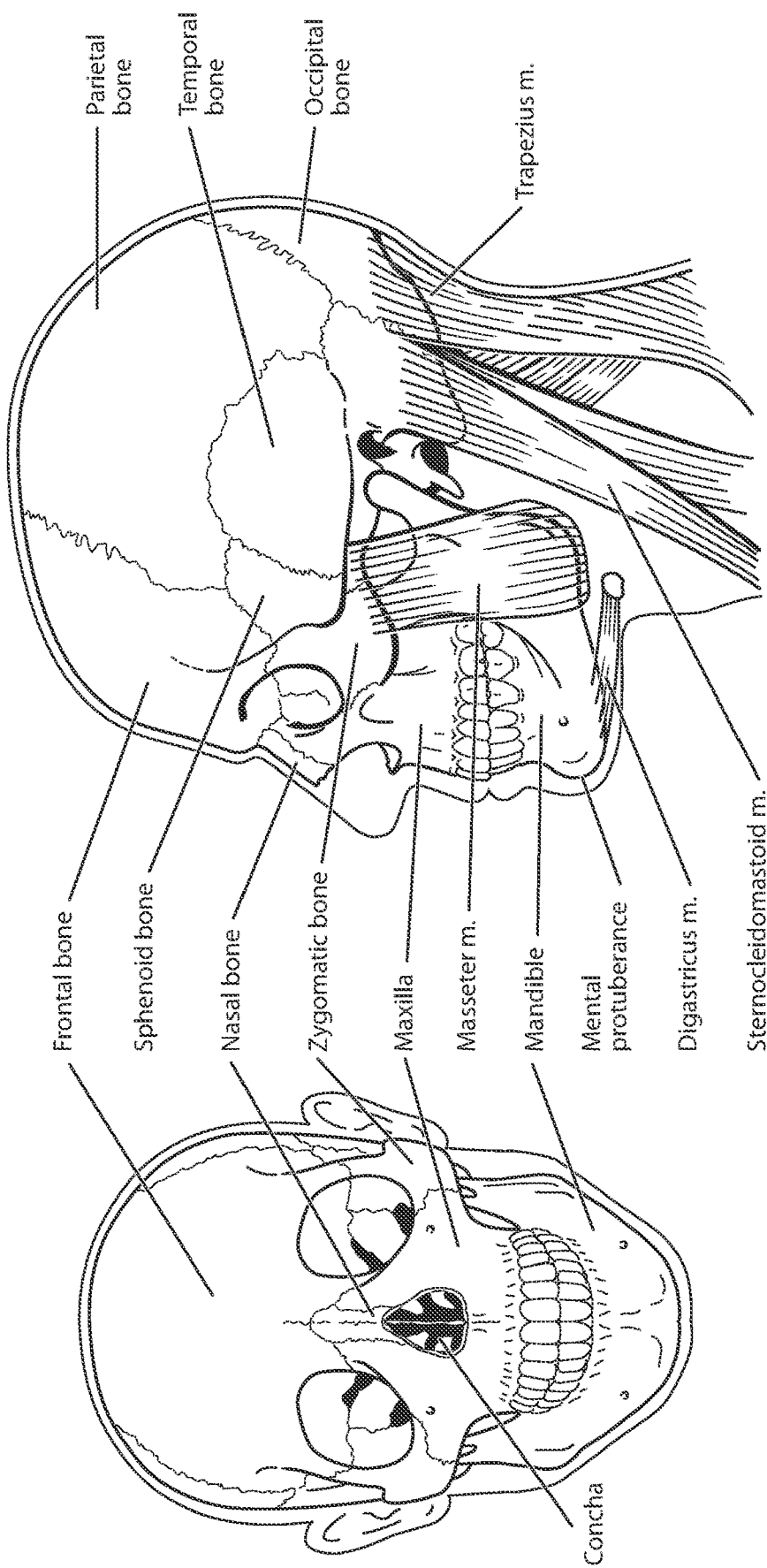

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
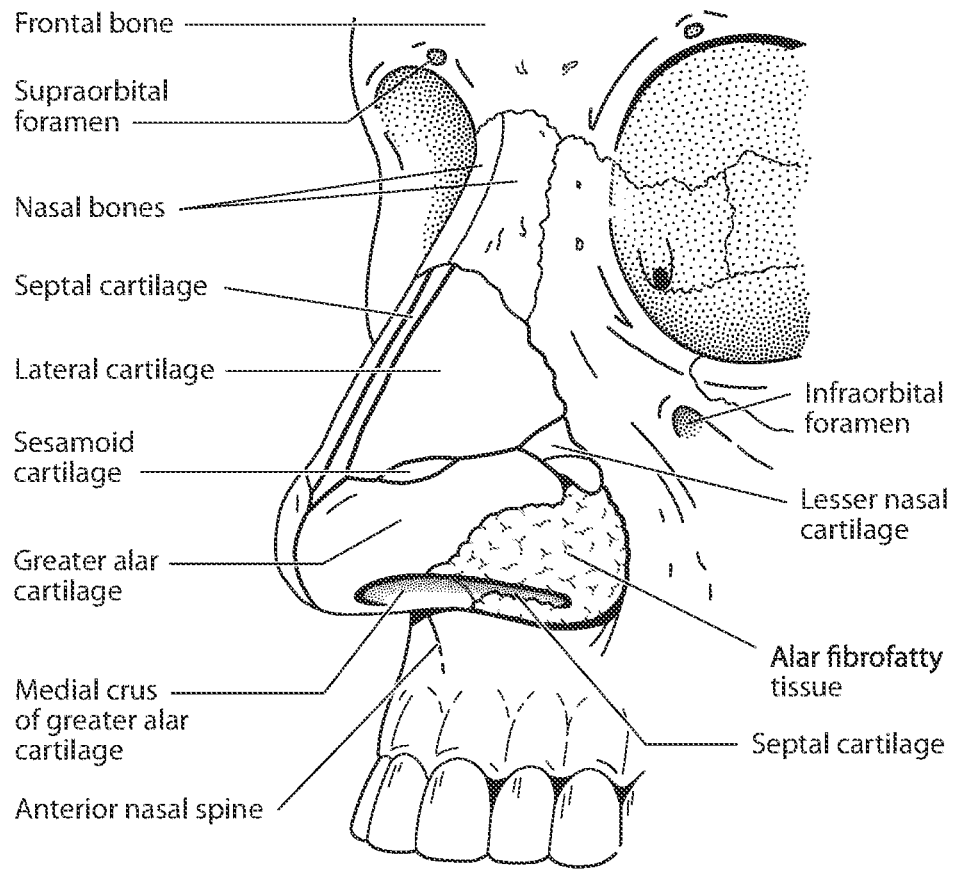

FIG. 2L shows an anterolateral view of a nose.

3.3 PATIENT INTERFACE

Figure 3A:
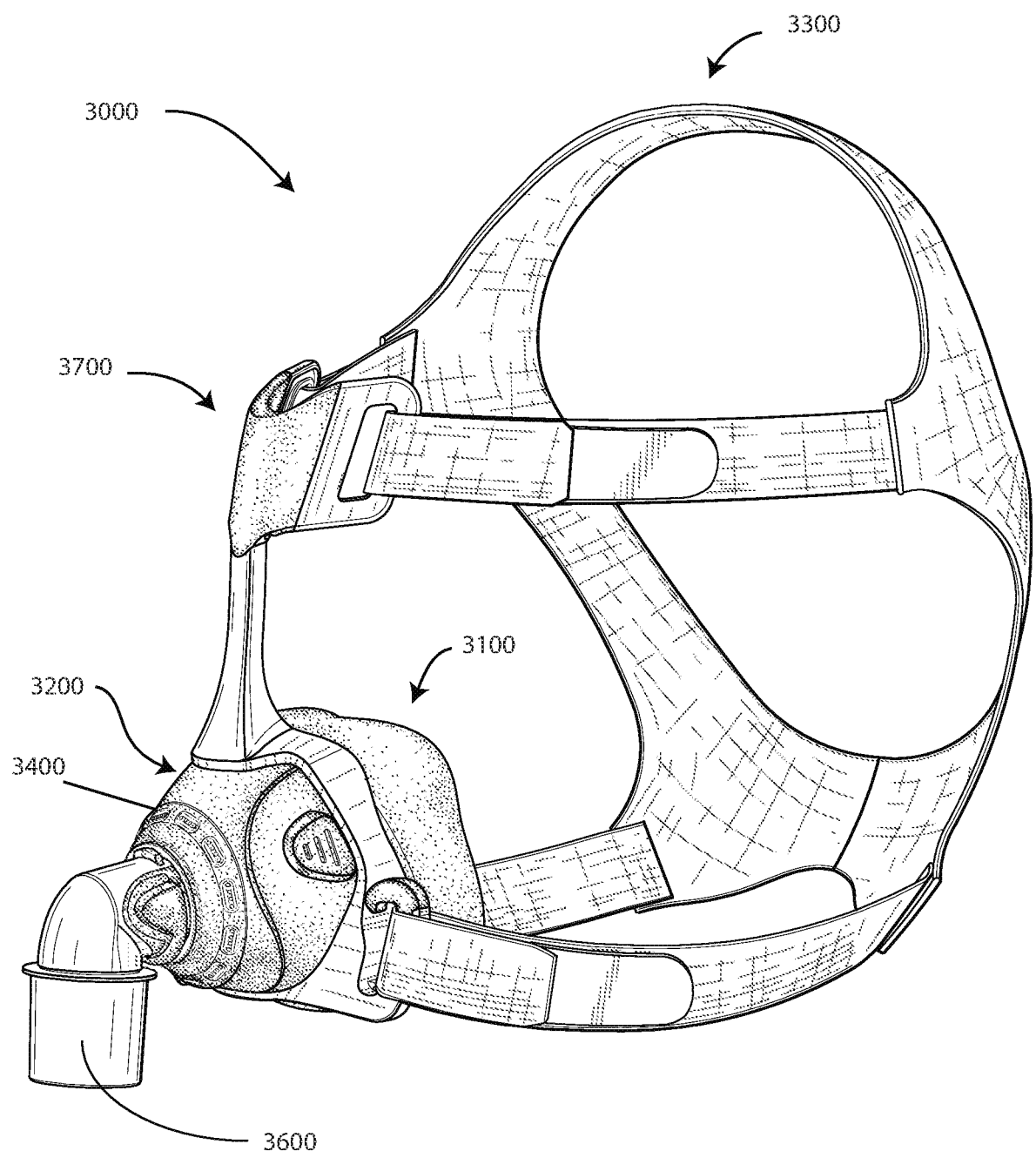

FIG. 3A shows a patient interface in the form of a nasal mask in accordance with one form of the present technology.

Figure 3B:
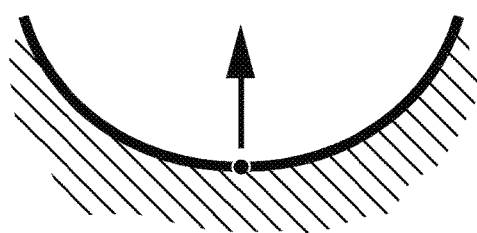

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
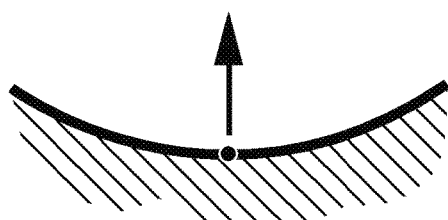

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
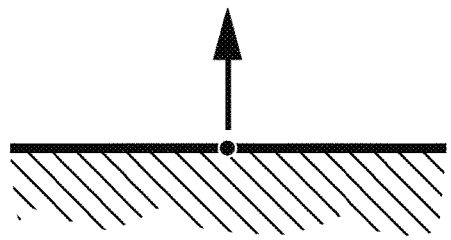

FIG. 3D shows a schematic of a cross-section through a structure at a point. An outward normal at the point is indicated. The curvature at the point has a value of zero.

Figure 3E:
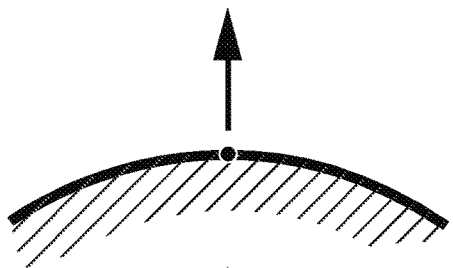

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
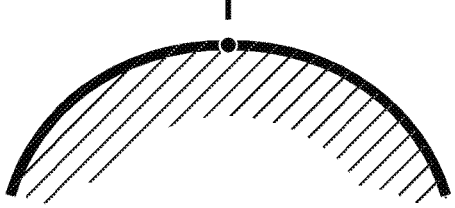

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
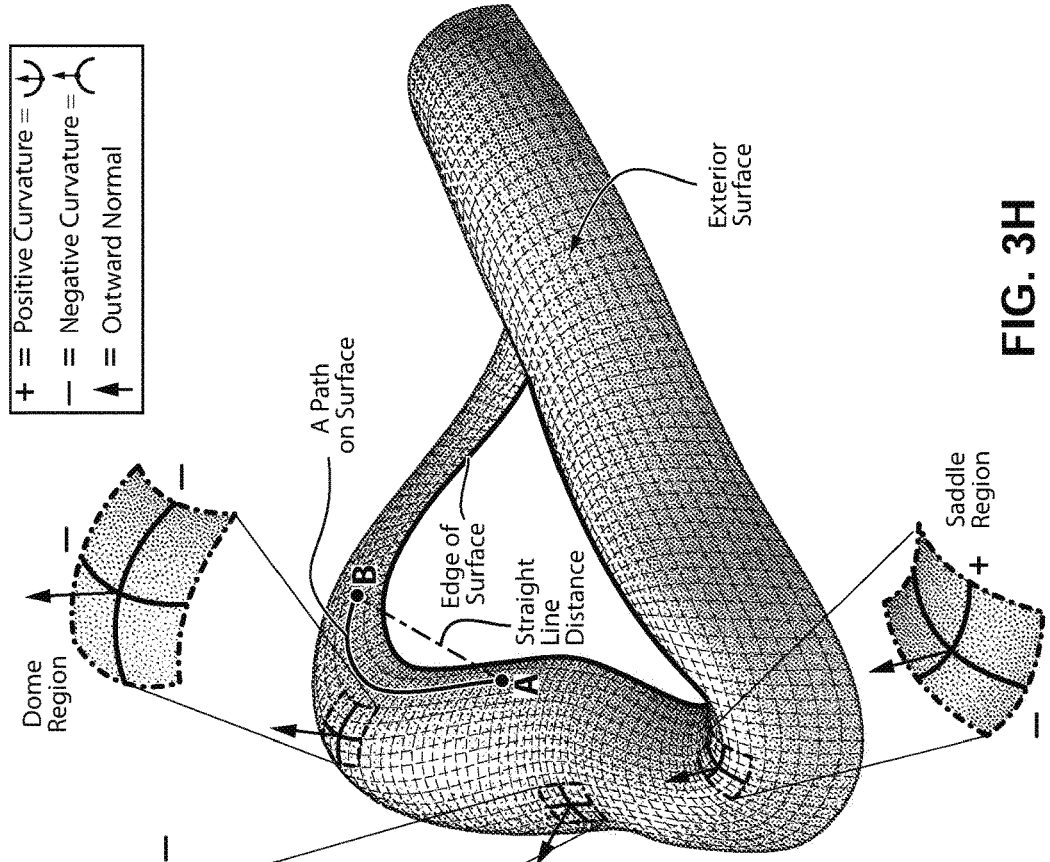
Figure 3G:
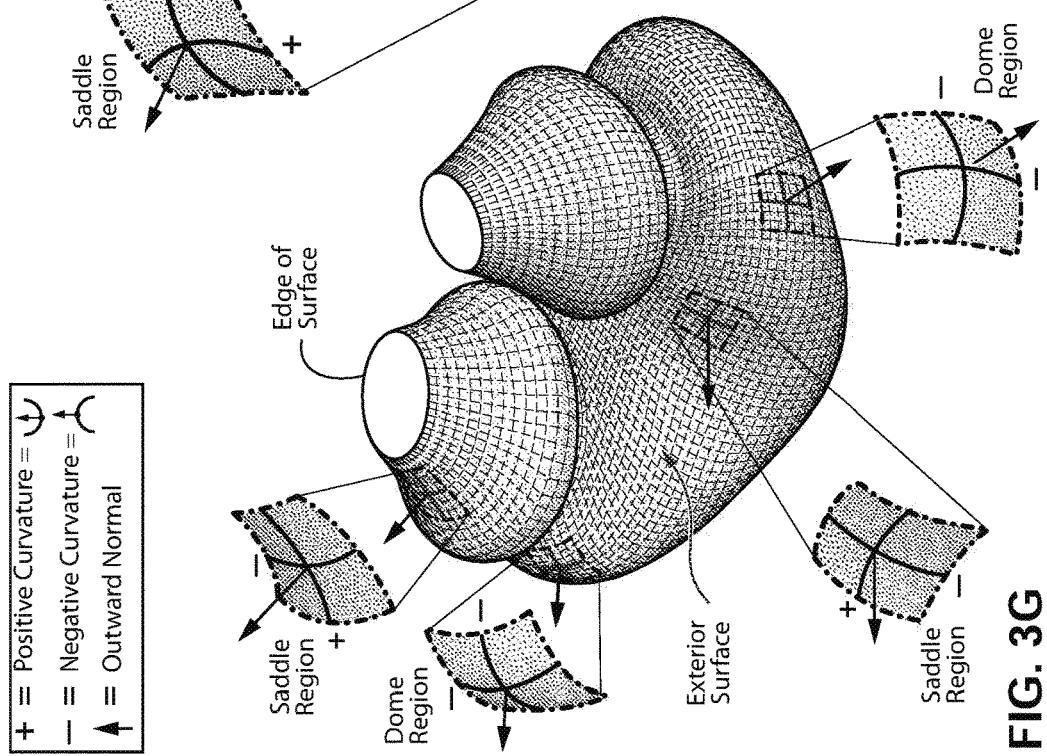

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
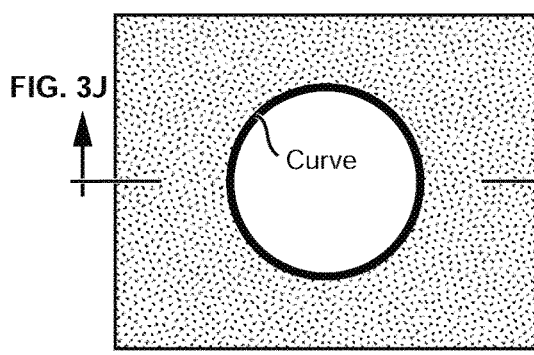

FIG. 3I shows the surface of a structure, with a one dimensional hole in the surface. The illustrated plane curve forms the boundary of a one dimensional hole.

Figure 3K:
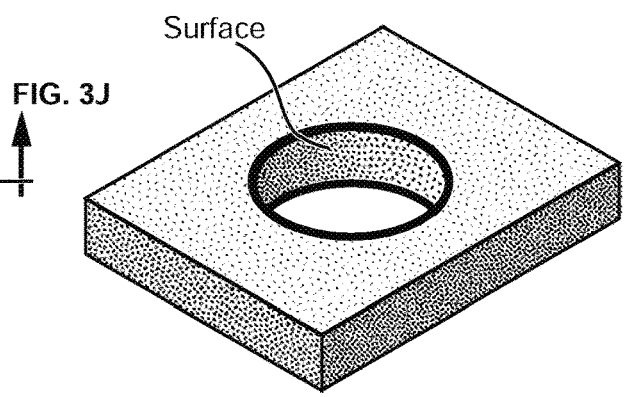
Figure 3J:
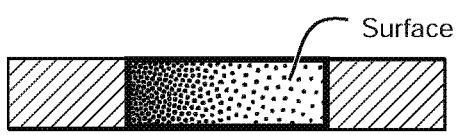

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
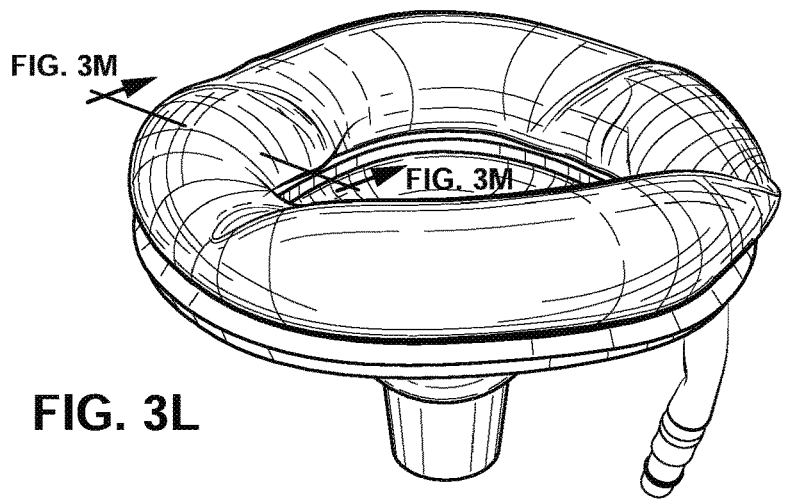

FIG. 3L shows a mask having an inflatable bladder as a cushion.

Figure 3M:
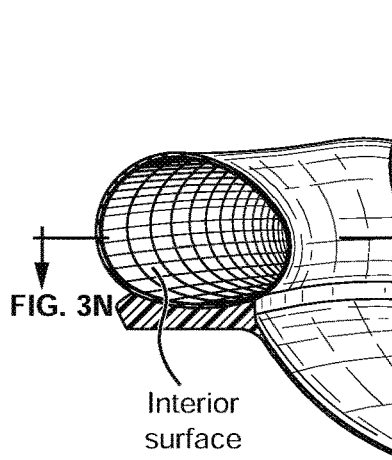

FIG. 3M shows a cross-section through the mask of FIG. 3L, and shows the interior surface of the bladder. The interior surface bounds the two dimensional hole in the mask.

Figure 3N:
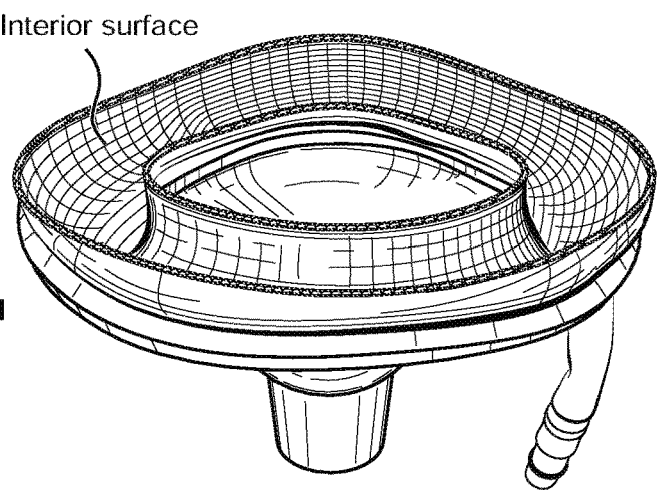

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

Figure 3S:
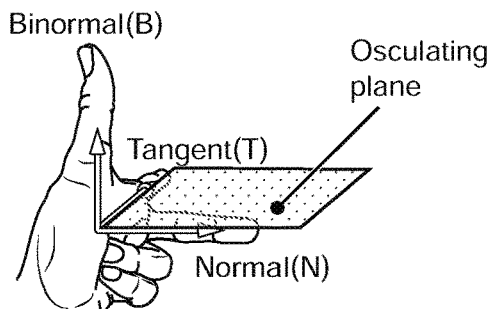
Figure 3S:
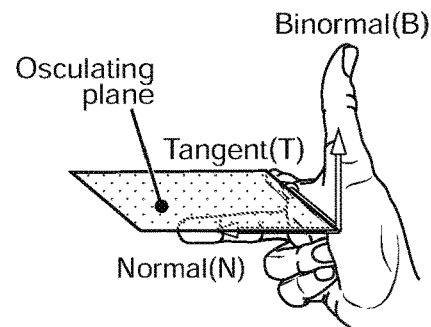
Figure 3S:
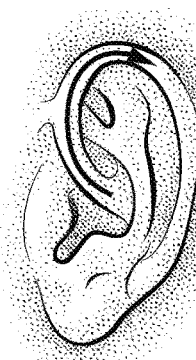
Figure 3S:
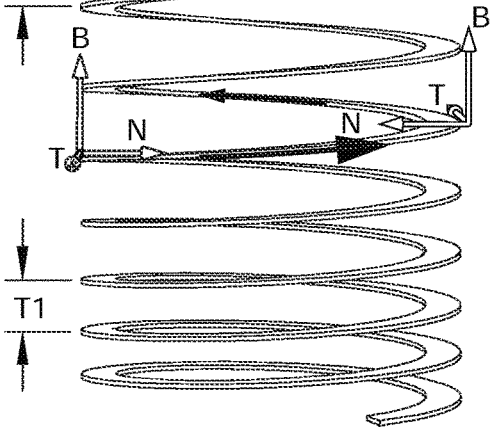
Figure 3S:
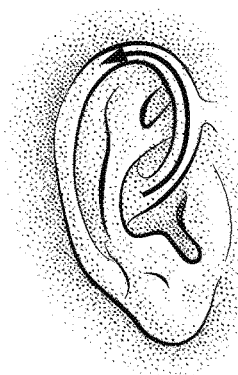

FIG. 3S shows a right-hand helix.

Figure 3T:
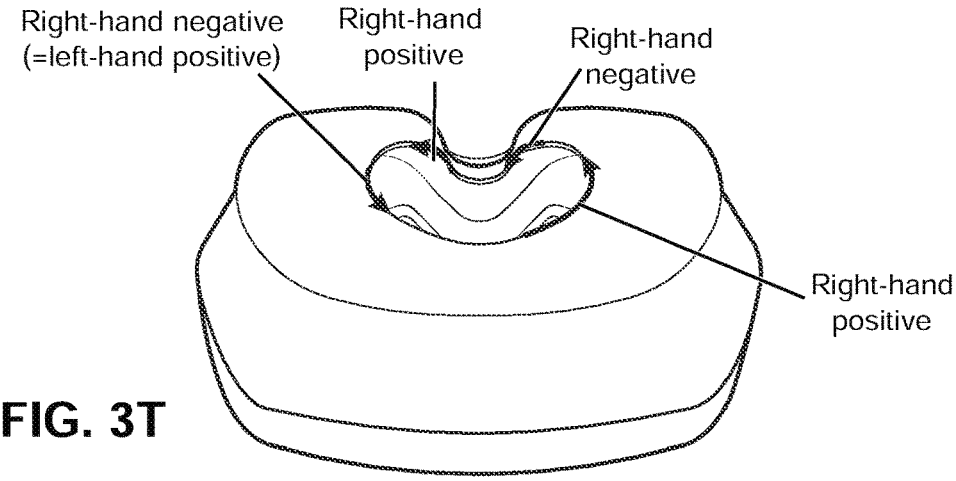

FIG. 3T shows a view of a mask, including the sign of the torsion of the space curve defined by the edge of the sealing membrane in different regions of the mask.

3.4 RPT DEVICE

Figure 3U:
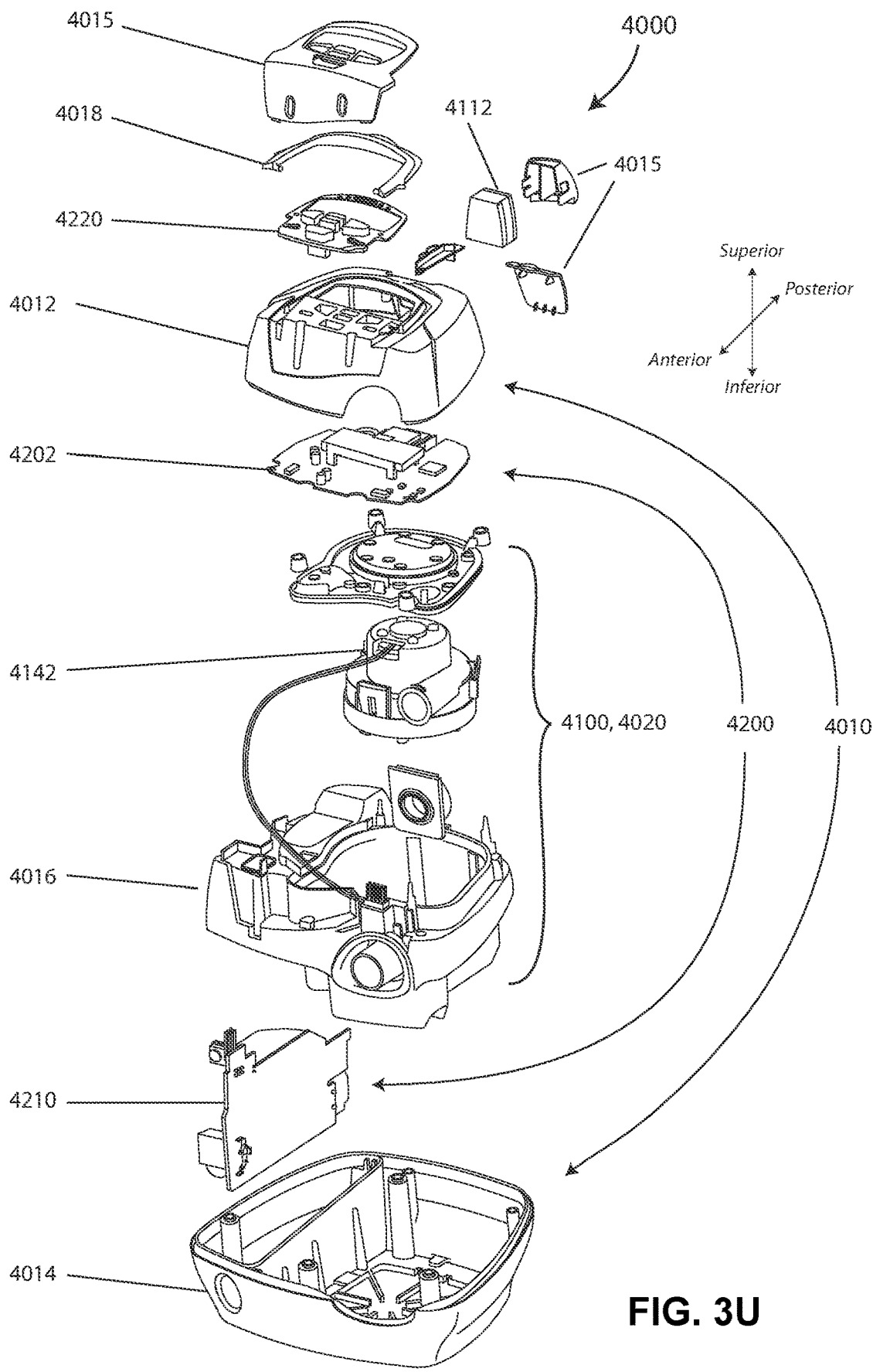

FIG. 3U shows an RPT device in accordance with one form of the present technology.

3.5 HUMIDIFIER

Figure 3V:
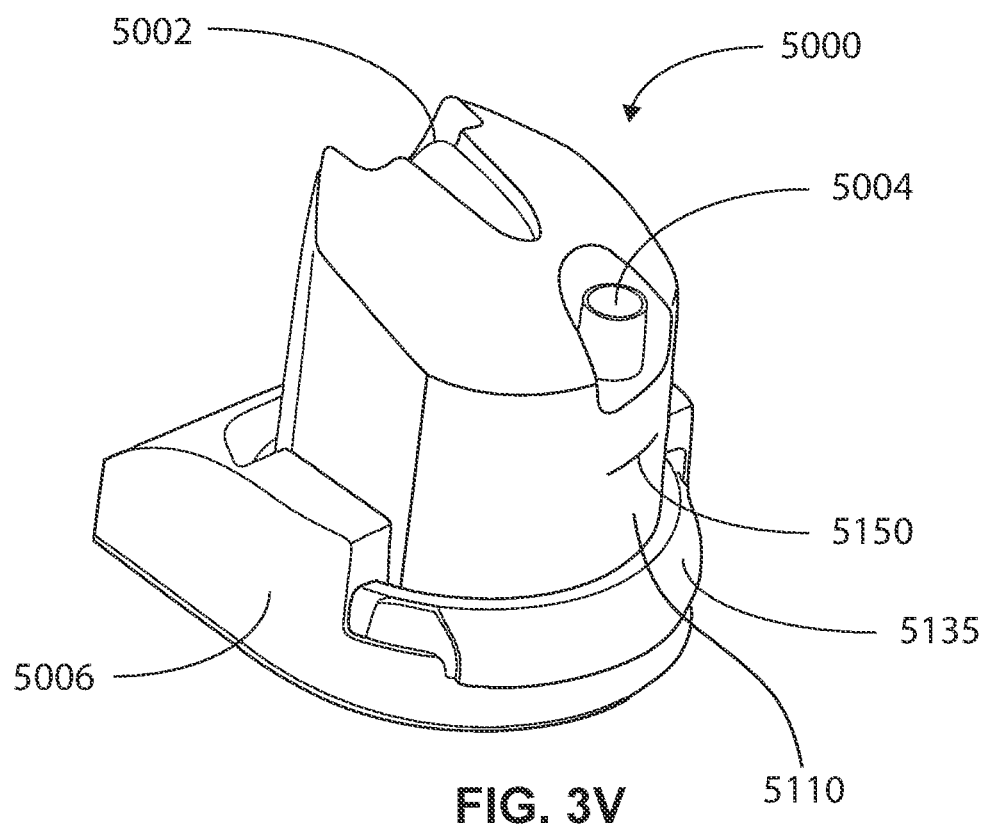

FIG. 3V shows an isometric view of a humidifier in accordance with one form of the present technology.

Figure 3W:
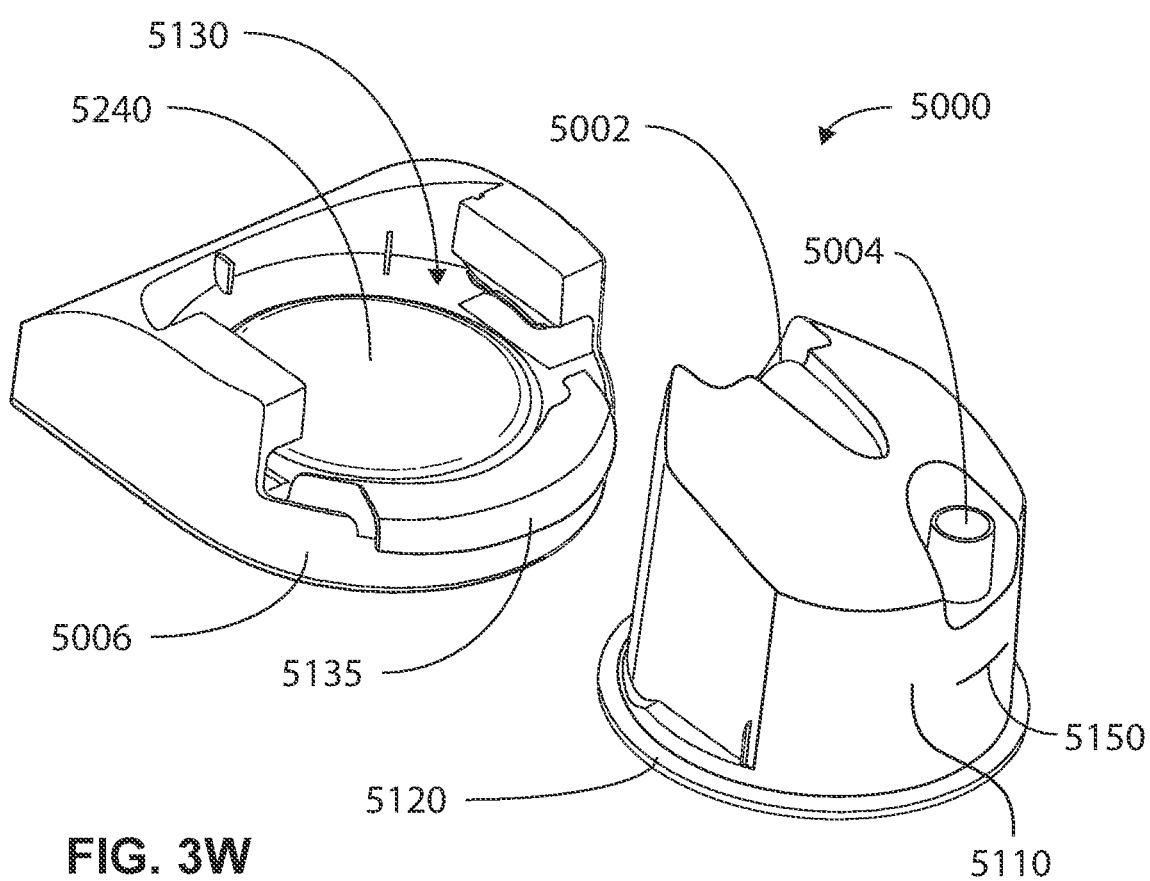

FIG. 3W shows an isometric view of a humidifier in accordance with one form of the present technology, showing a humidifier reservoir 5110 removed from the humidifier reservoir dock 5130.

3.6 SEAL-FORMING STRUCTURE AND PATIENT INTERFACE

Figure 4:
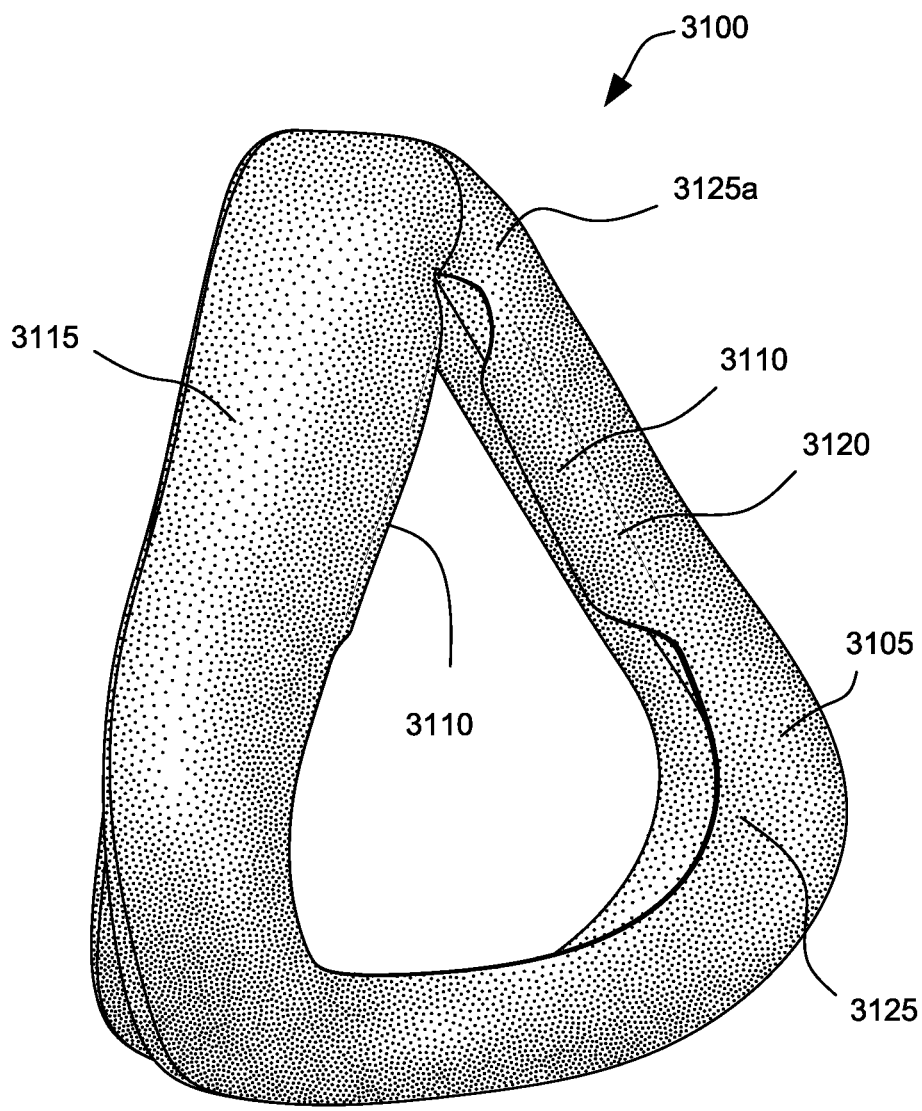

FIG. 4 depicts a perspective view of a seal forming structure.

Figure 5:
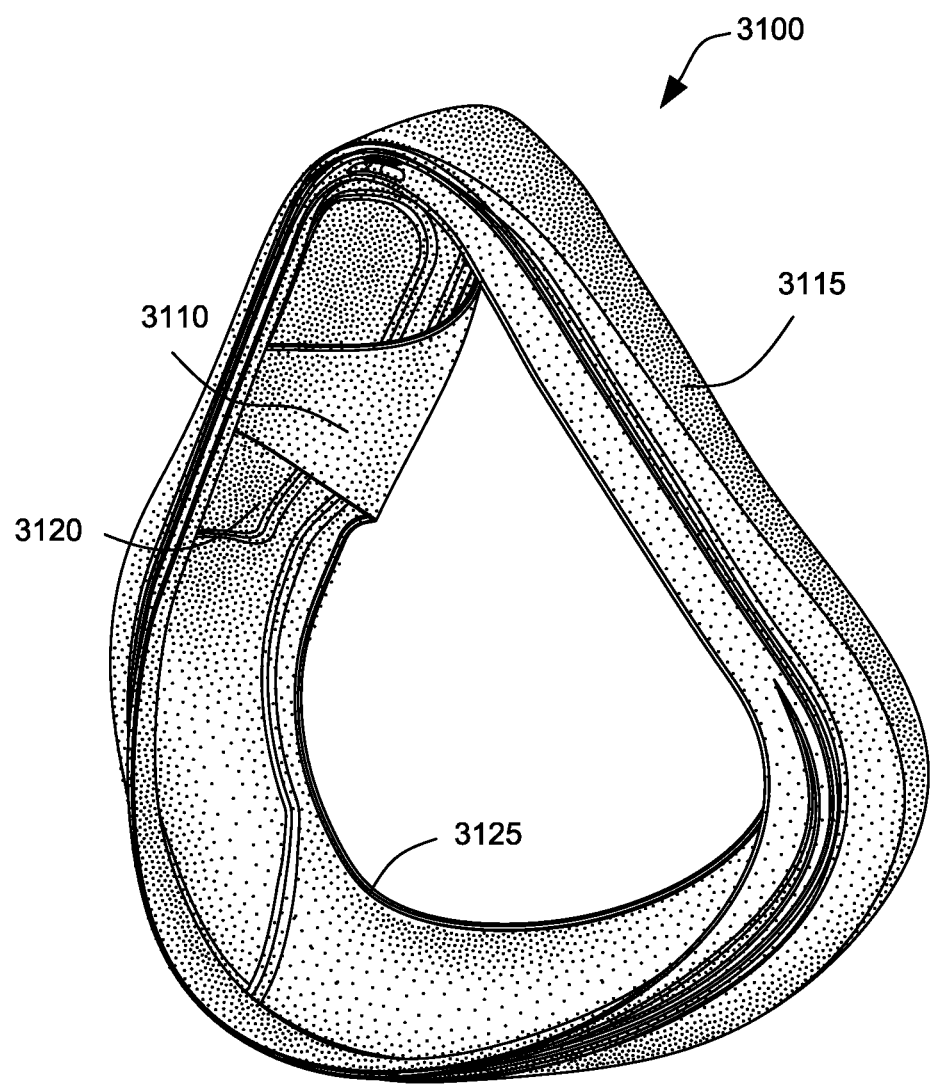

FIG. 5 depicts a perspective view of a seal forming structure.

Figure 5A:
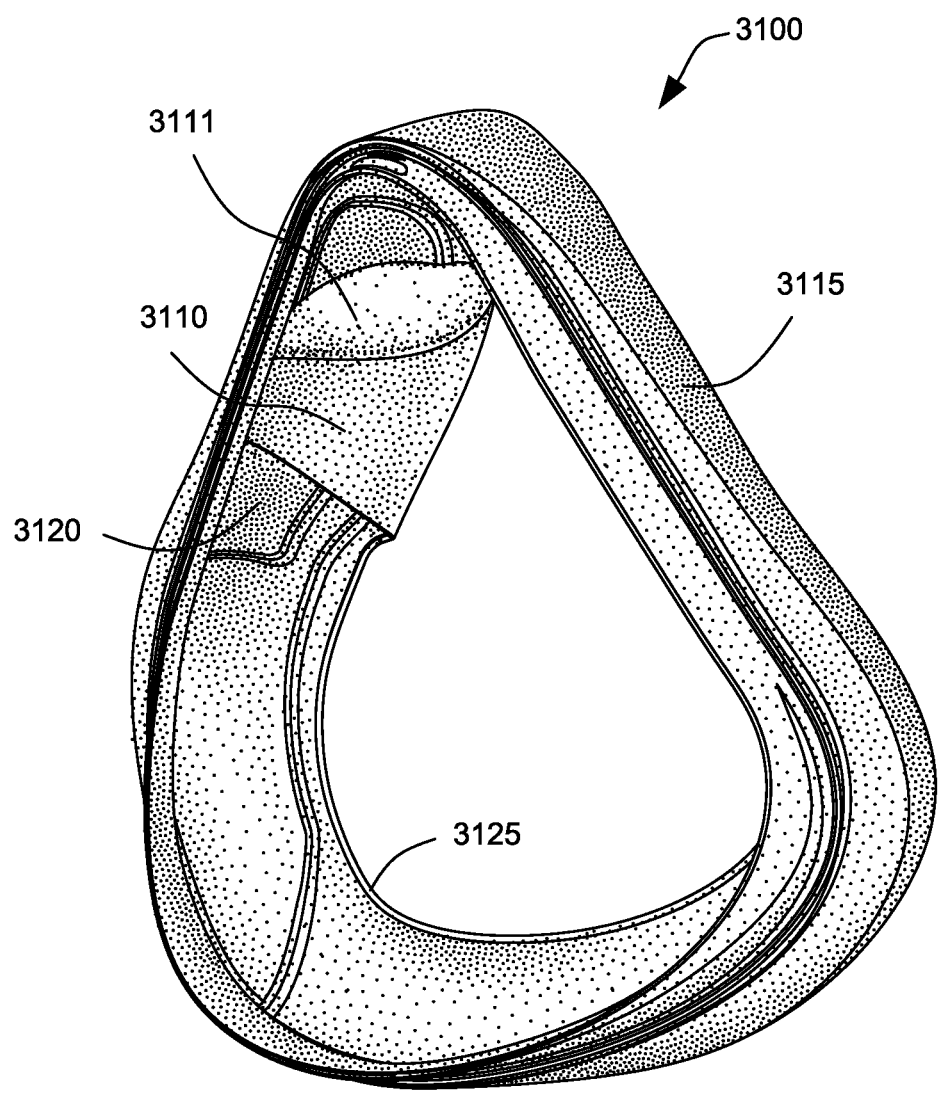

FIG. 5A depicts a perspective view of a seal forming structure where a loop includes a closed end.

Figure 6:
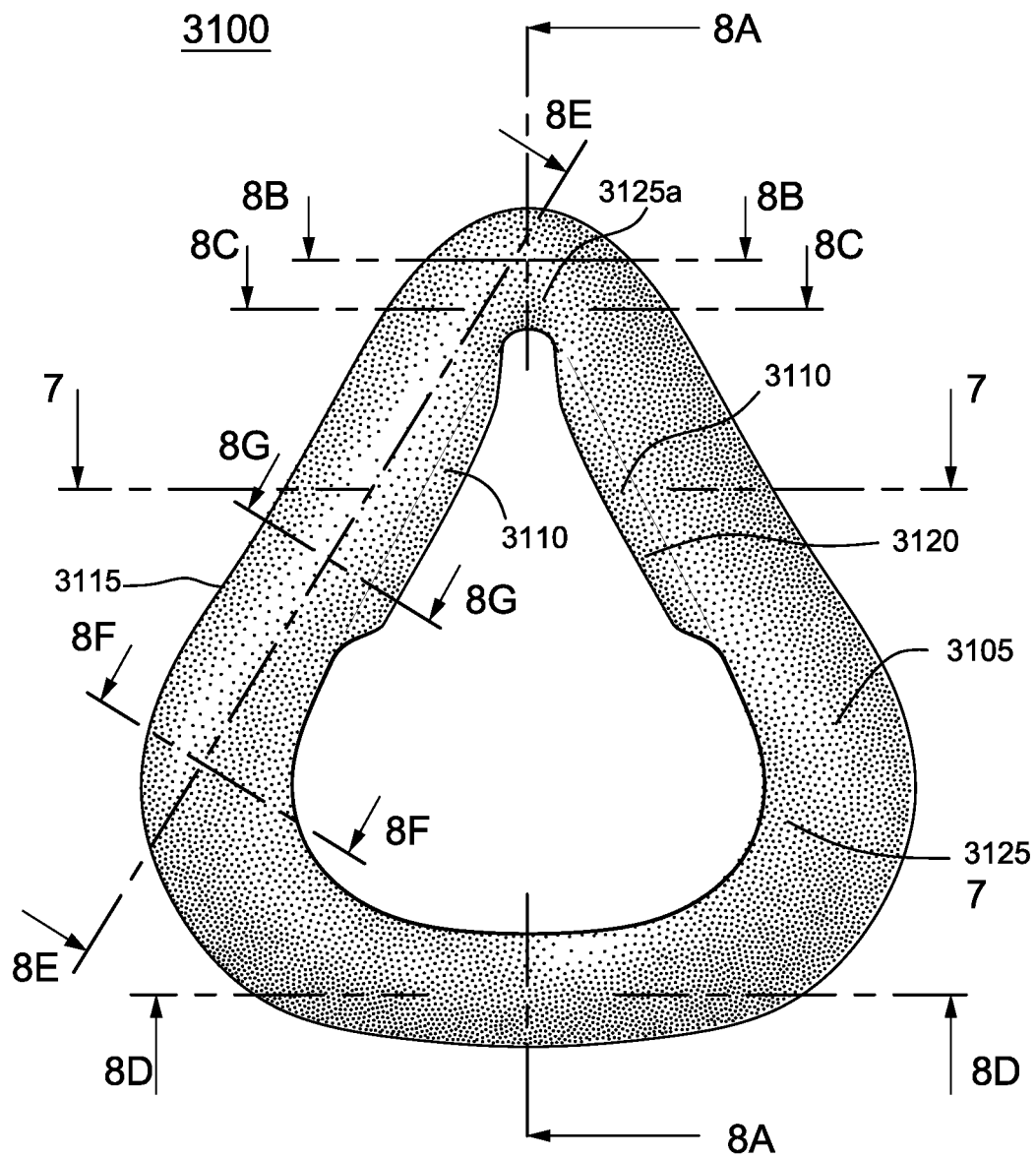

FIG. 6 depicts a plan view of a seal forming structure.

Figure 7:
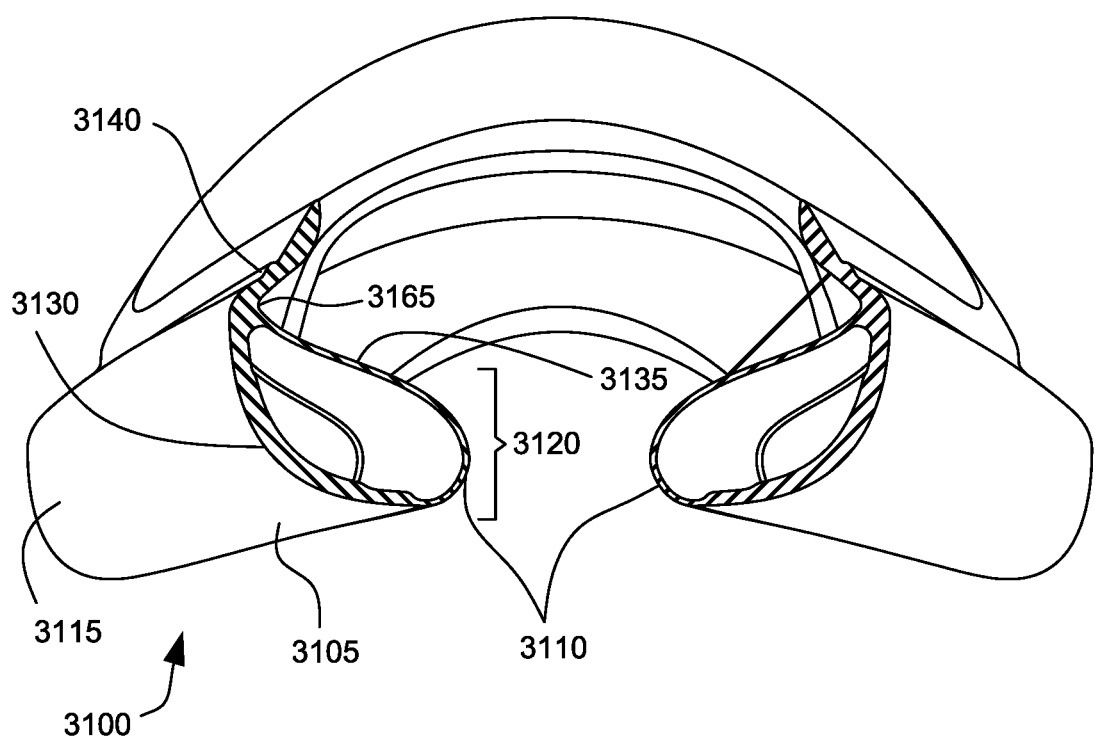

FIG. 7 depicts a cross-sectional view taken along lines 7-7 of FIG. 6.

Figure 7A:
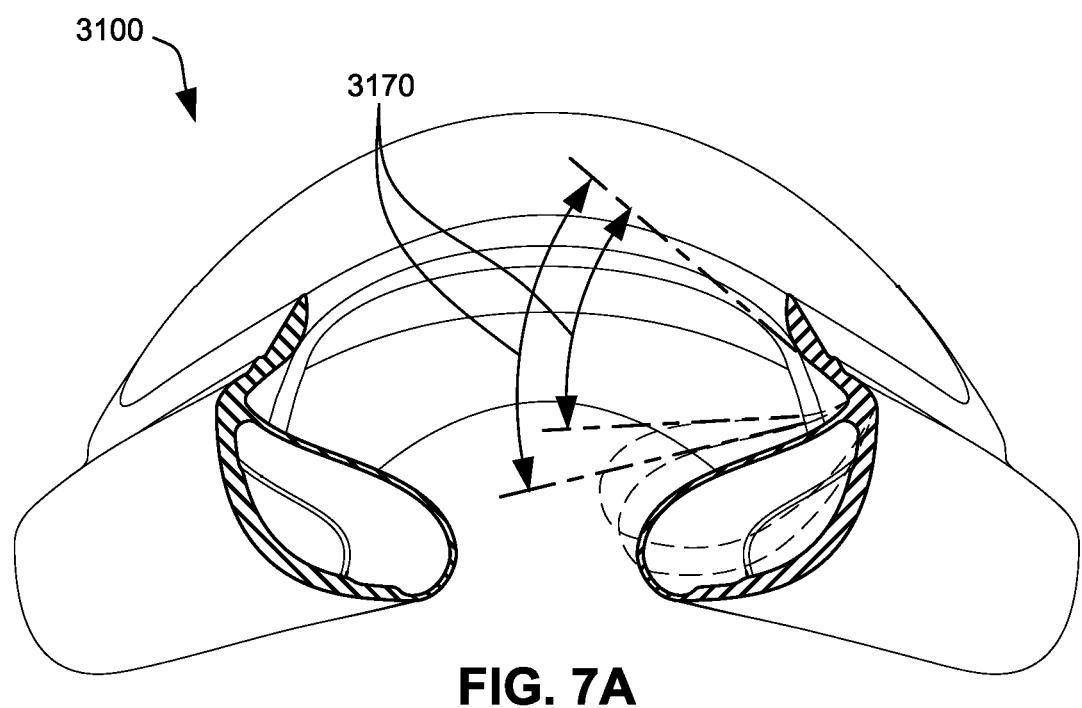

FIG. 7A depicts the same cross-sectional view as FIG. 7, but with an angle of the structure varied.

FIGS. 7B-7I depict mechanical attachments at the cross-sectional view of FIG. 7.

FIG. 8A to 8G depict a cross-sectional views taken along corresponding lines of FIG. 6.

Figure 9:
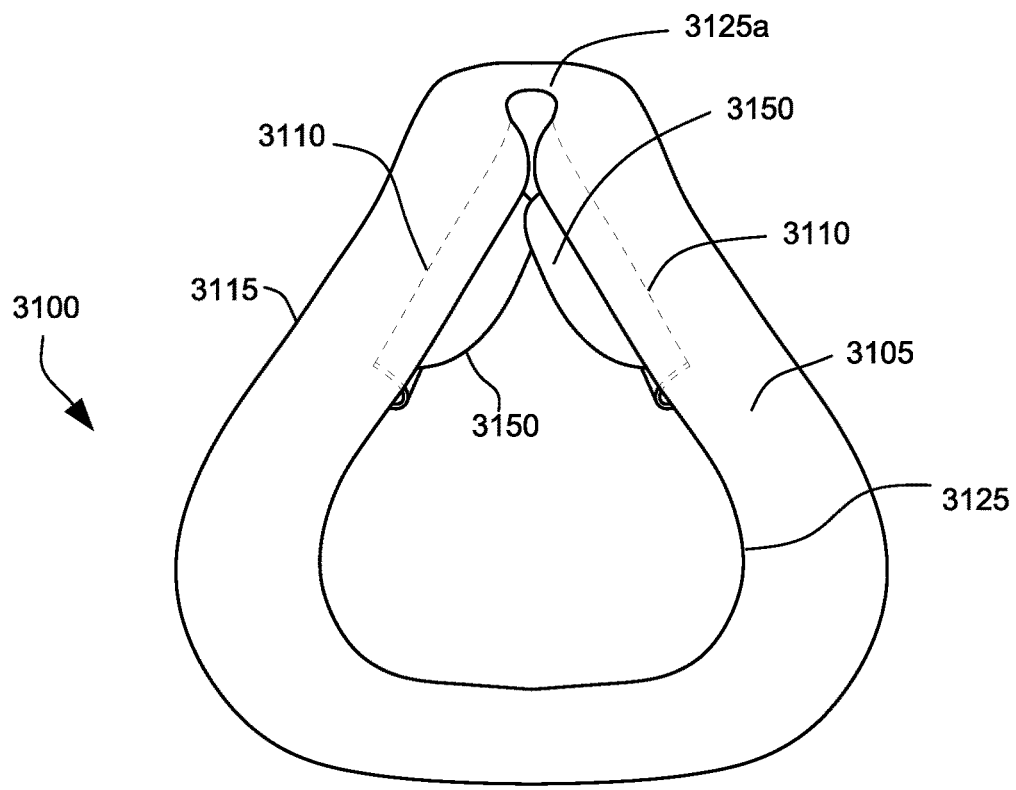

FIG. 9 depicts a plan view of a seal forming structure.

Figure 10:
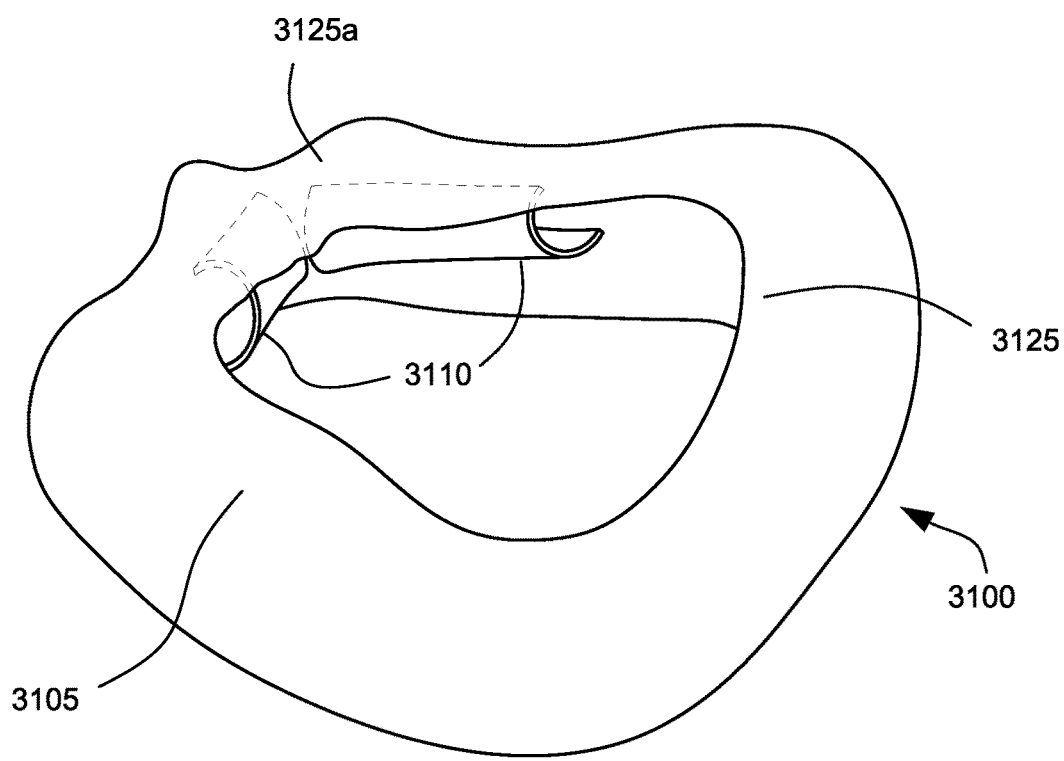

FIG. 10 depicts a perspective view of a seal forming structure.

Figure 11:
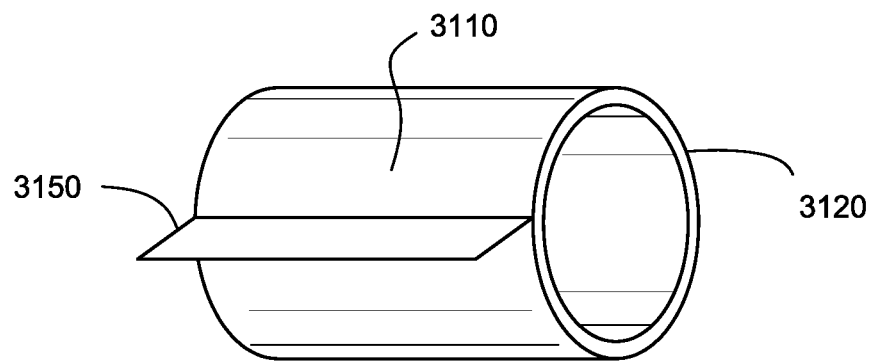

FIG. 11 depicts a simplified representation of a tubular structure and flap.

Figure 12:
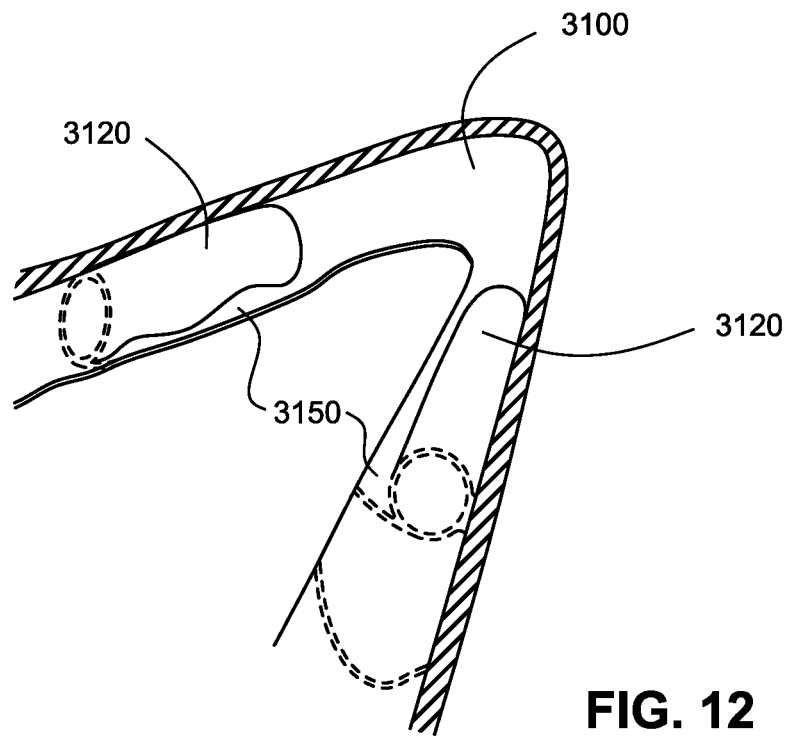

FIG. 12 depicts a simplified representation of a tubular structure and flap attached to a seal forming structure.

Figure 13:
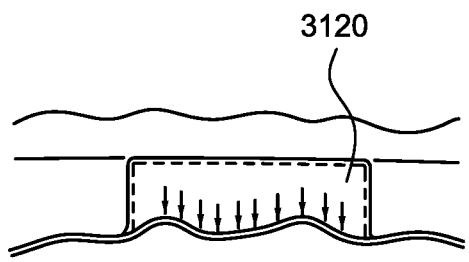

FIG. 13 depicts a simplified representation compliance of a seal forming structure.

Figure 14:
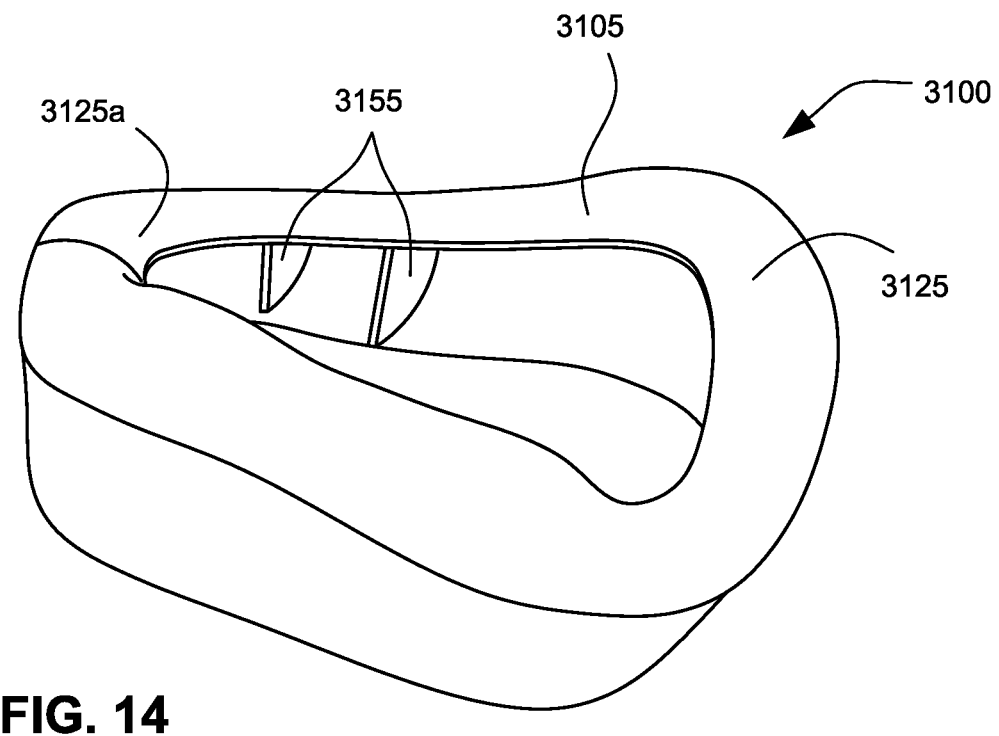

FIG. 14 depicts a perspective view of a seal forming structure.

Figure 15:
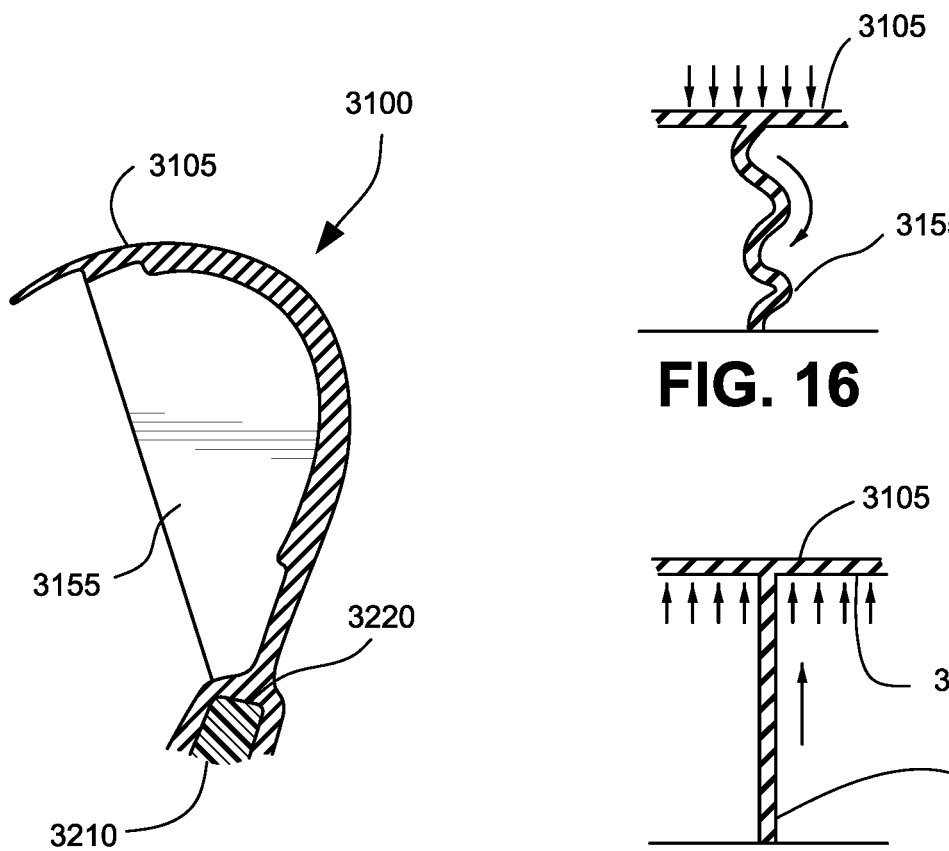

FIG. 15 depicts a cross-sectional view illustrating a rib of a seal forming structure.

Figure 16:
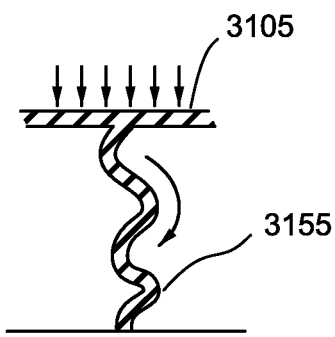

FIG. 16 depicts a cross-sectional view of a rib under compression.

Figure 17:
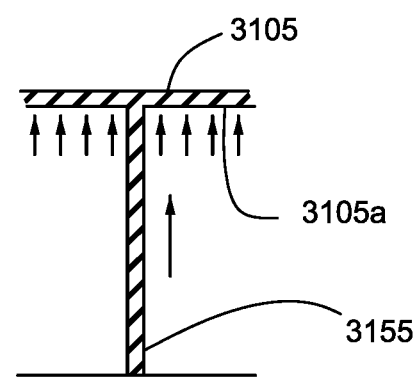

FIG. 17 depicts a cross-sectional view of a rib under tension.

Figure 18:
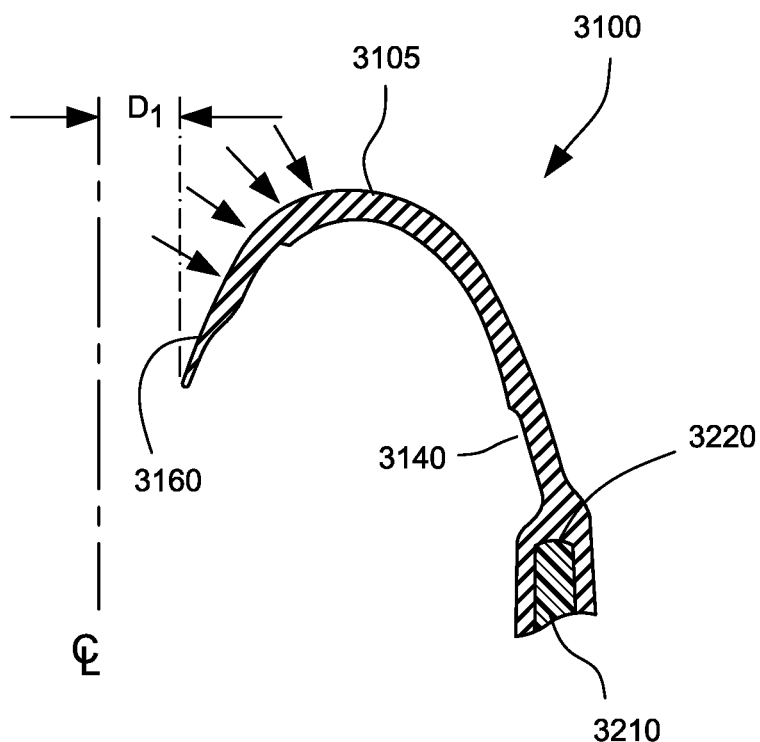
Figure 19:
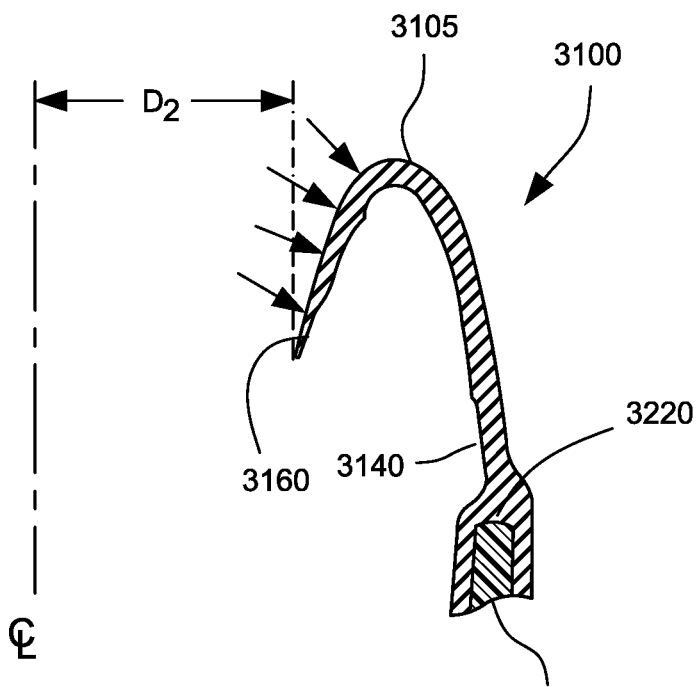

FIGS. 18 and 19 illustrate cross-sections of a seal forming structure.

Figure 20A:
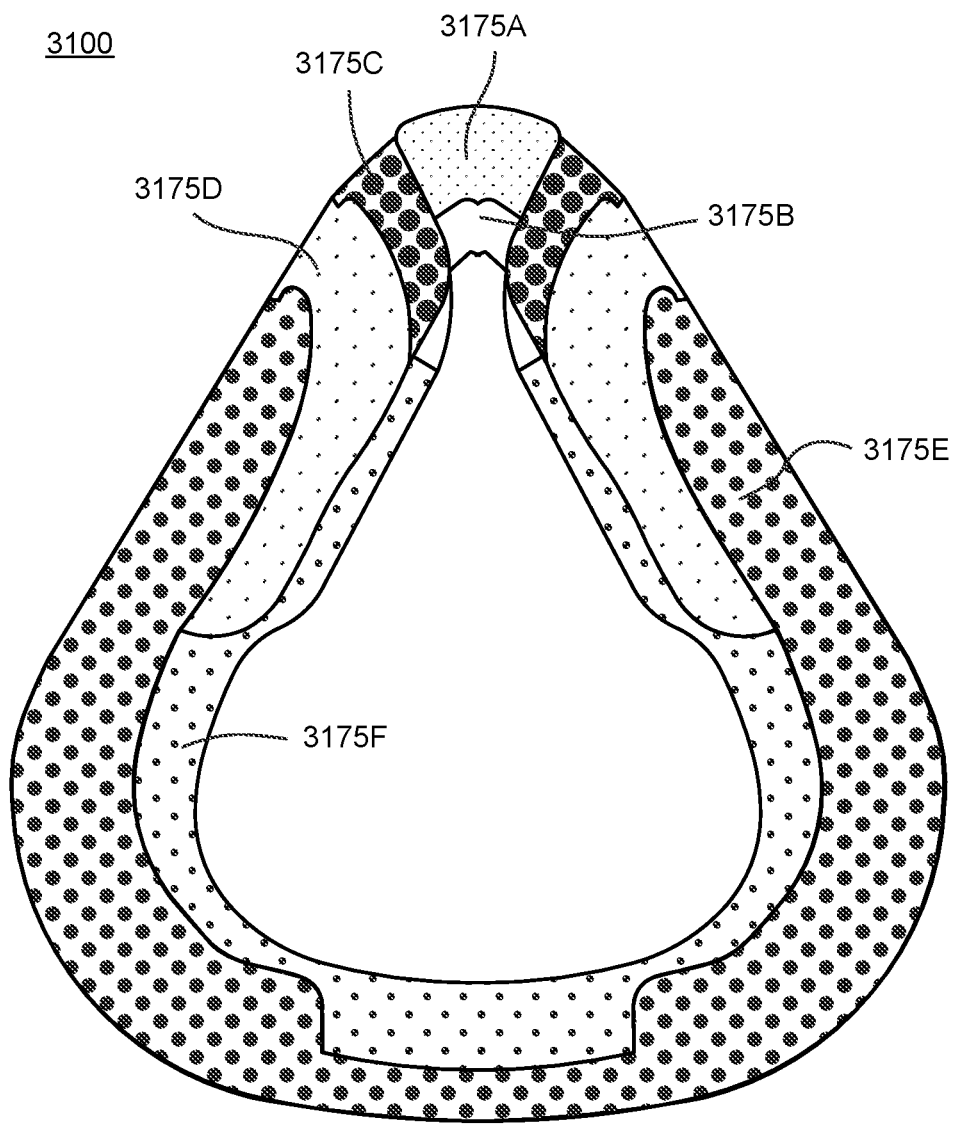

FIG. 20A depicts various regions of a seal forming structure.

Figure 20B:
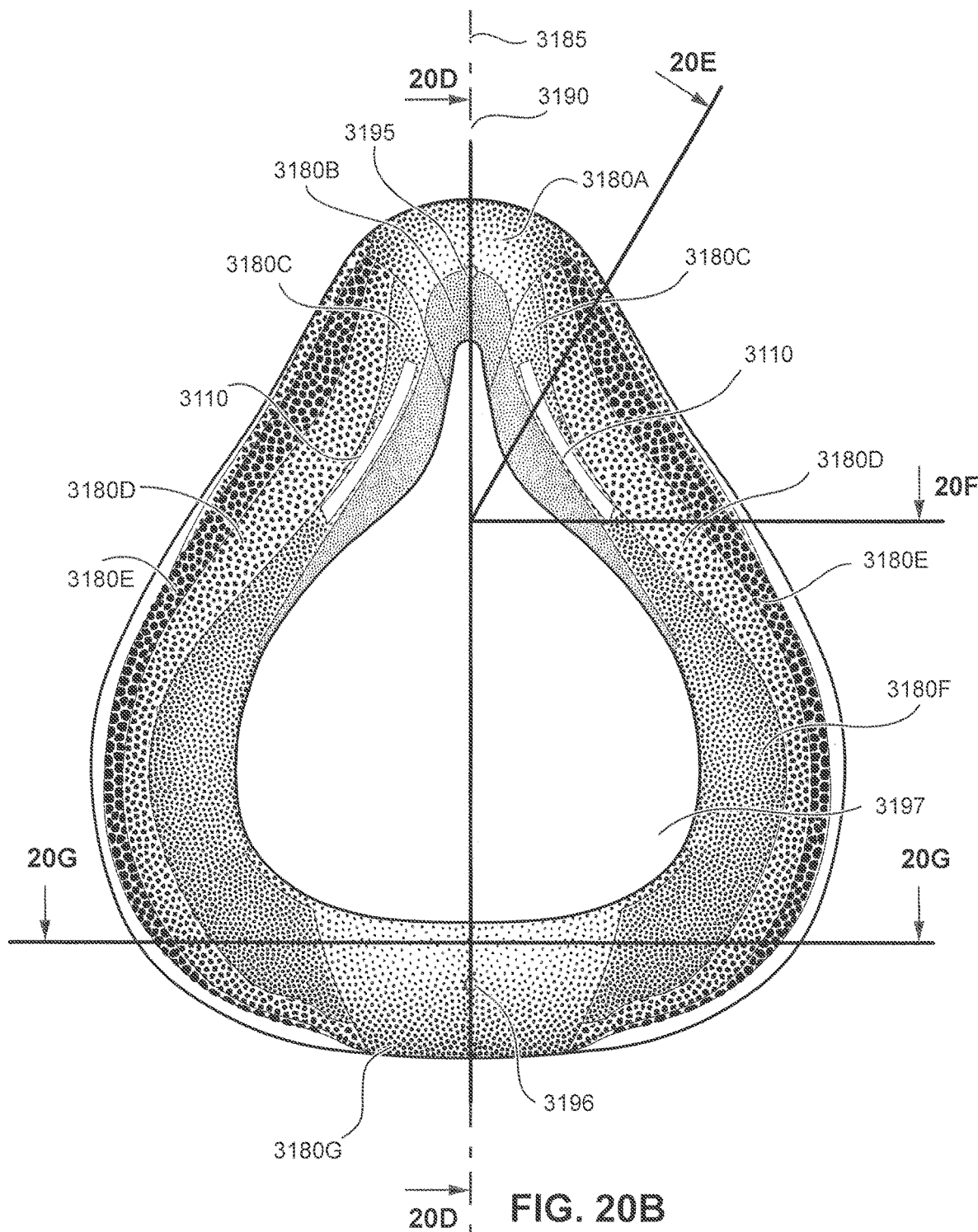

FIG. 20B depicts various regions of another seal forming structure.

Figure 20C:
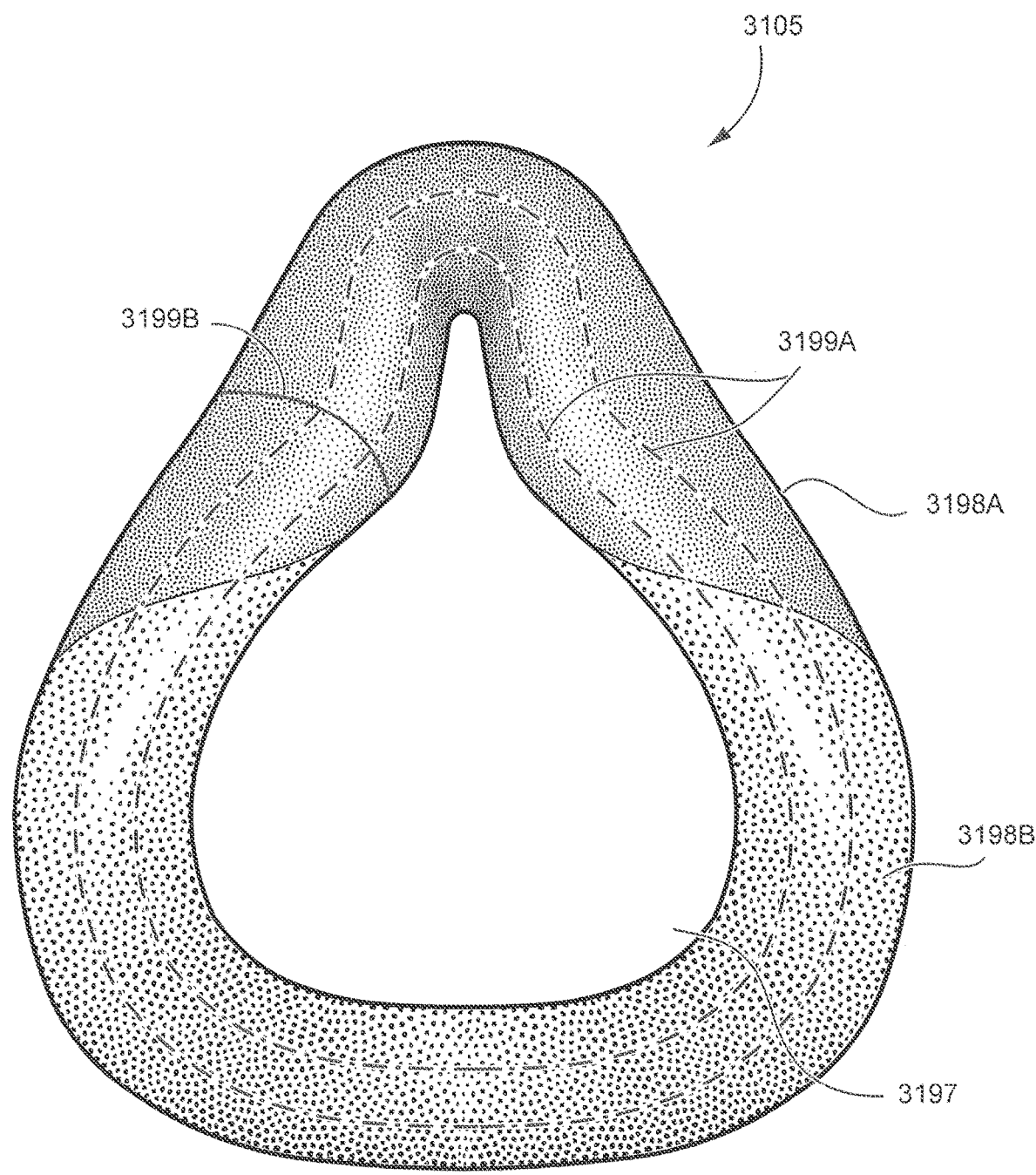
Figure 20D:
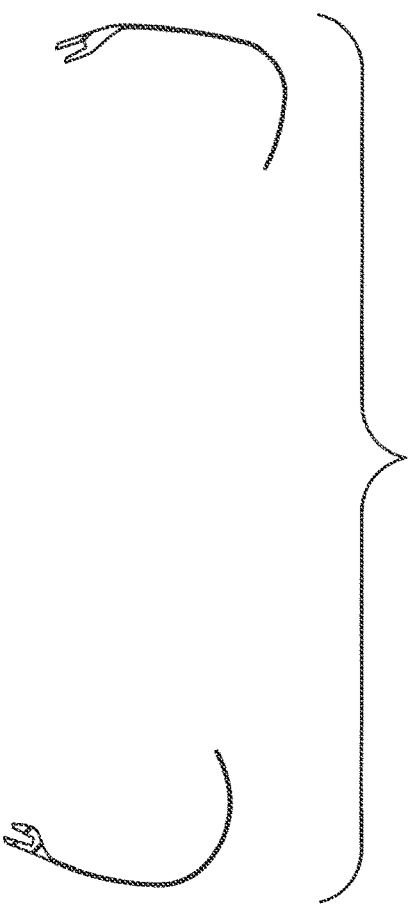
Figure 20E:
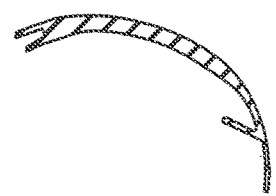
Figure 20F:
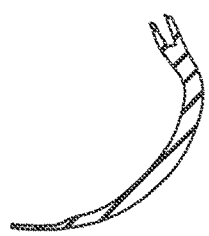
Figure 20G:
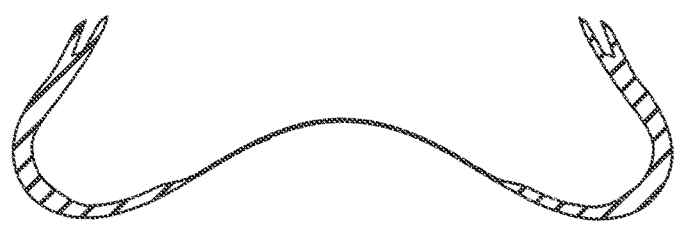

FIG. 20C further depicts the seal forming structure of FIG. 20A.

FIGS. 20D to 20G depict cross-sectional views taken along corresponding lines of FIG. 20B.

Figure 21:
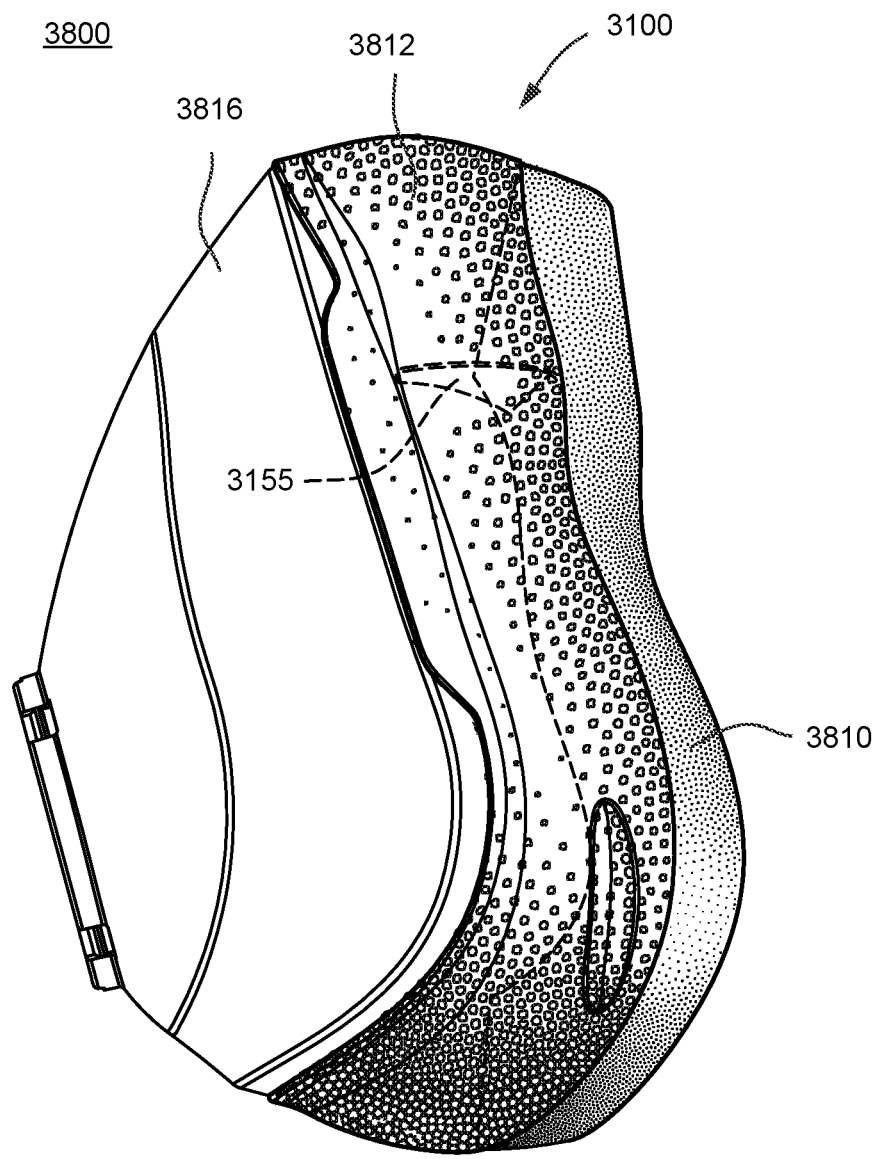

FIG. 21 depicts a seal forming structure attached to a mask shell.

Figure 22:
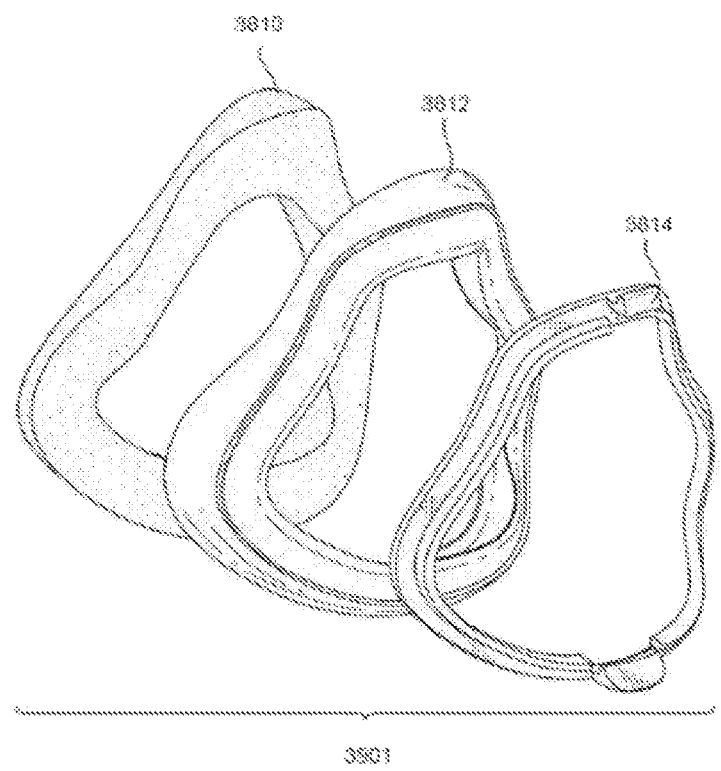

FIG. 22 depicts an exploded view of a seal forming structure and two clips.

Figure 23:
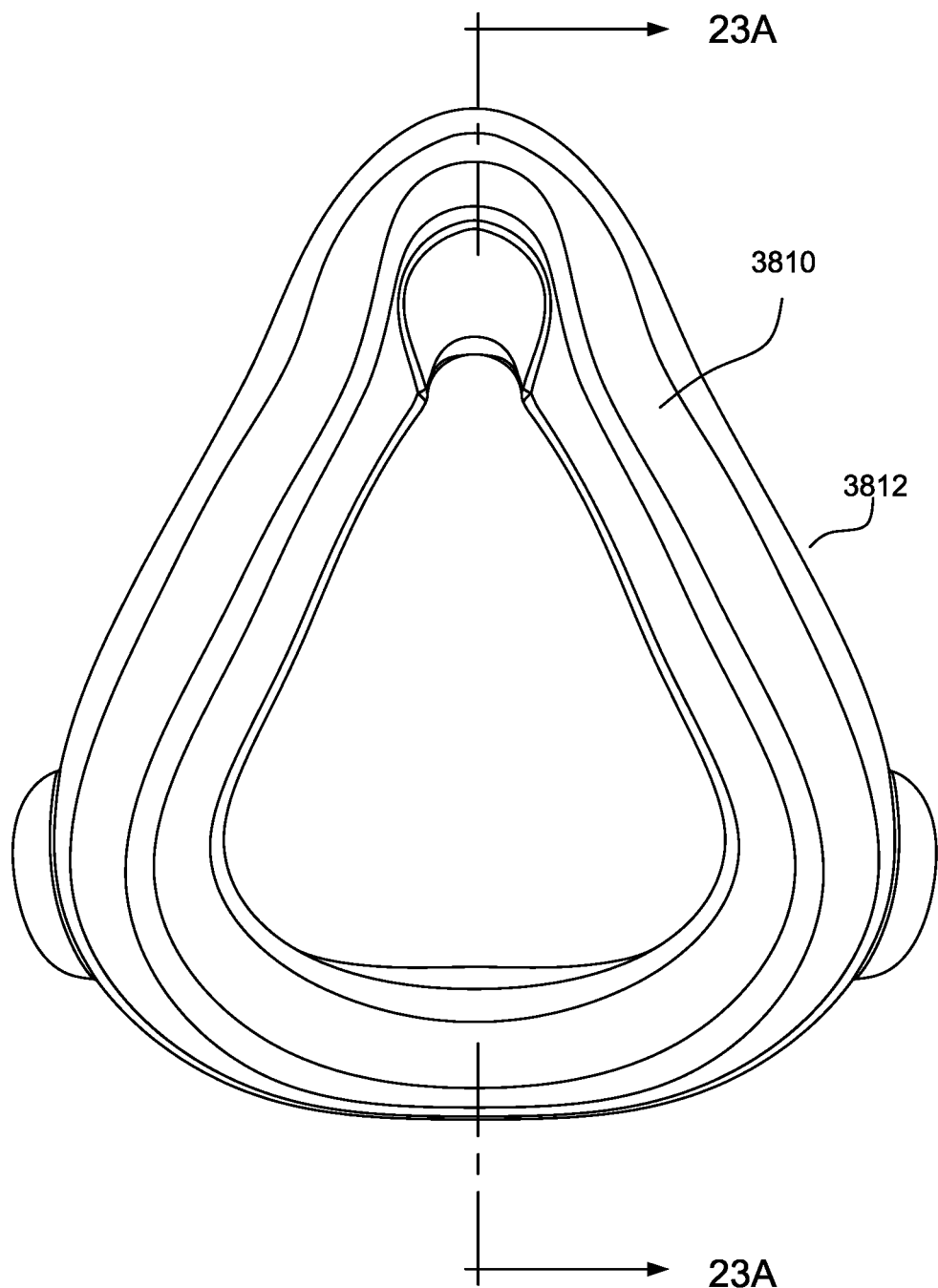

FIG. 23 depicts a view of a cushion and clip.

Figure 23A:
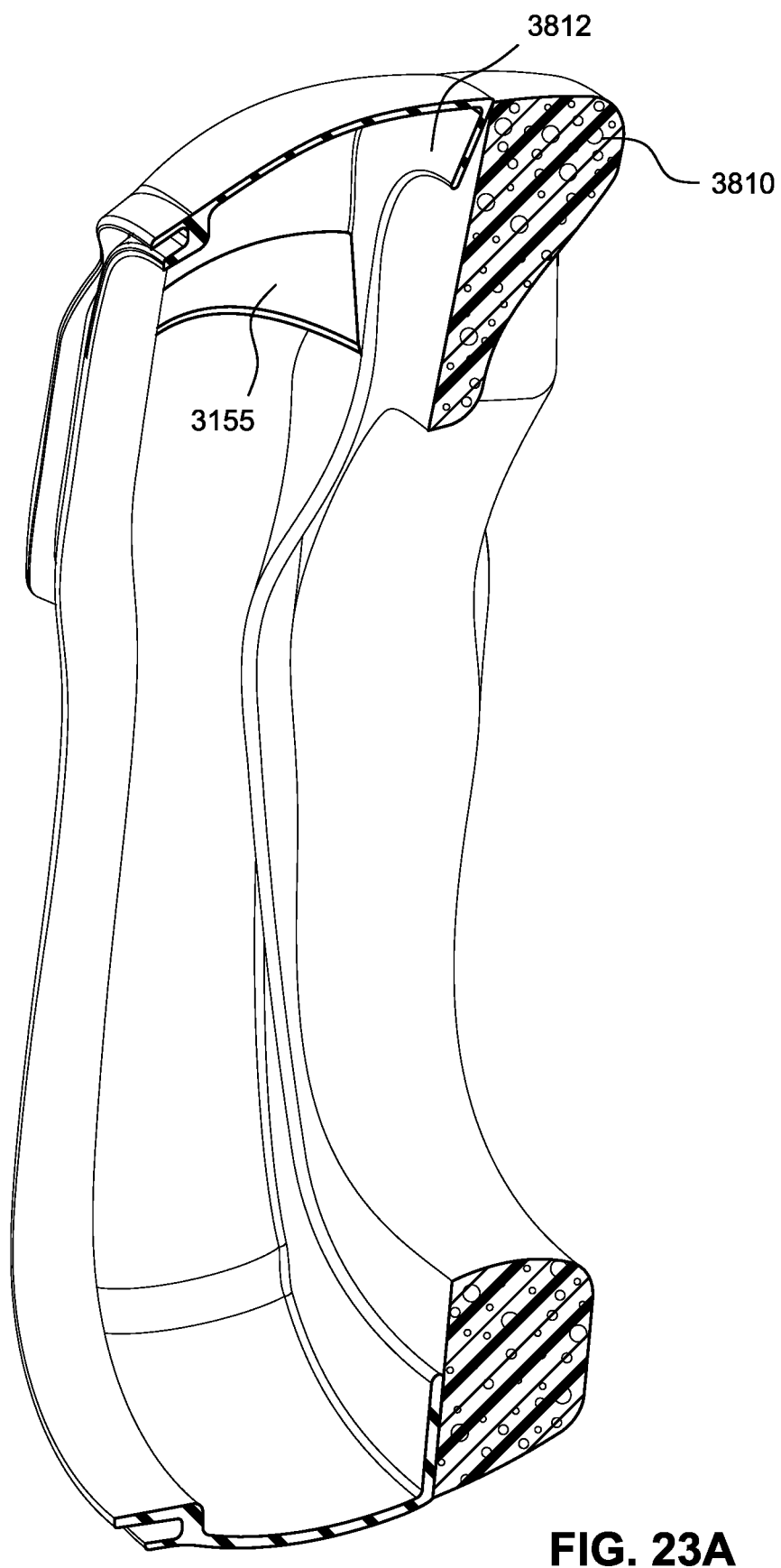

FIG. 23A depicts a cross-sectional view of FIG. 23 taken along line 23A-23A.

Figure 24:
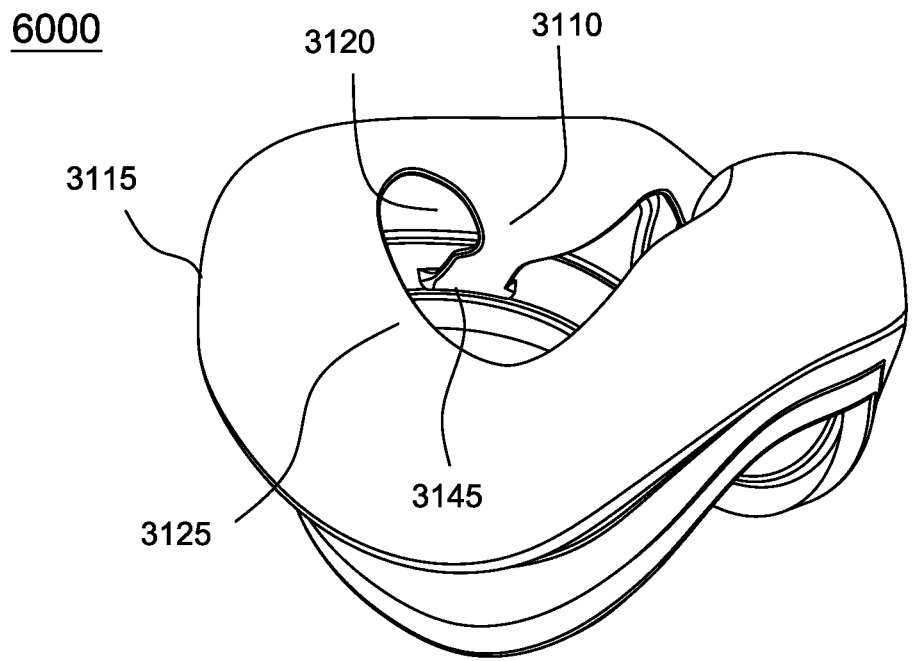

FIG. 24 depicts a perspective view of a seal forming structure.

Figure 25A:
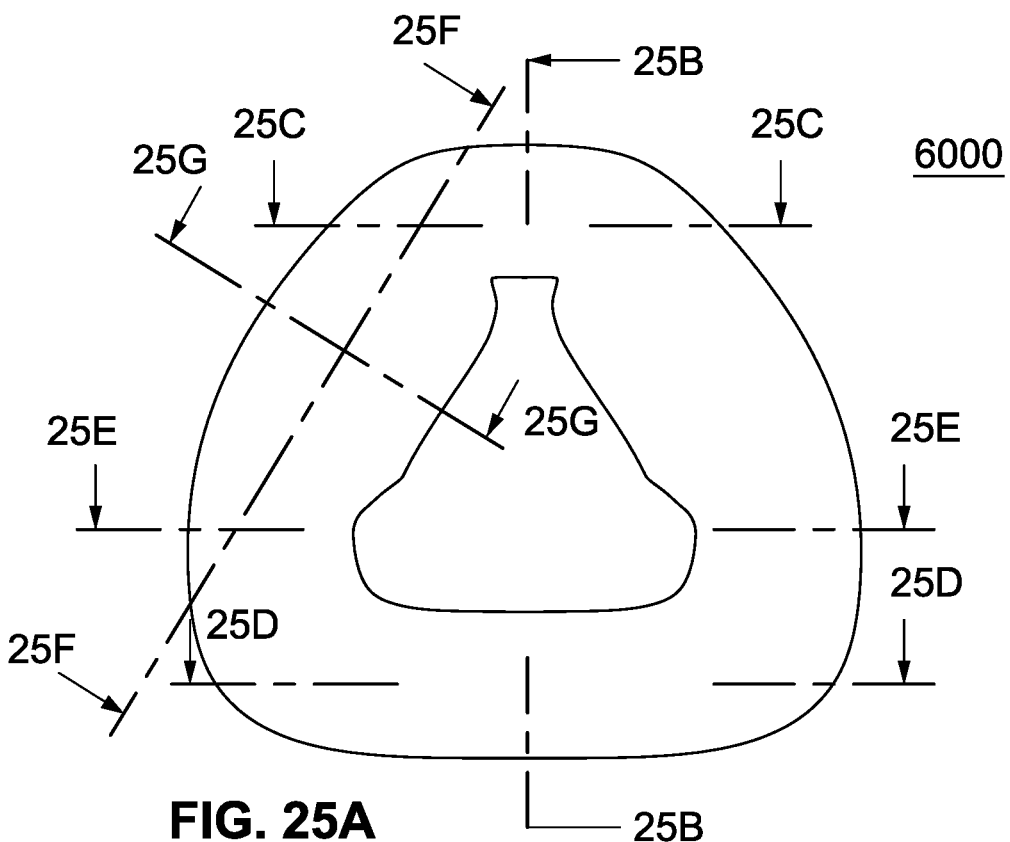
Figure 25B:
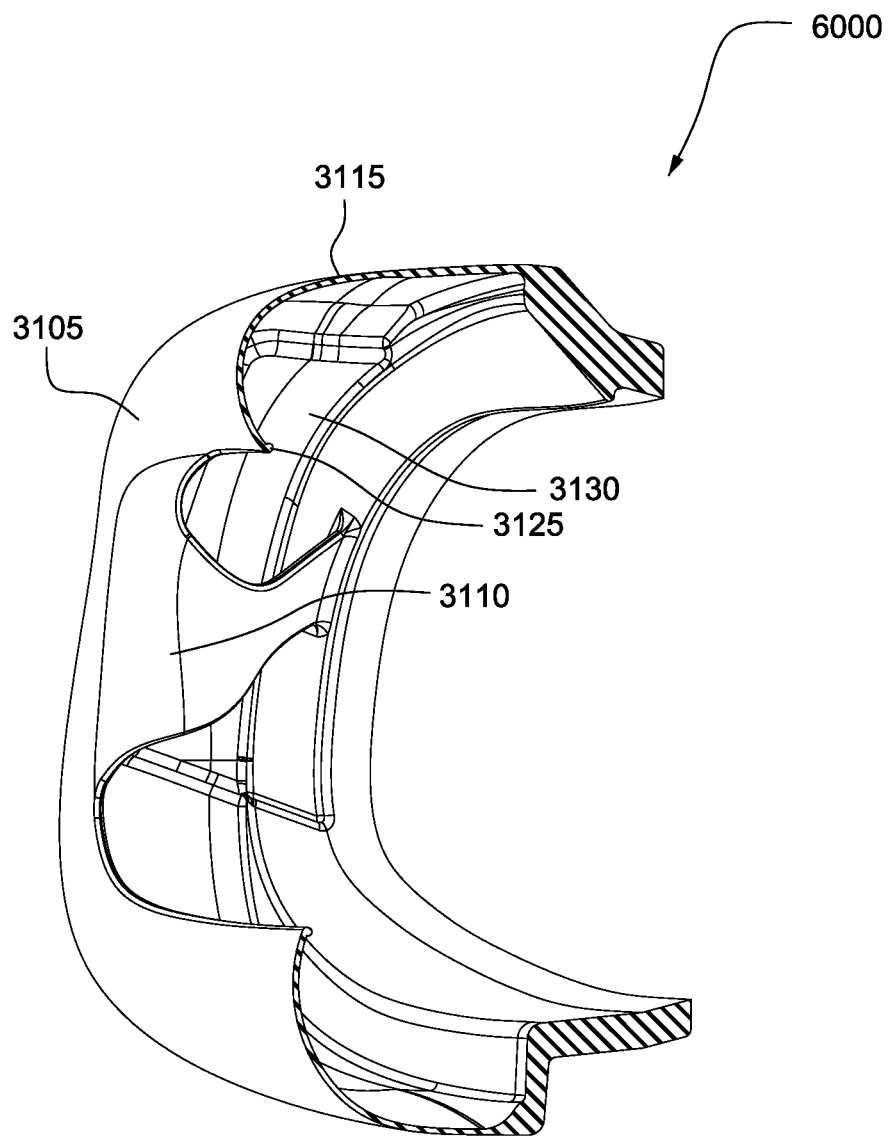
Figure 25C:
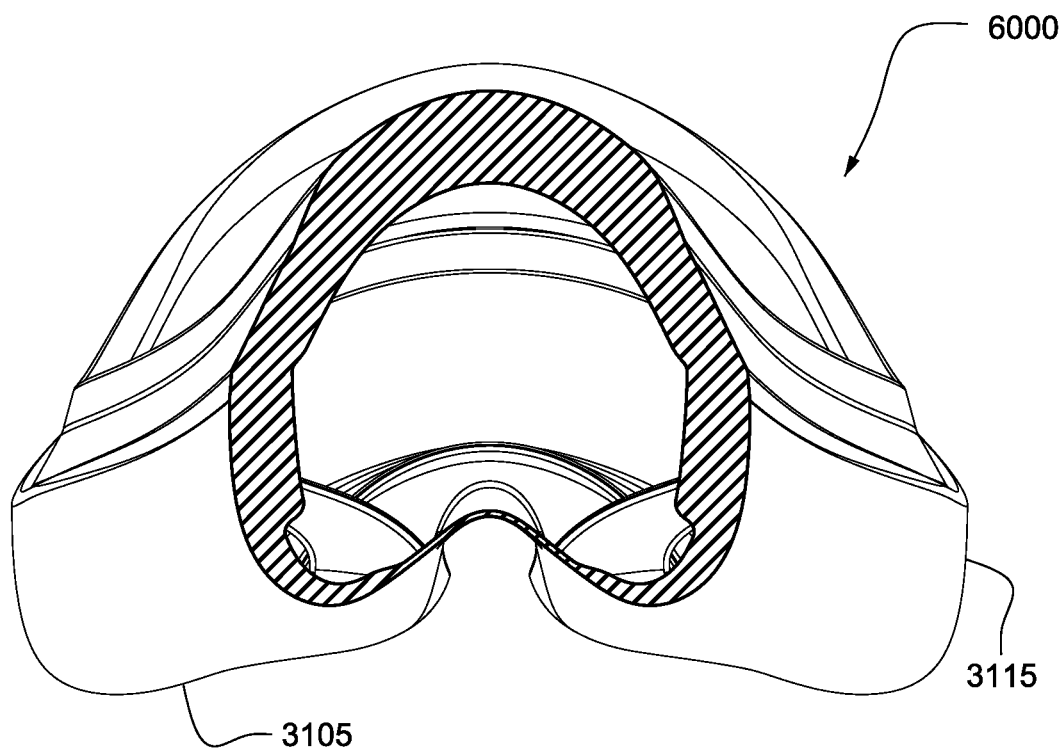
Figure 25D:
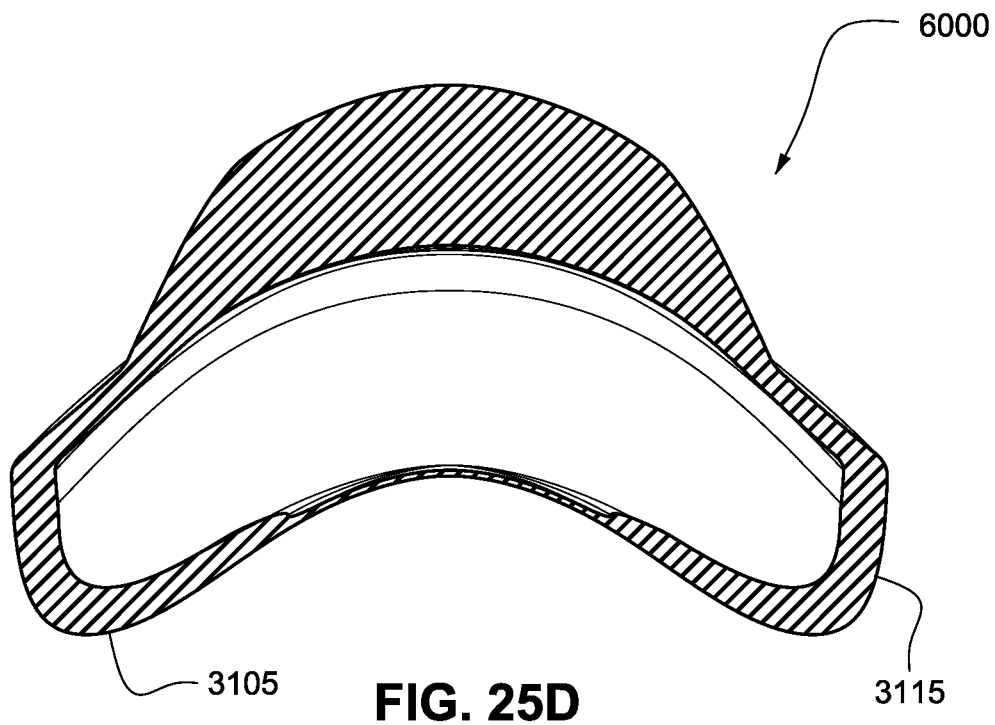
Figure 25E:
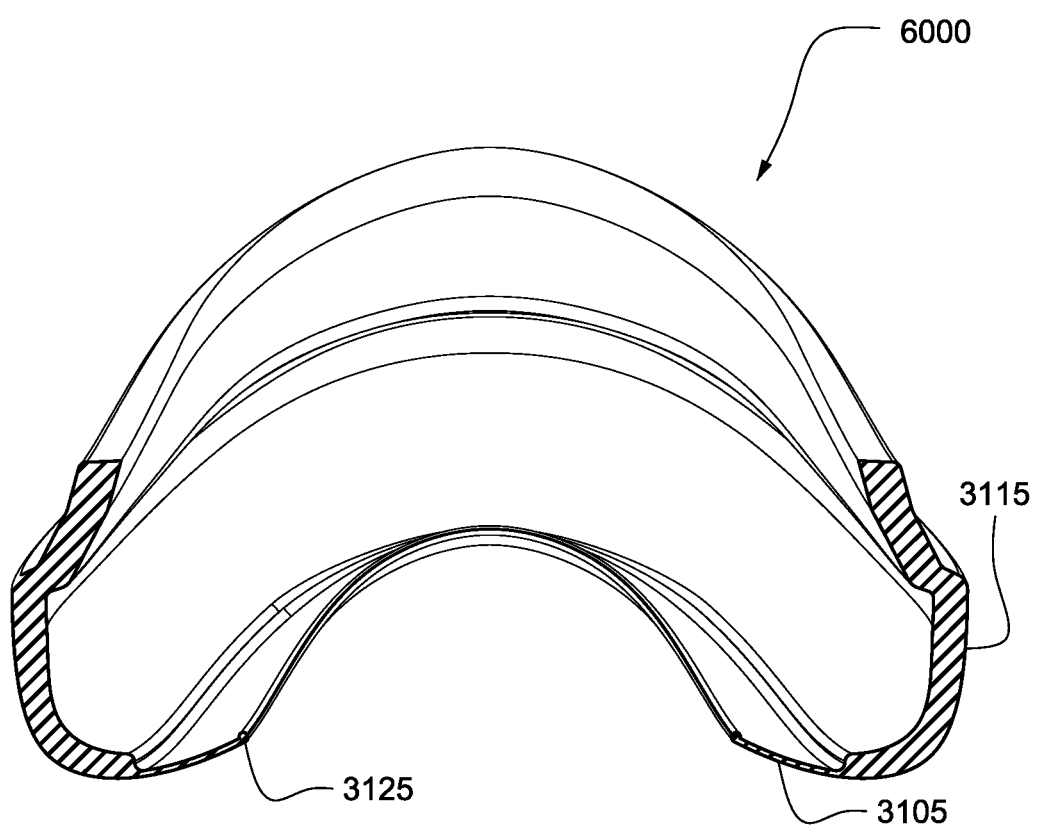
Figure 25F:
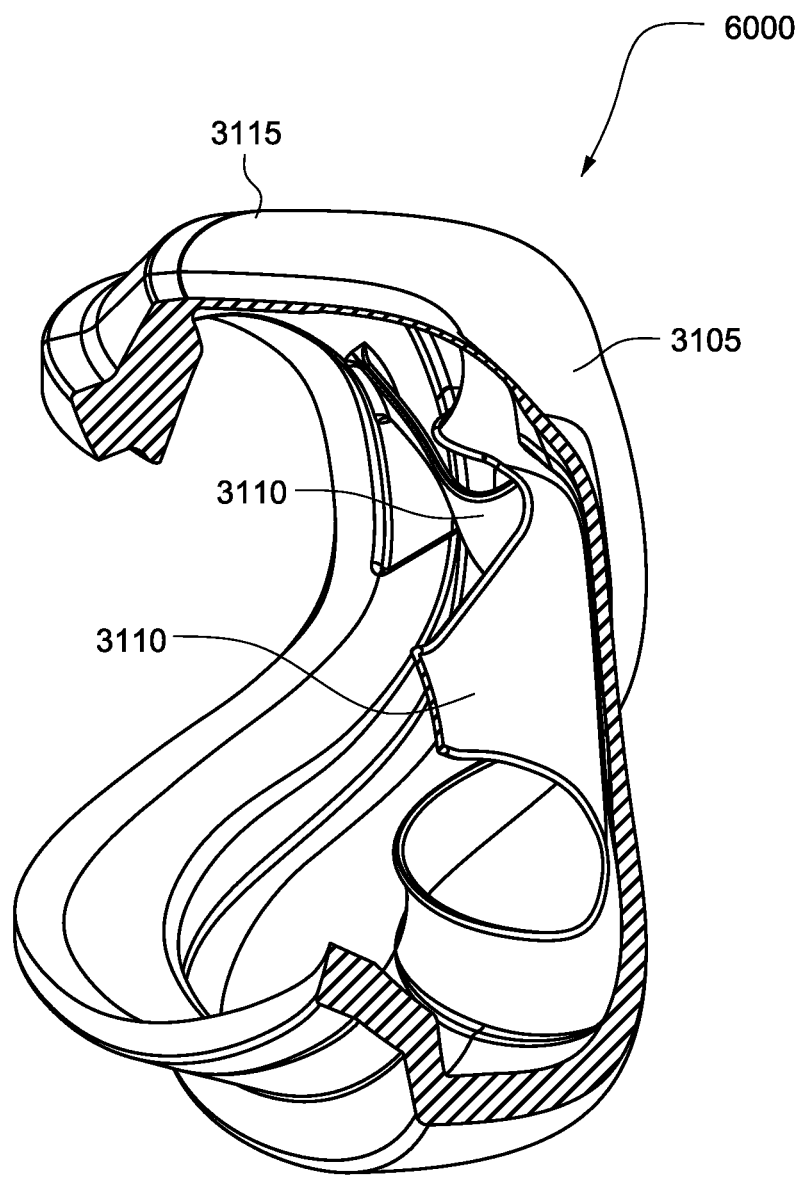
Figure 25G:
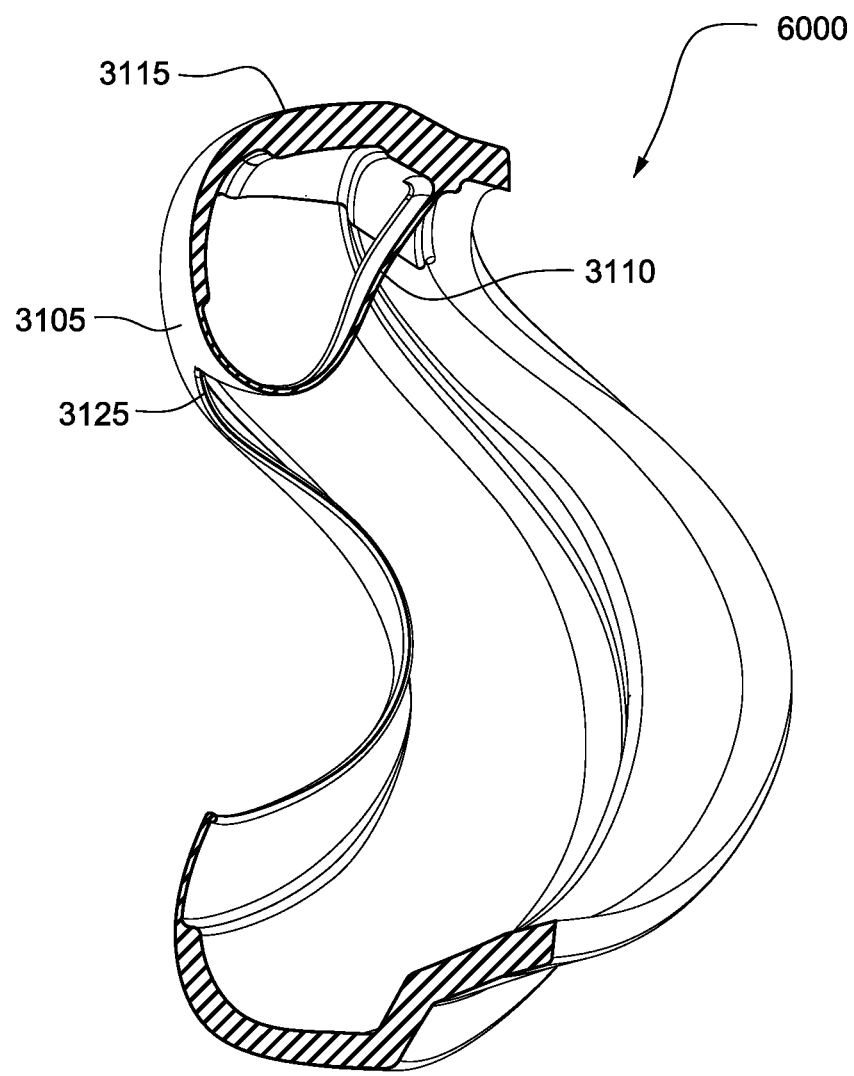

FIG. 25A depicts a front view of the seal forming structure of FIG. 24.

FIGS. 25B-25G depict various cross-sections taken along corresponding lines in FIG. 25A.

Figure 26:
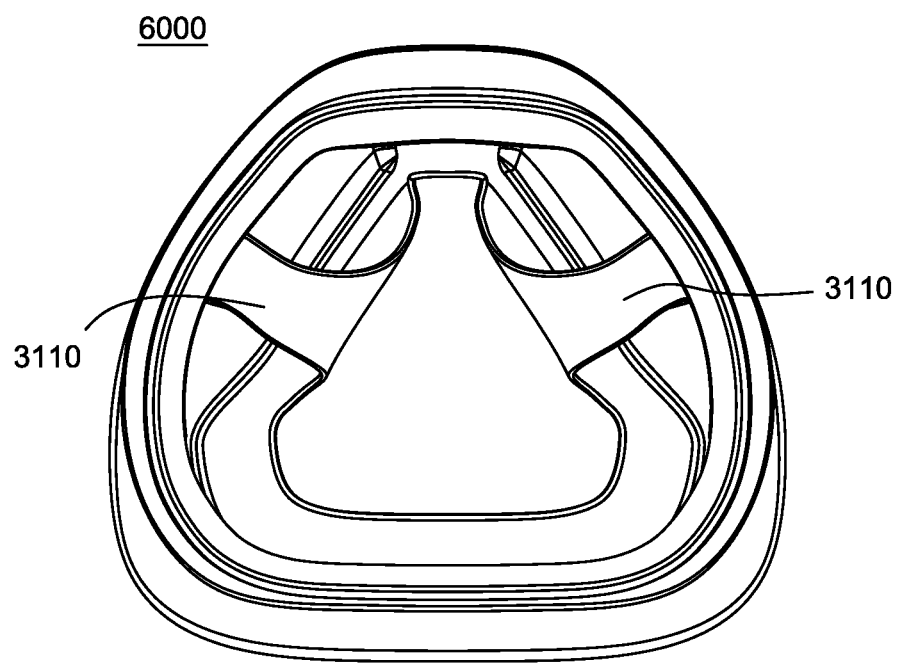

FIG. 26 depicts a rear view of the seal forming structure of FIG. 24.

Figure 27:
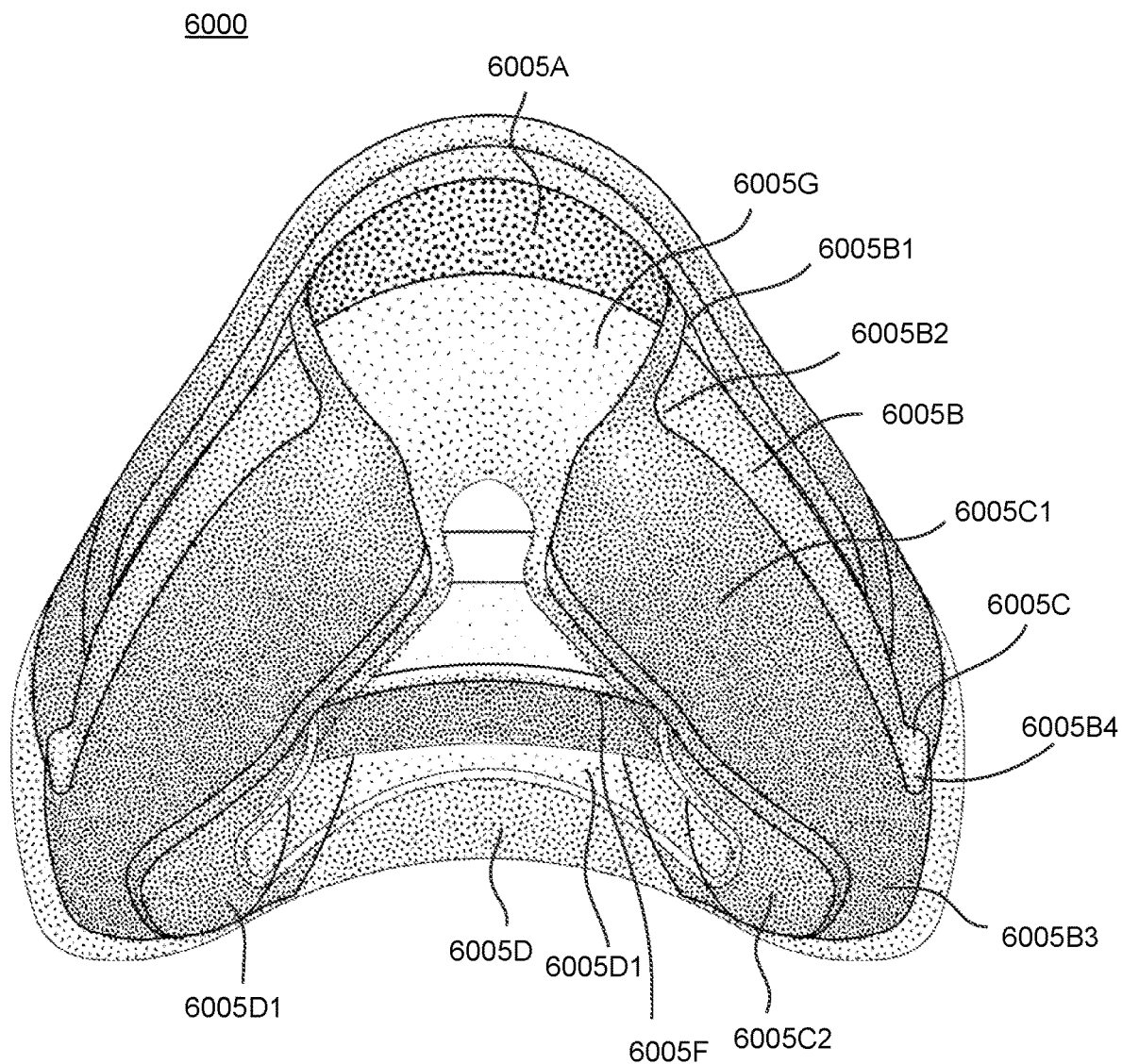

FIG. 27 depicts various regions of the seal forming structure of FIG. 24.

Figure 28A:
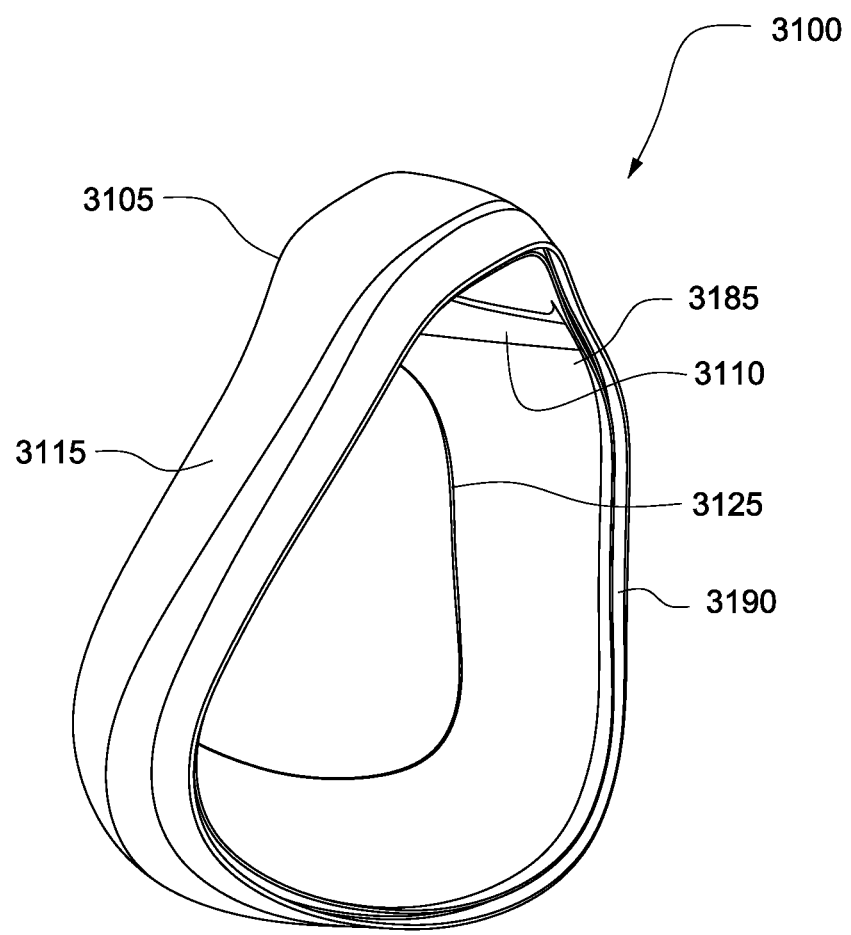

FIG. 28A is a top perspective view of a seal-forming structure for a full-face patient interface according to an example of the present technology.

Figure 28B:
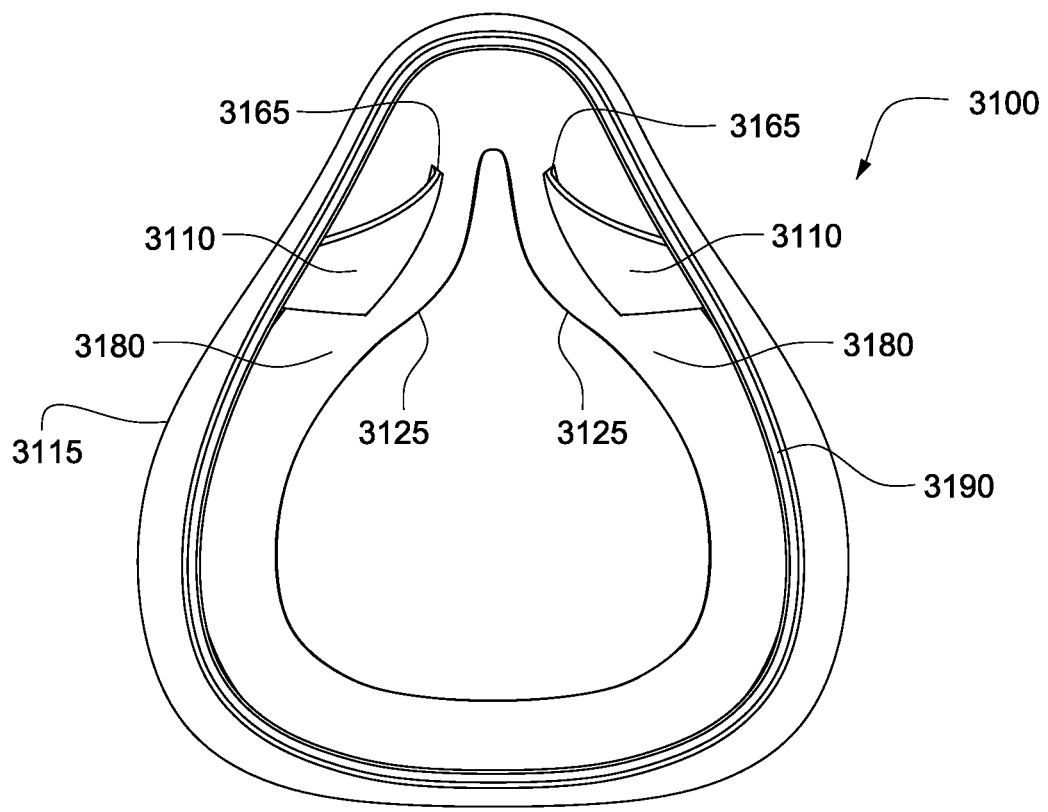

FIG. 28B is a front view of a seal-forming structure for a full-face patient interface according to an example of the present technology.

Figure 28C:
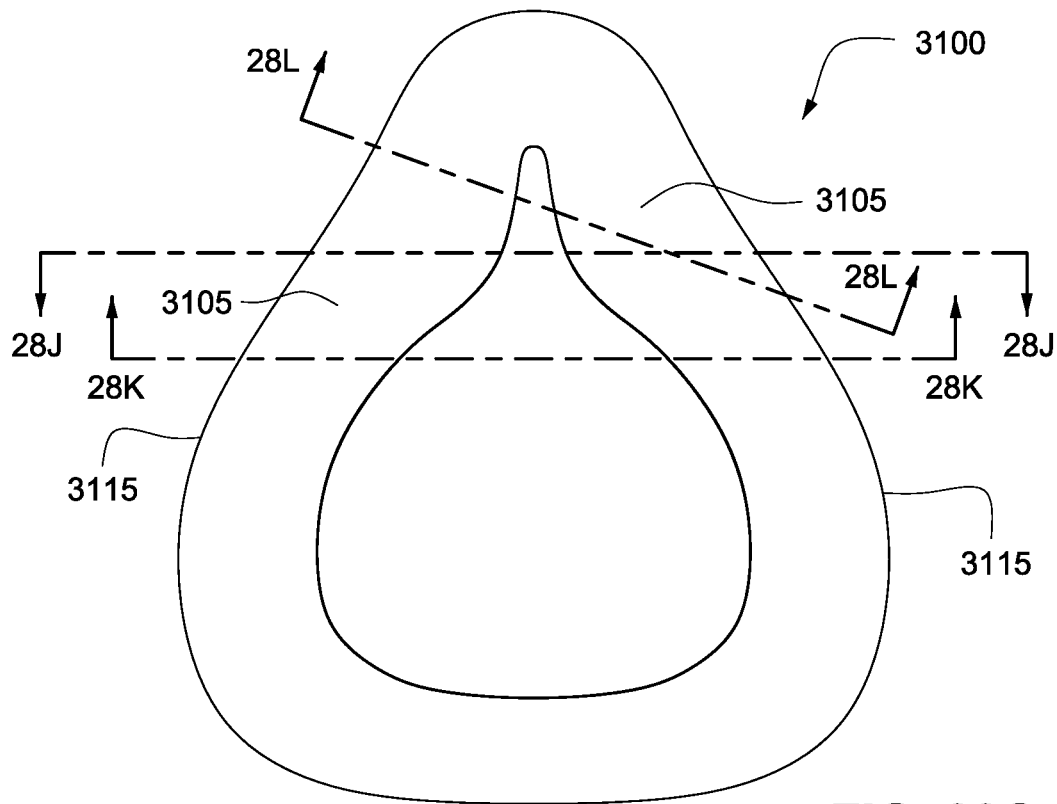

FIG. 28C is a rear view of a seal-forming structure for a full-face patient interface according to an example of the present technology.

Figure 28D:
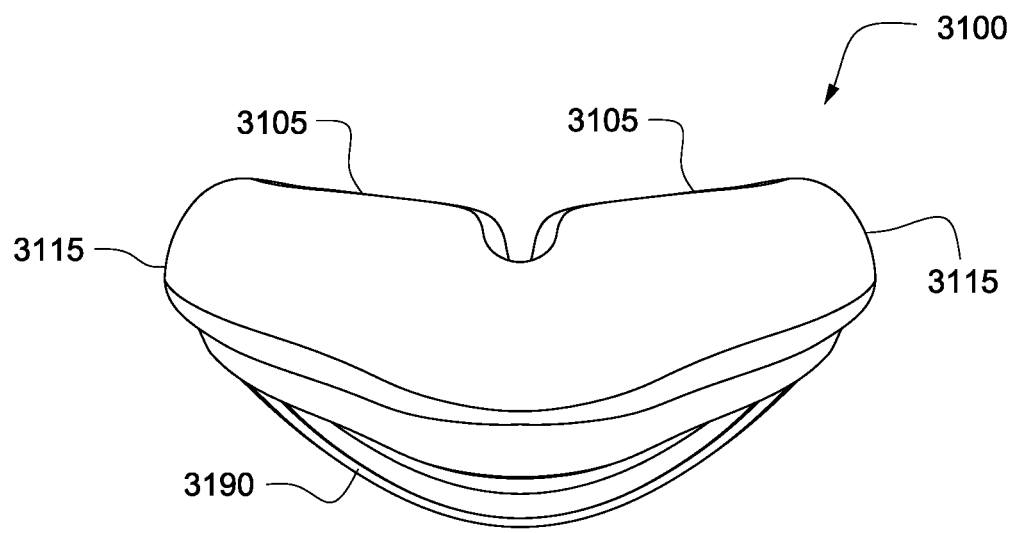

FIG. 28D is a top view of a seal-forming structure for a full-face patient interface according to an example of the present technology.

Figure 28E:
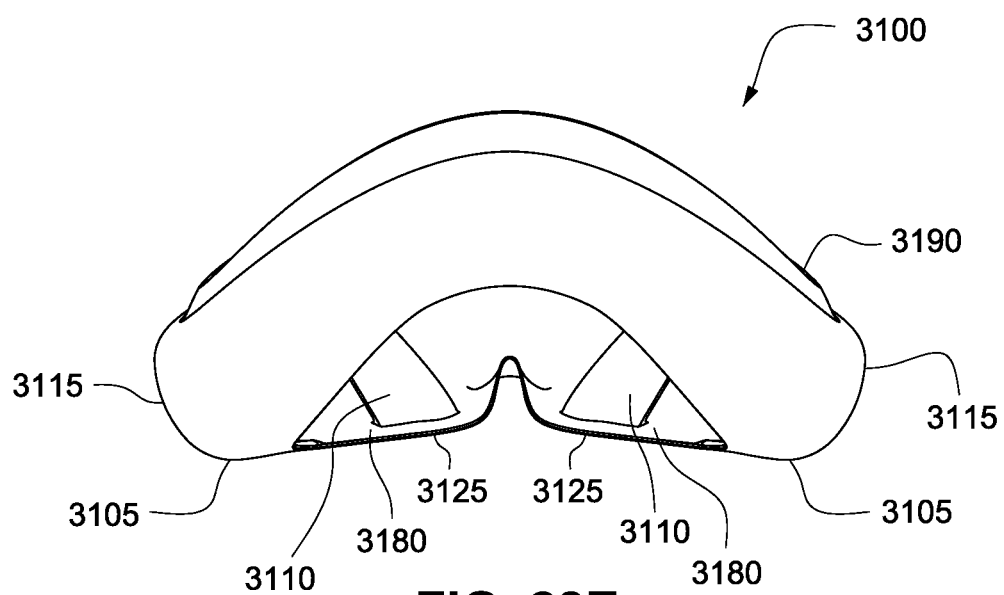

FIG. 28E is a bottom view of a seal-forming structure for a full-face patient interface according to an example of the present technology.

Figure 28F:
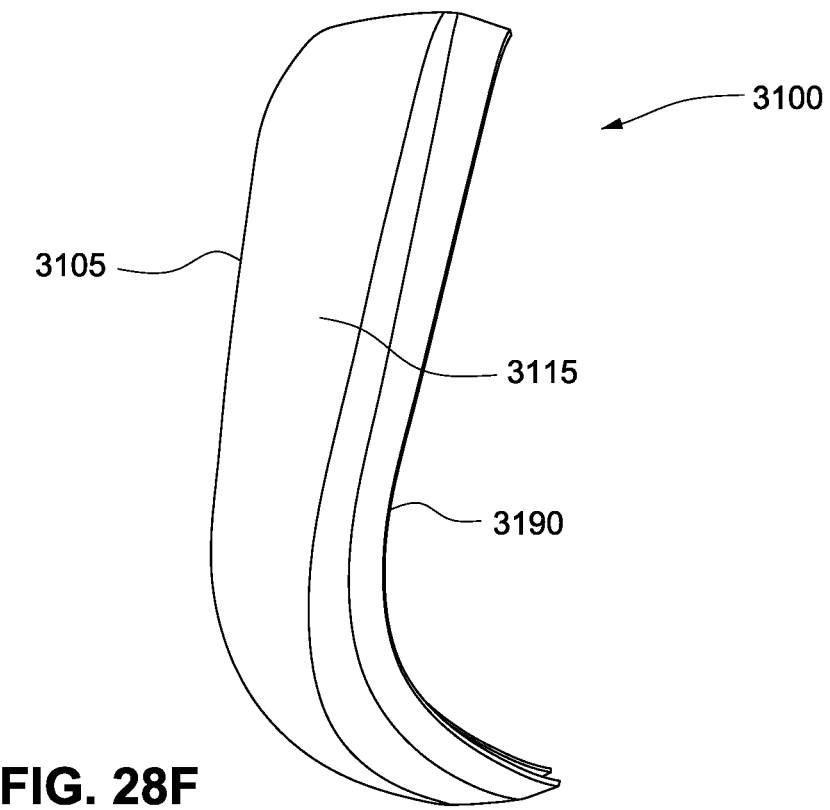

FIG. 28F is a side view of a seal-forming structure for a full-face patient interface according to an example of the present technology.

Figure 28G:
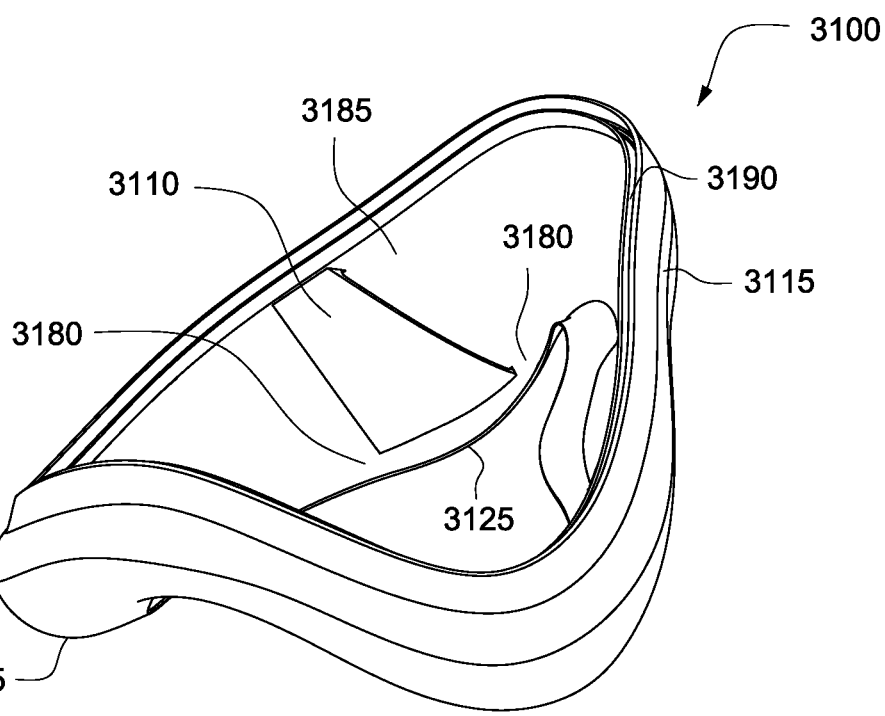

FIG. 28G is a bottom perspective view of a seal-forming structure for a full-face patient interface according to an example of the present technology.

Figure 28H:
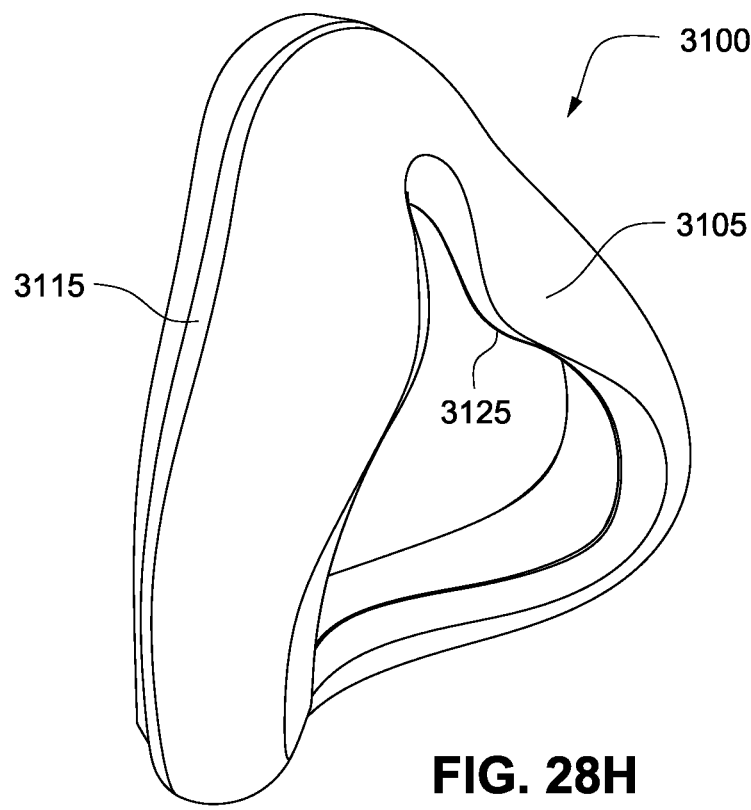

FIG. 28H is another top perspective view of a seal-forming structure for a full-face patient interface according to an example of the present technology.

Figure 28I:
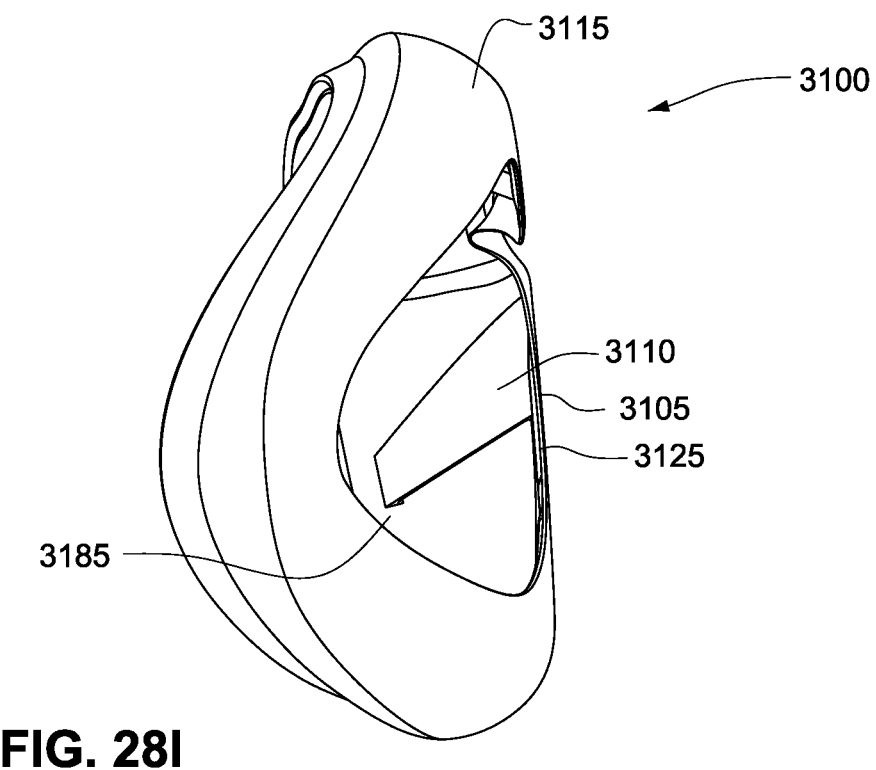

FIG. 28I is another bottom view of a seal-forming structure for a full-face patient interface according to an example of the present technology.

Figure 28J:
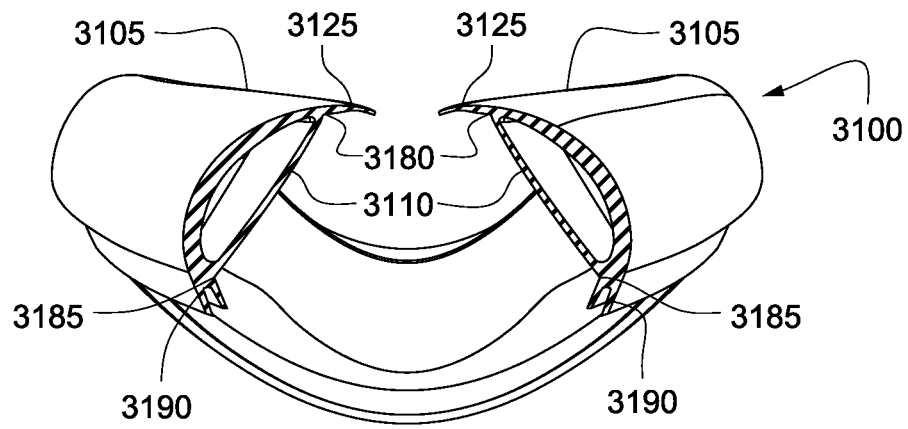

FIG. 28J is a cross-sectional view of a seal-forming structure for a full-face patient interface taken through line 28J-28J of FIG. 28B according to an example of the present technology.

Figure 28K:
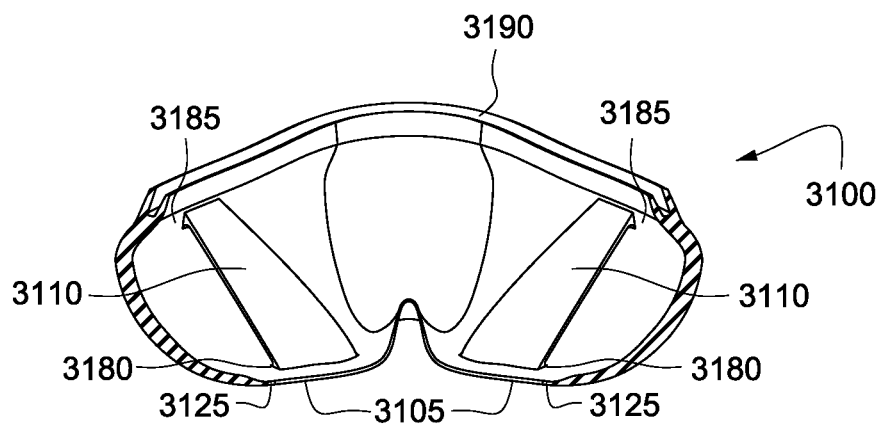

FIG. 28K is a cross-sectional view of a seal-forming structure for a full-face patient interface taken through line 28K-28K of FIG. 28B according to an example of the present technology.

Figure 28L:
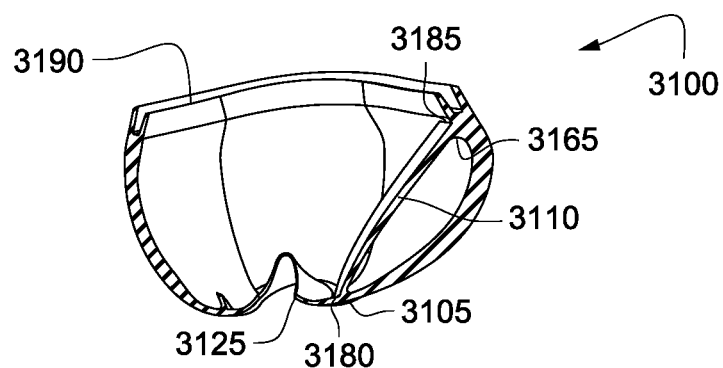

FIG. 28L is a cross-sectional view of a seal-forming structure for a full-face patient interface taken through line 28L-28L of FIG. 28B according to an example of the present technology.

Figure 28M:
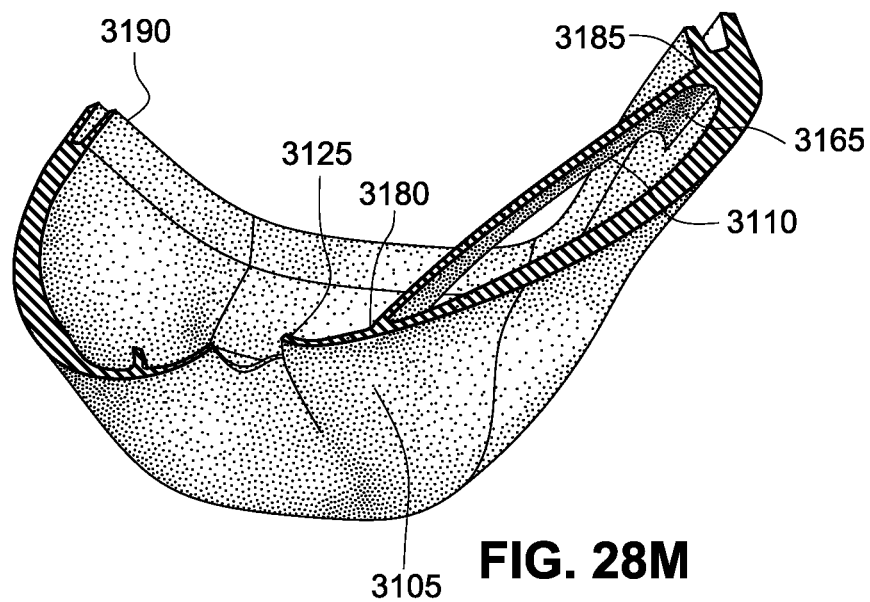

FIG. 28M is a perspective view of a seal-forming structure for a full-face patient interface shown in FIG. 28L.

Figure 29A:
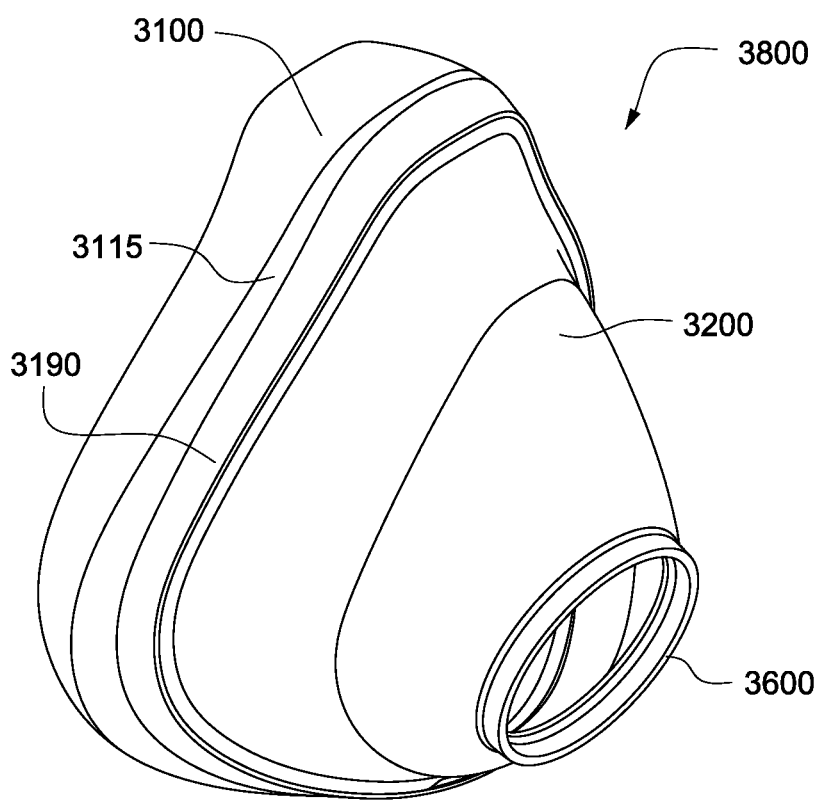

FIG. 29A is a top perspective view of an assembly of a seal-forming structure and a plenum chamber for a full-face patient interface according to an example of the present technology.

Figure 29B:
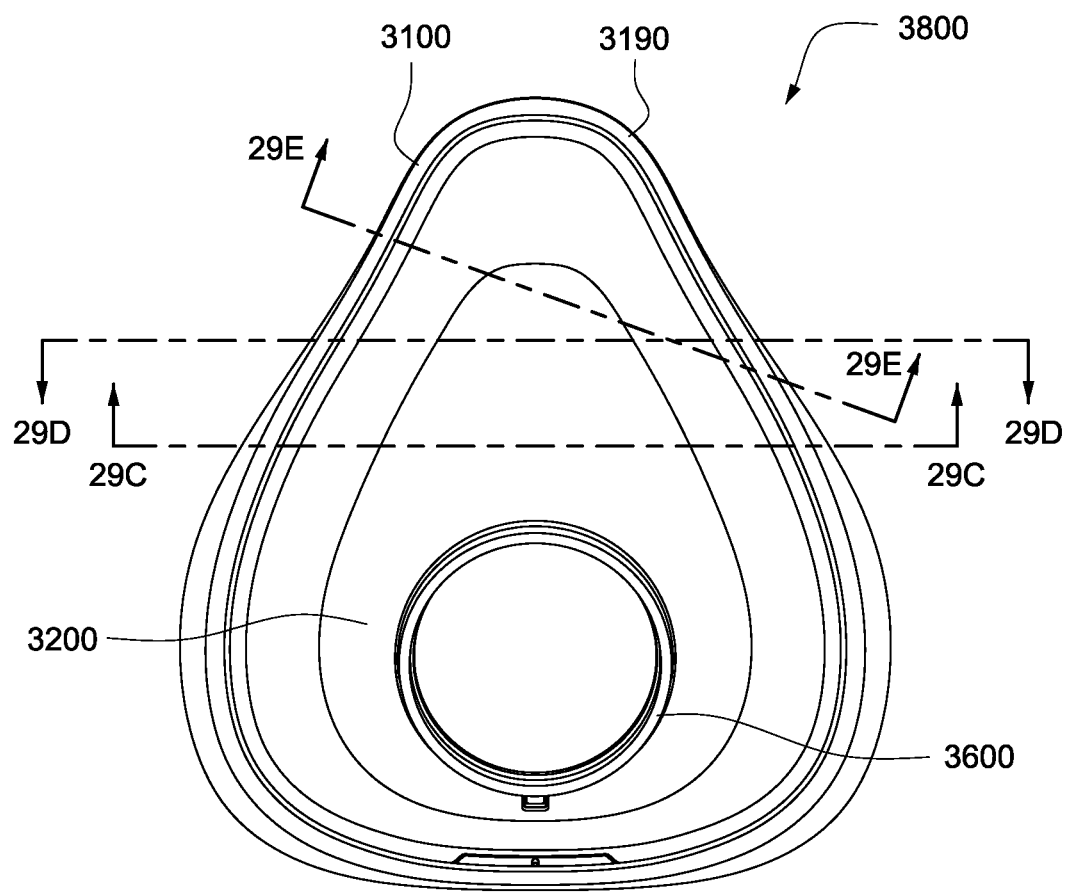

FIG. 29B is a front perspective view of an assembly of a seal-forming structure and a plenum chamber for a full-face patient interface according to an example of the present technology.

Figure 29C:
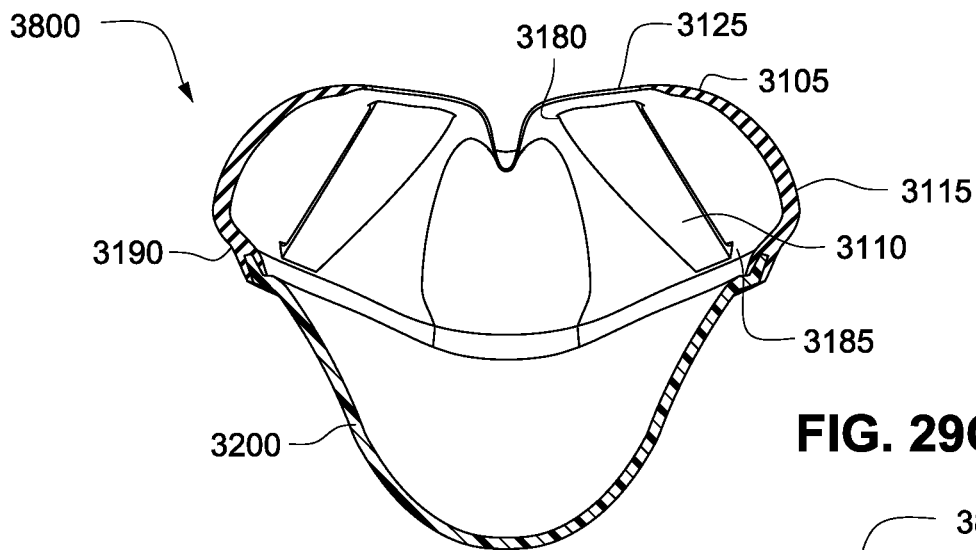

FIG. 29C is a cross-sectional view of an assembly of a seal-forming structure and a plenum chamber for a full-face patient interface taken through line 29C-29C of FIG. 29B according to an example of the present technology.

Figure 29D:
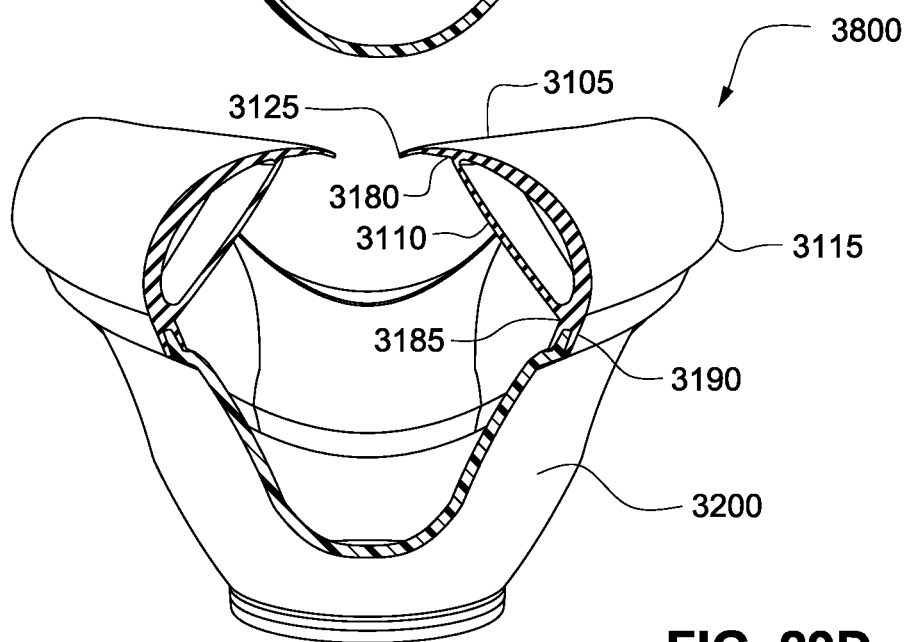

FIG. 29D is a cross-sectional view of an assembly of a seal-forming structure and a plenum chamber for a full-face patient interface taken through line 29D-29D of FIG. 29B according to an example of the present technology.

Figure 29E:
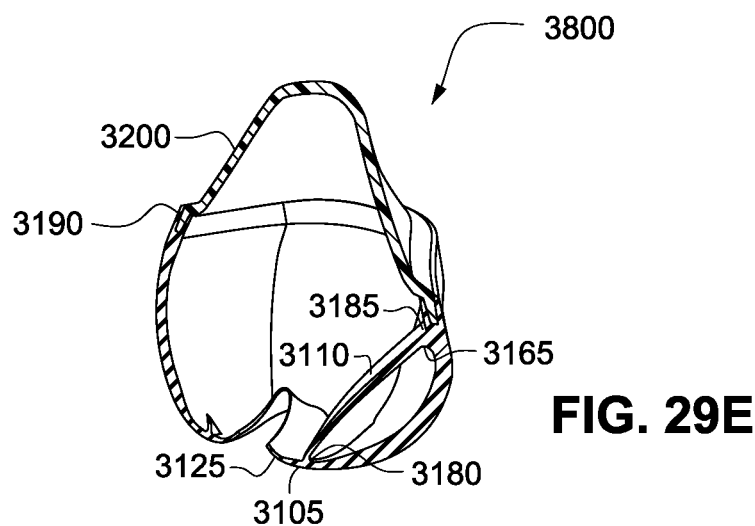

FIG. 29E is a cross-sectional view of an assembly of a seal-forming structure and a plenum chamber for a full-face patient interface taken through line 29E-29E of FIG. 29B according to an example of the present technology.

Figure 30A:
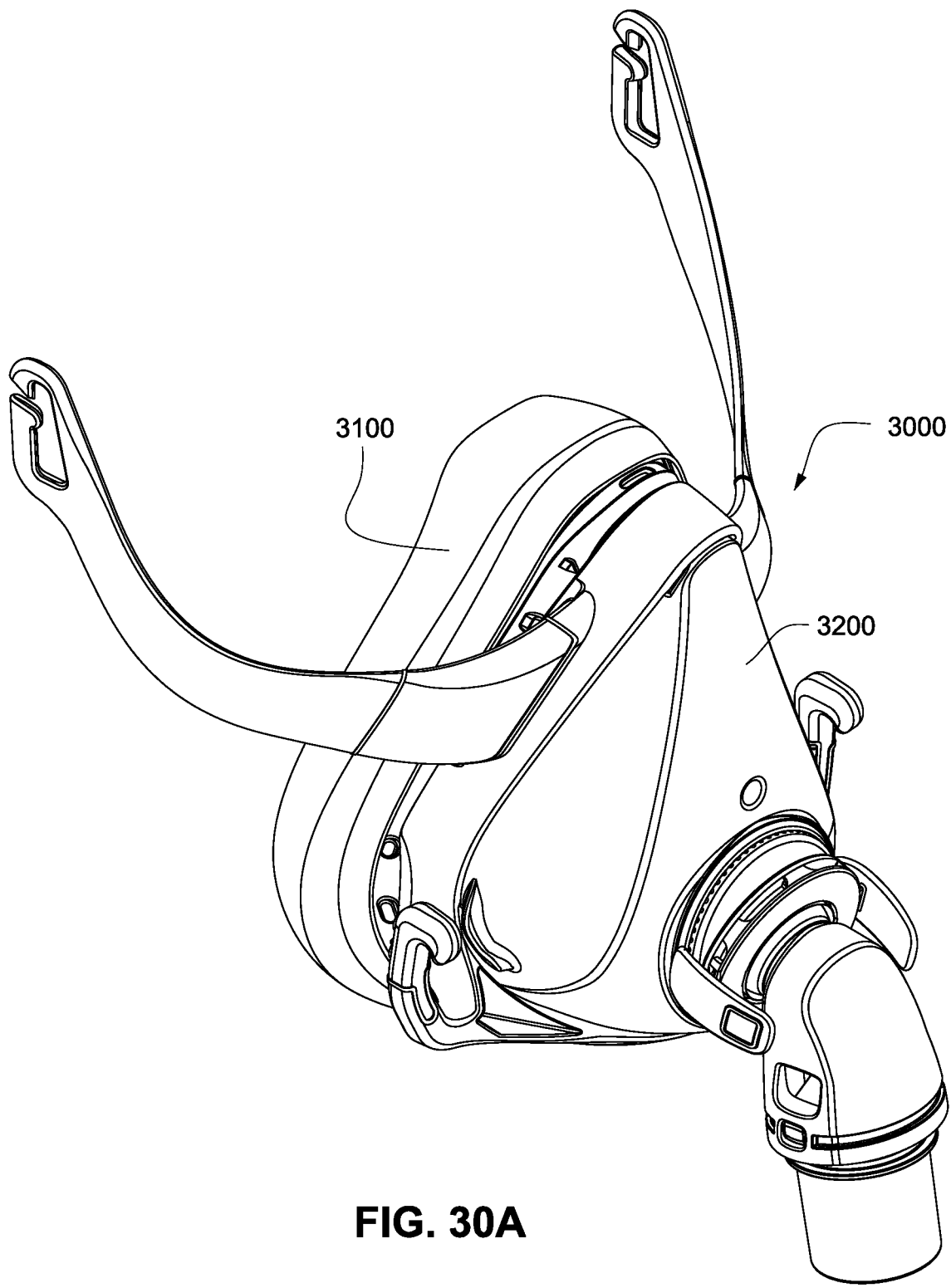

FIG. 30A is a top perspective view of a full-face patient interface according to an example of the present technology.

Figure 30B:
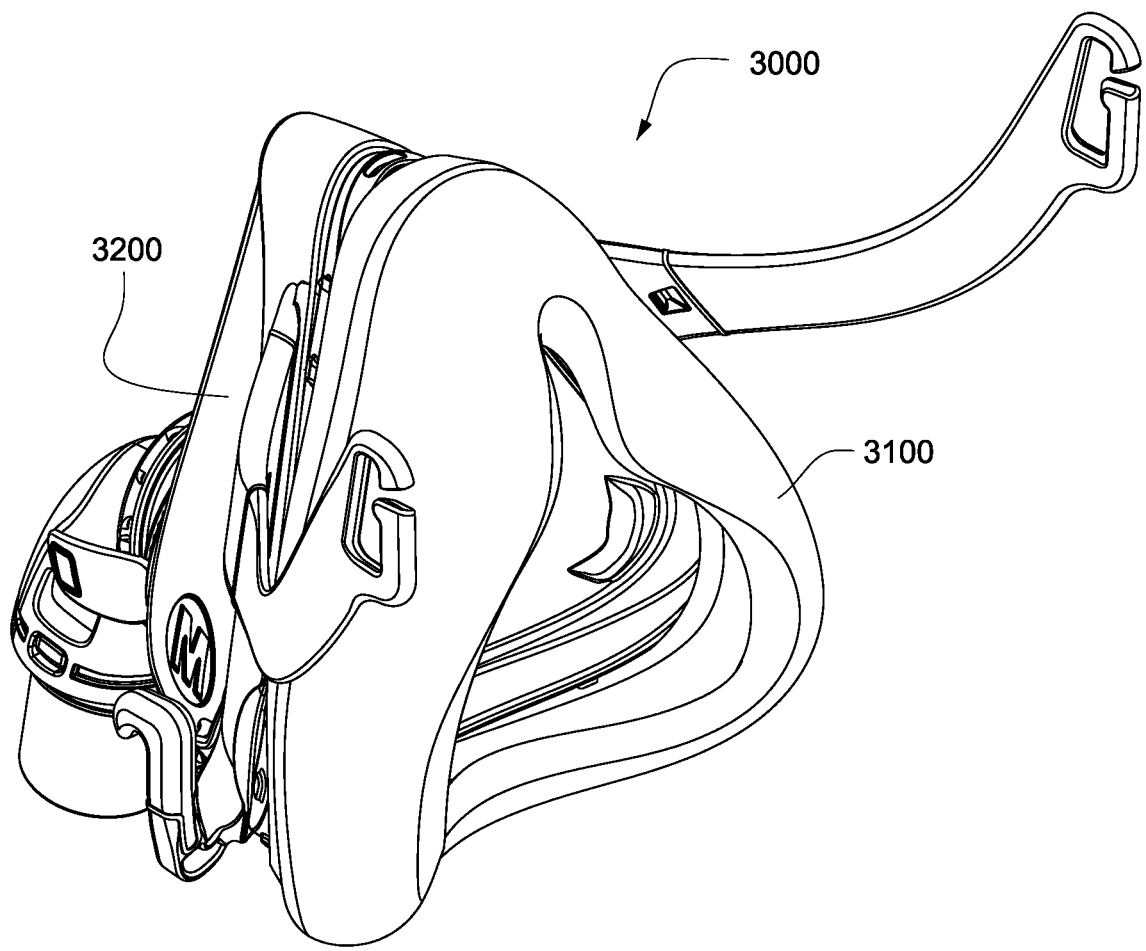

FIG. 30B is a top perspective view of a full-face patient interface according to an example of the present technology.

Figure 30C:
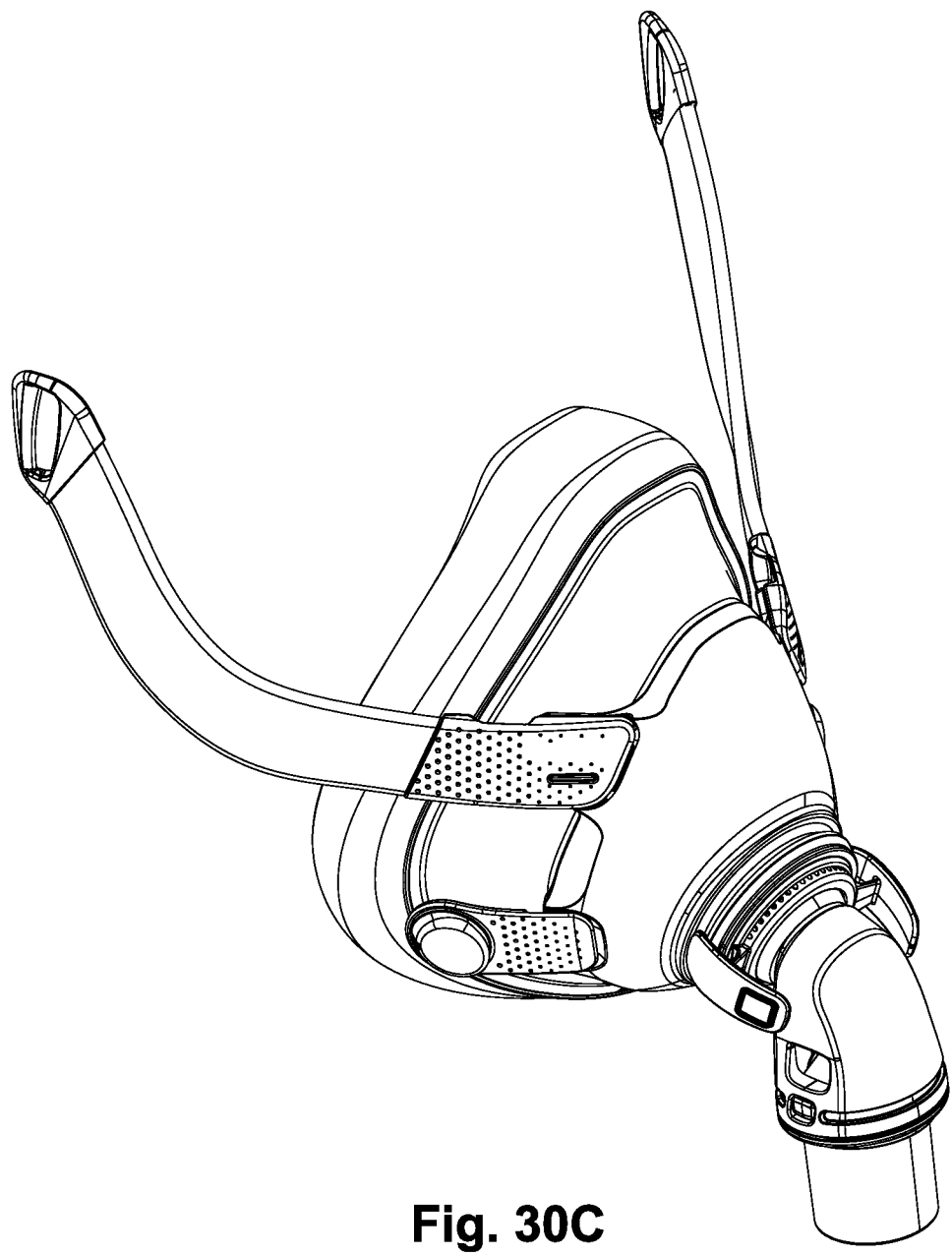

FIG. 30C is a top perspective view of a full-face patient interface according to another example of the present technology.

Figure 30D:
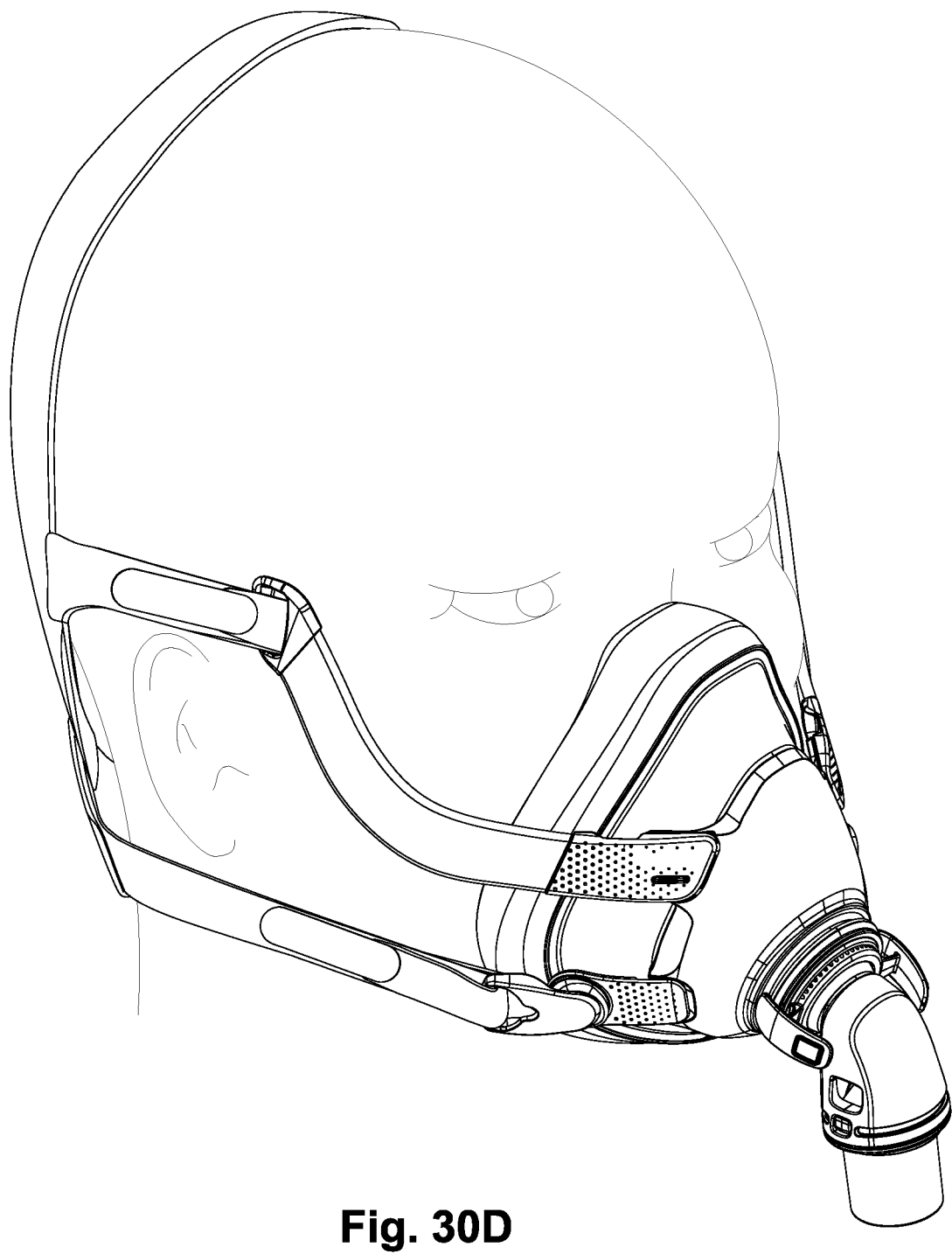

FIG. 30D is a perspective view of the patient interface of FIG. 30C as worn by a patient.

Figure 30E:
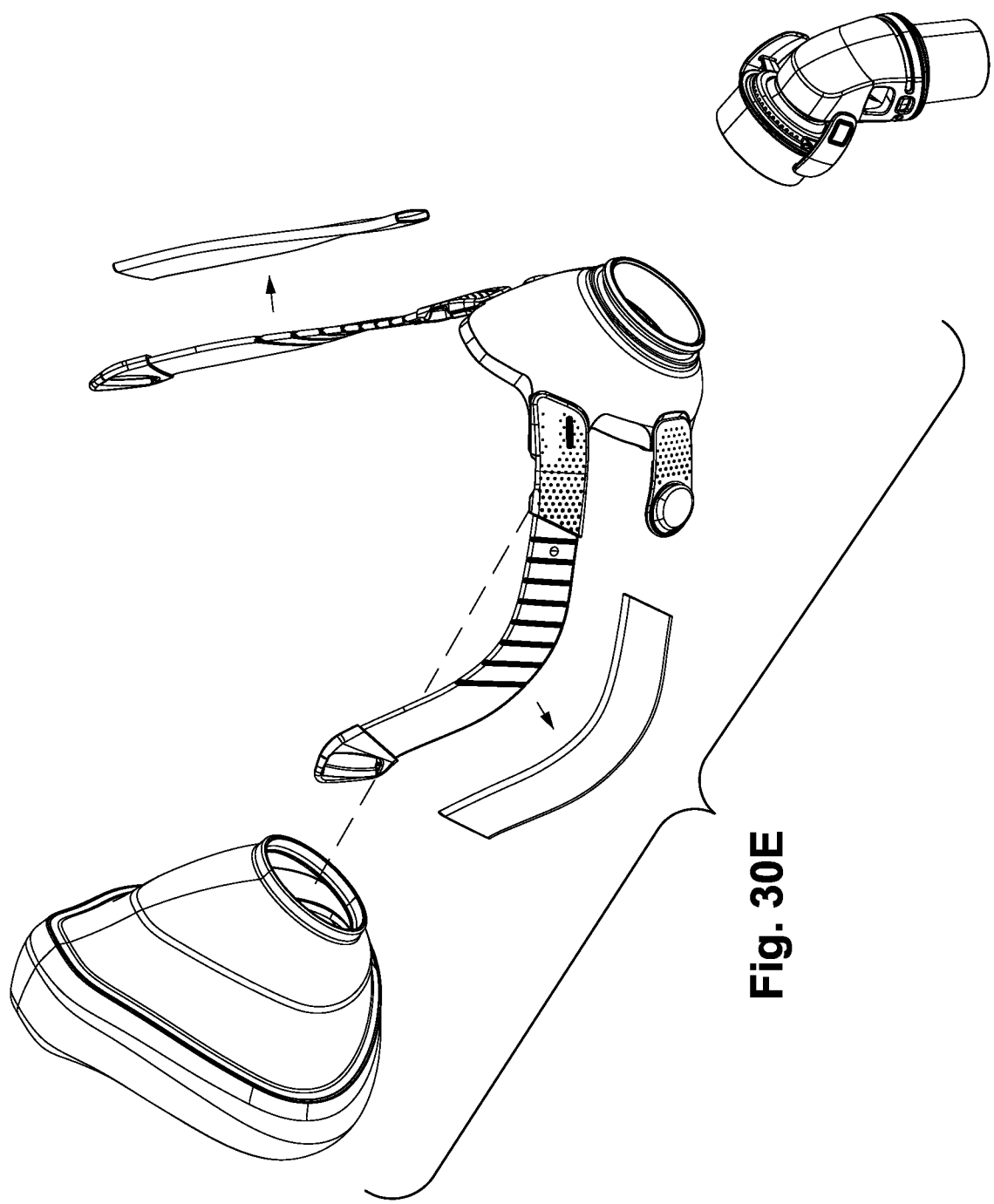

FIG. 30E is an exploded view of the patient interface of FIG. 30C.

Figure 30F:
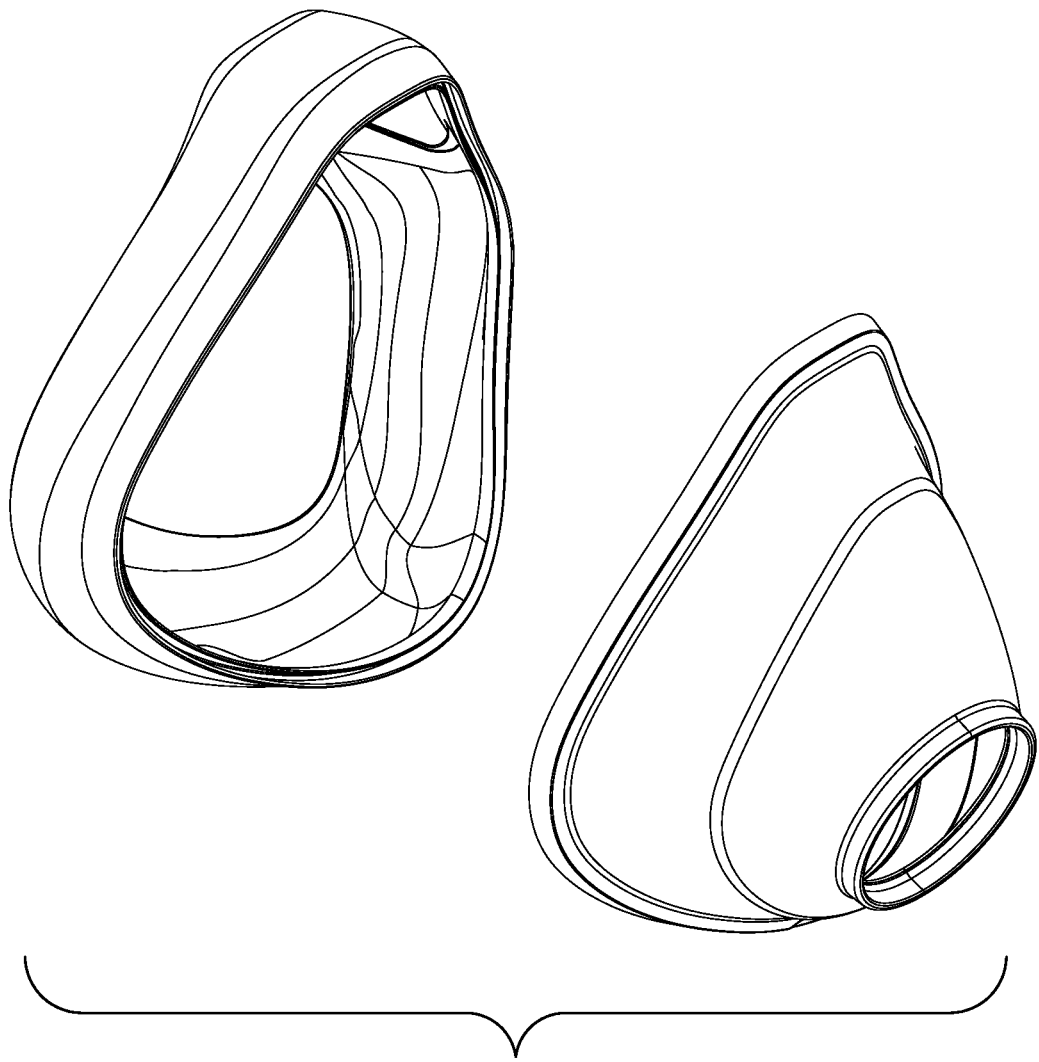

FIG. 30F is another exploded view of the patient interface of FIG. 30C.

Figure 30G:
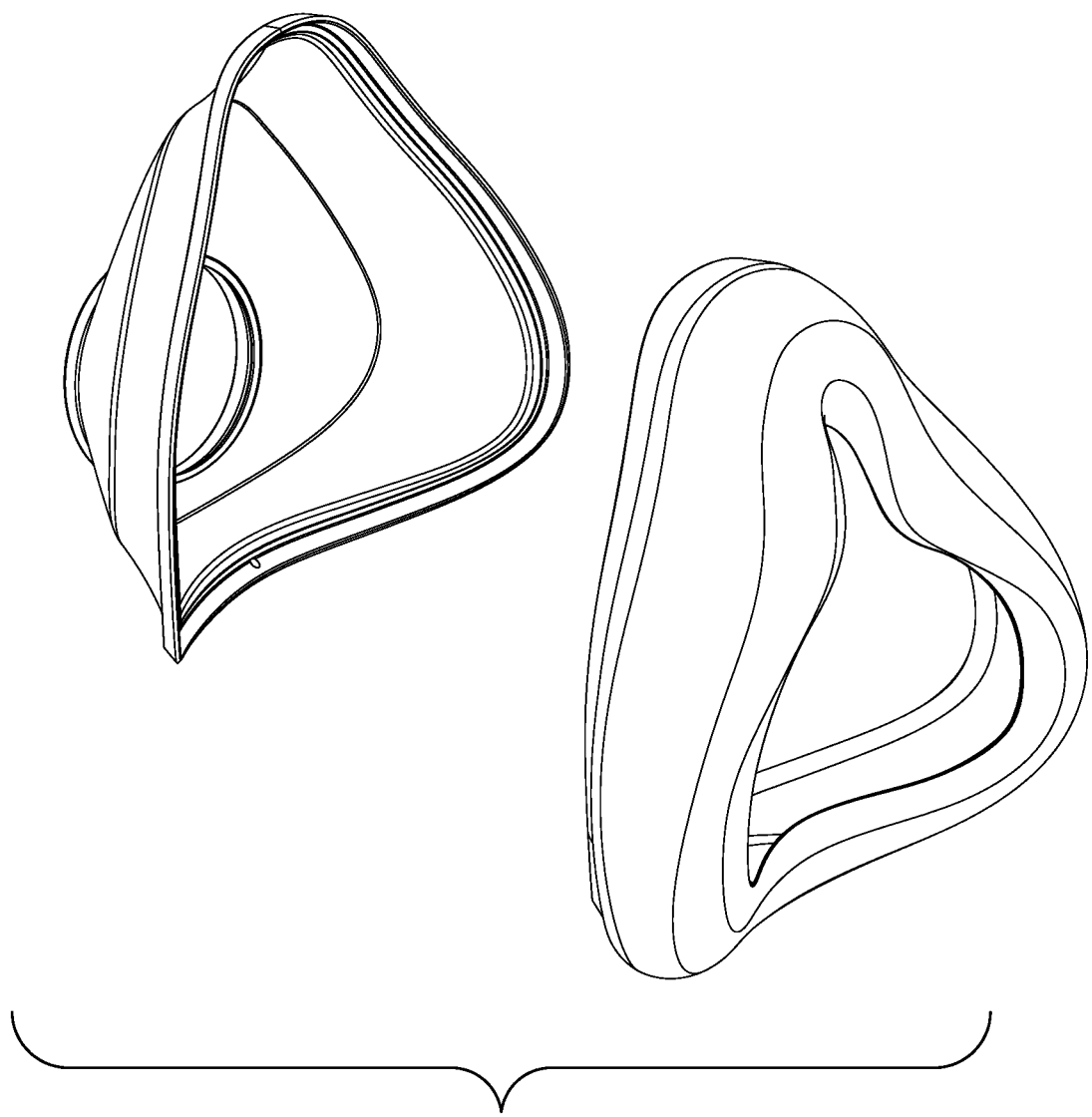

FIG. 30G is another exploded view of the patient interface of FIG. 30C.

Figure 31A:
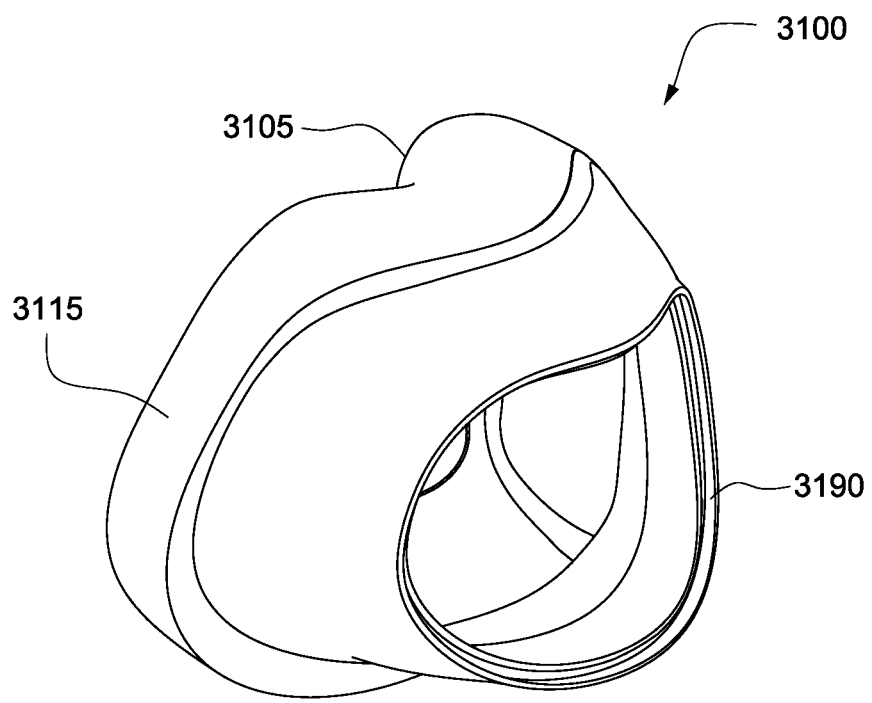

FIG. 31A is a top perspective view of a seal-forming structure for a nasal patient interface according to an example of the present technology.

Figure 31B:
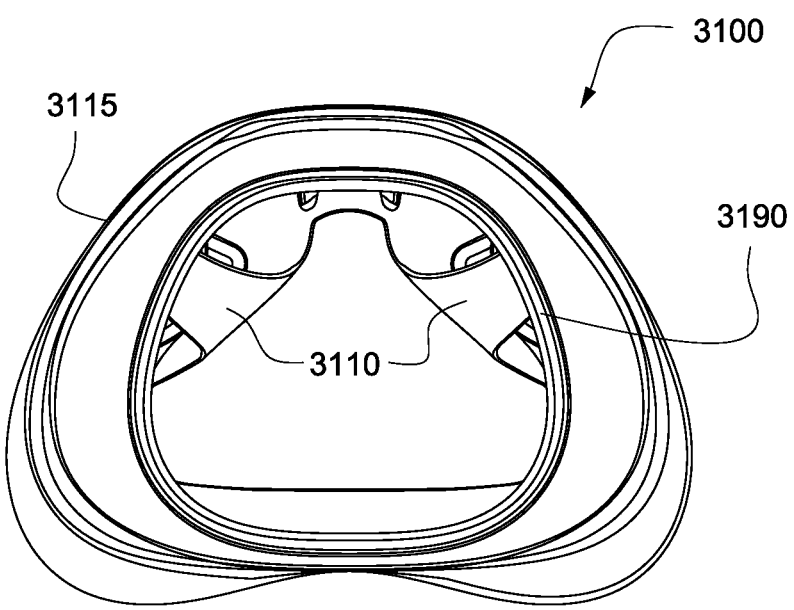

FIG. 31B is a front view of a seal-forming structure for a nasal patient interface according to an example of the present technology.

Figure 31C:
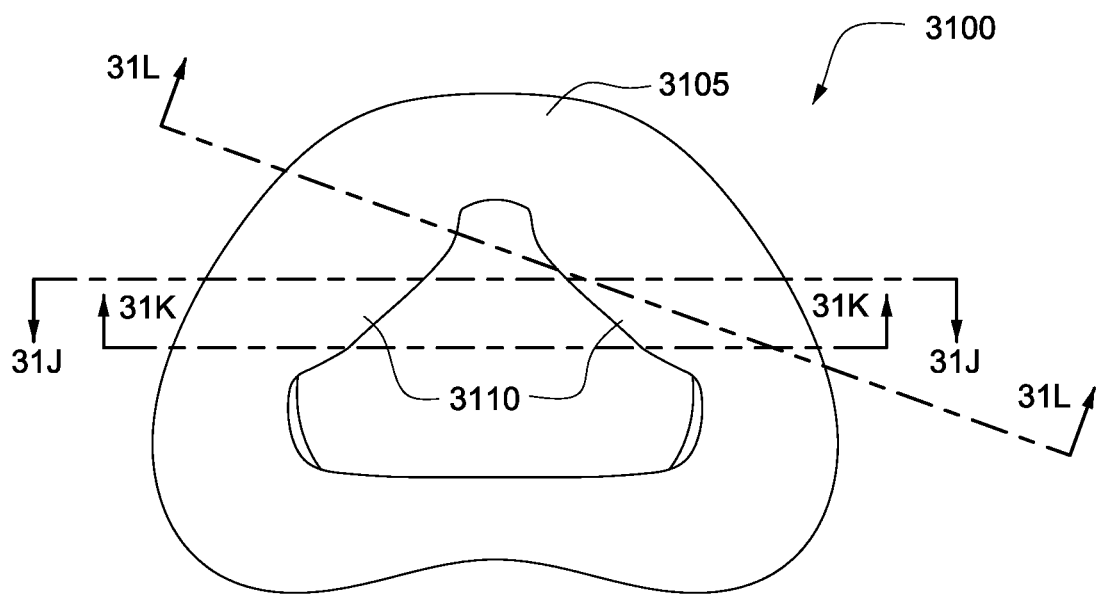

FIG. 31C is a rear view of a seal-forming structure for a nasal patient interface according to an example of the present technology.

Figure 31D:
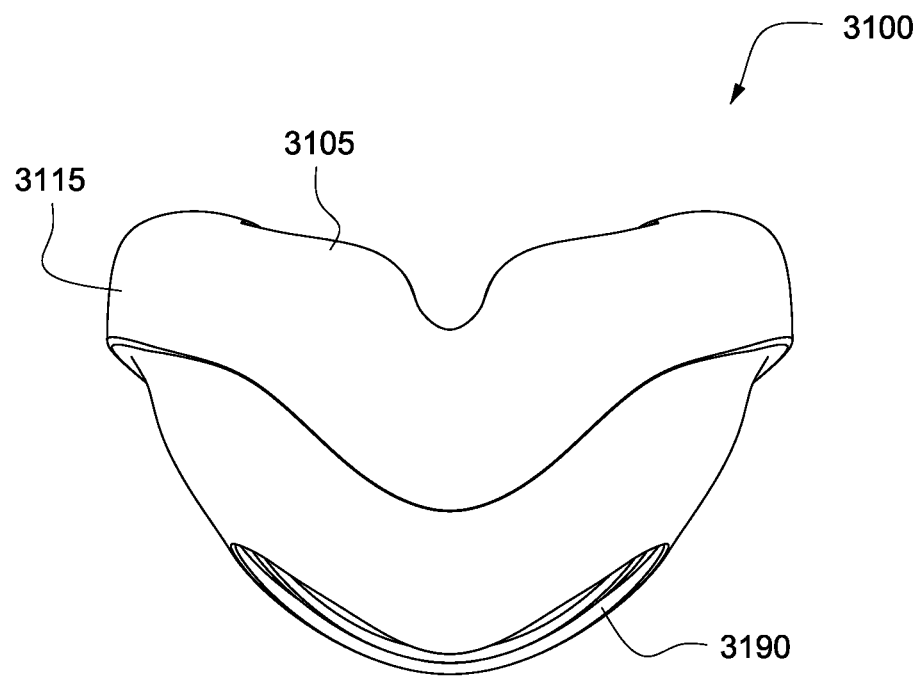

FIG. 31D is a top view of a seal-forming structure for a nasal patient interface according to an example of the present technology.

Figure 31E:
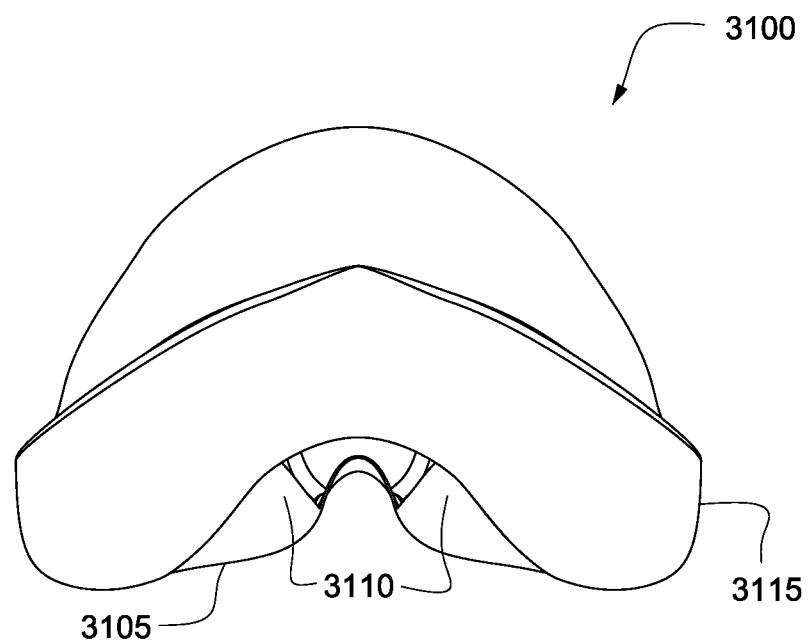

FIG. 31E is a bottom view of a seal-forming structure for a nasal patient interface according to an example of the present technology.

Figure 31F:
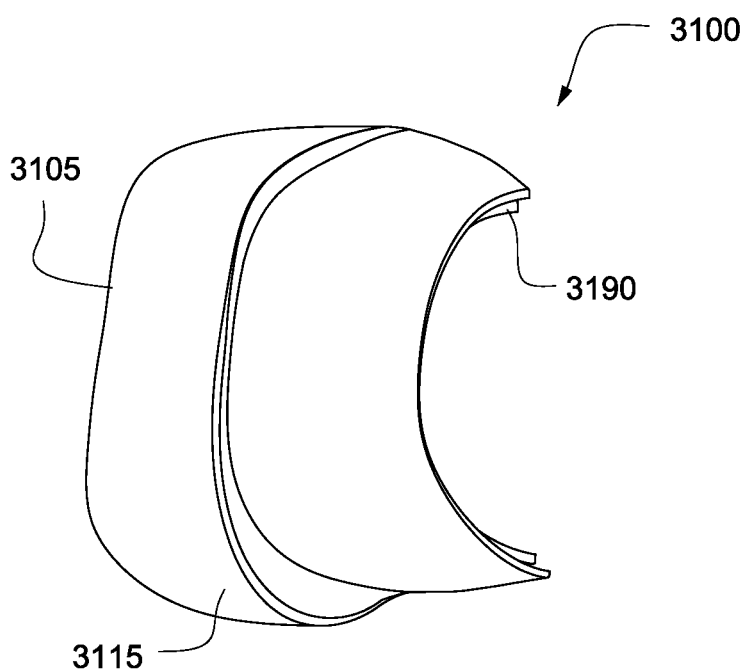

FIG. 31F is a side view of a seal-forming structure for a nasal patient interface according to an example of the present technology.

Figure 31G:
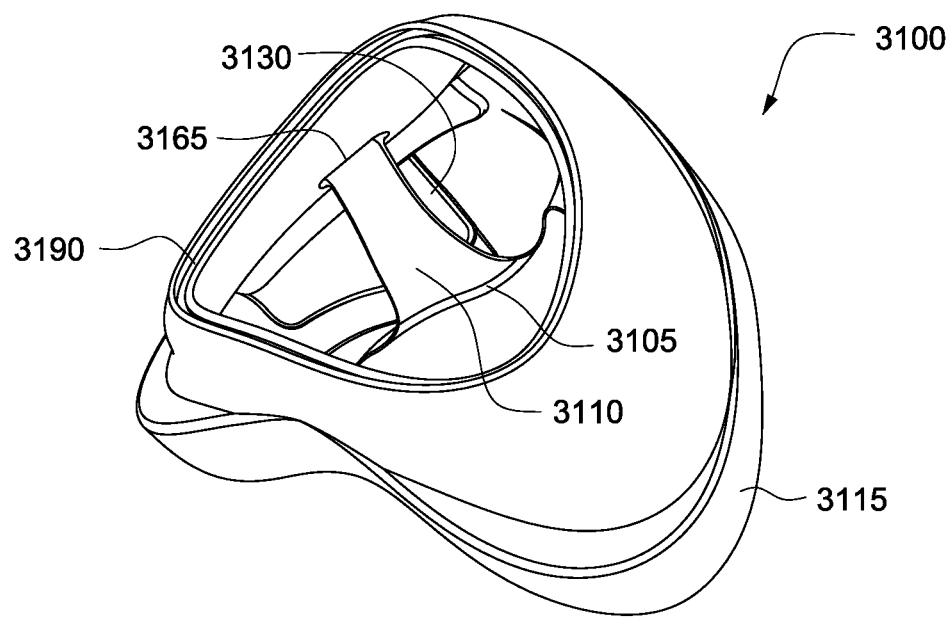

FIG. 31G is a bottom perspective view of a seal-forming structure for a nasal patient interface according to an example of the present technology.

Figure 31H:
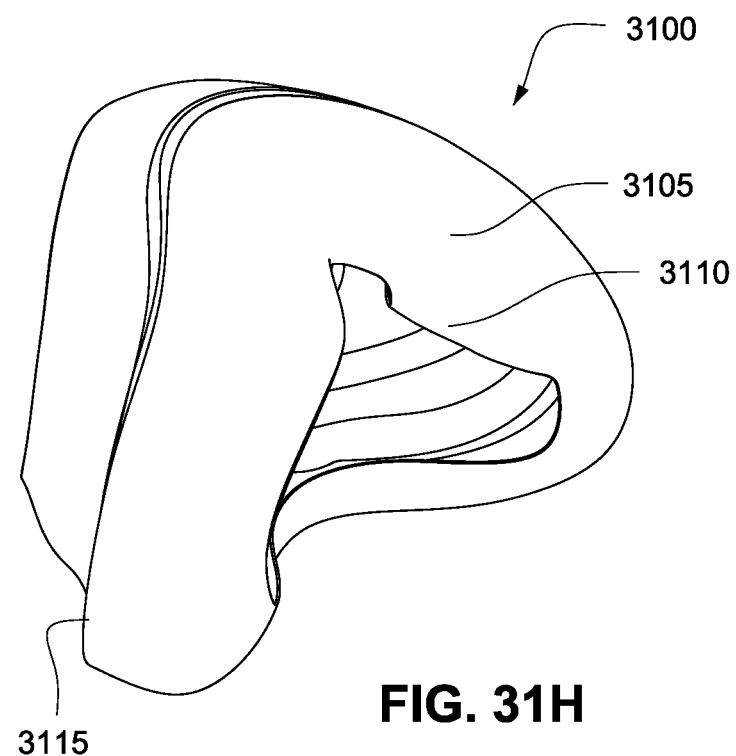

FIG. 31H is another top perspective view of a seal-forming structure for a nasal patient interface according to an example of the present technology.

Figure 31I:
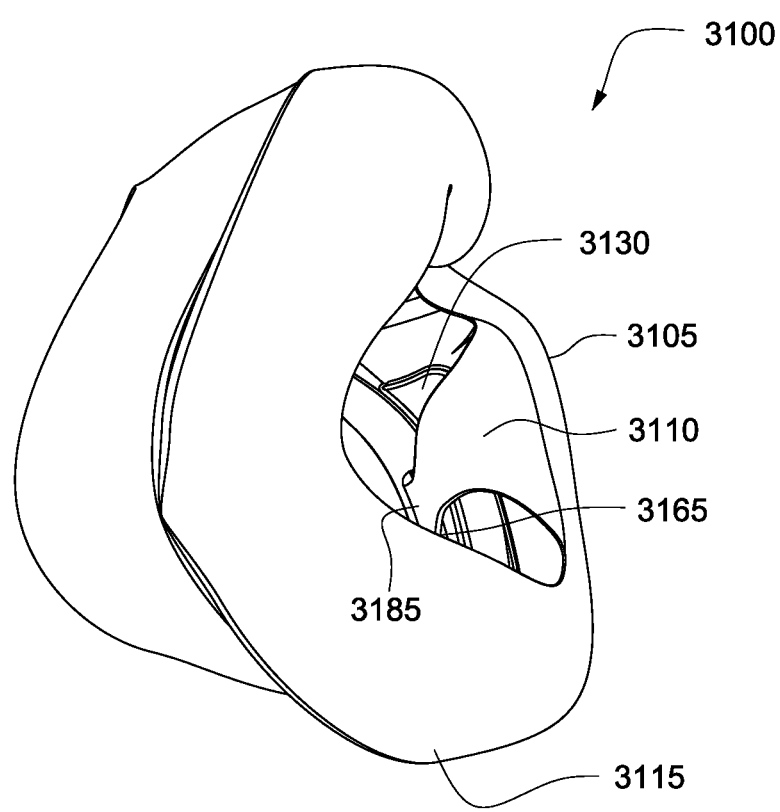

FIG. 31I is another bottom view of a seal-forming structure for a nasal patient interface according to an example of the present technology.

Figure 31J:
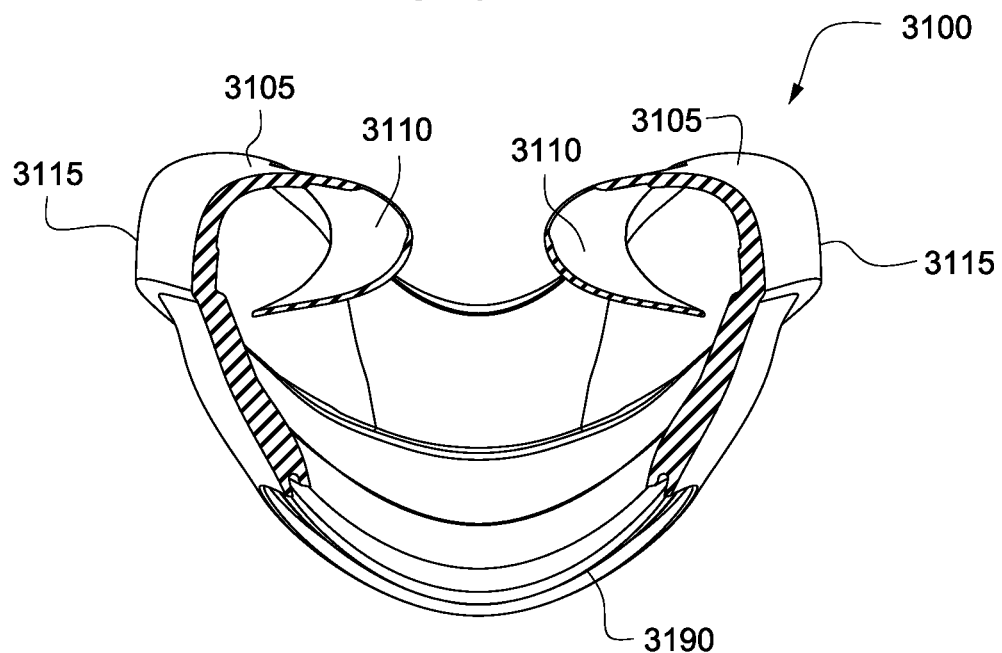

FIG. 31J is a cross-sectional view of a seal-forming structure for a nasal patient interface taken through line 31J-31J of FIG. 31B according to an example of the present technology.

Figure 31K:
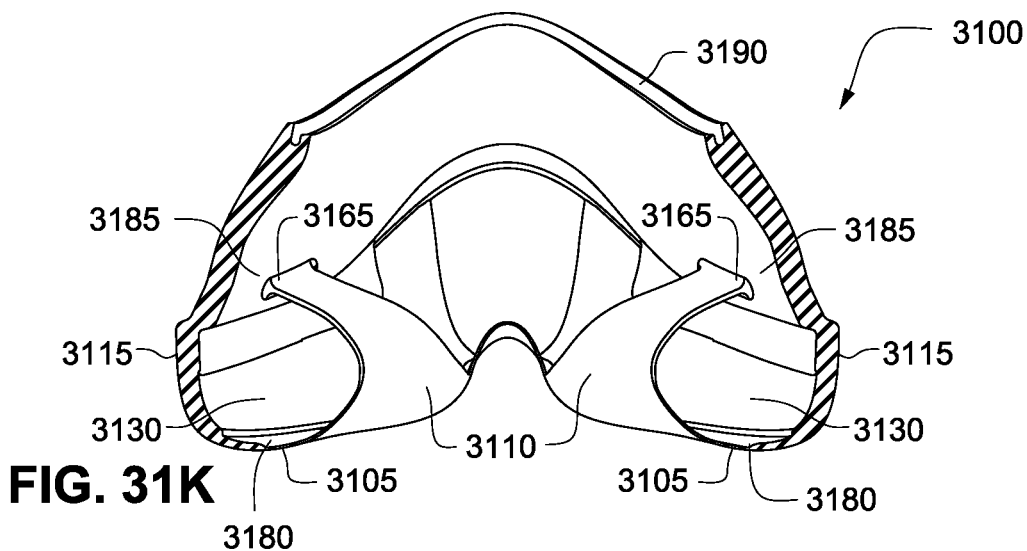

FIG. 31K is a cross-sectional view of a seal-forming structure for a nasal patient interface taken through line 31K-31K of FIG. 31B according to an example of the present technology.

Figure 31L:
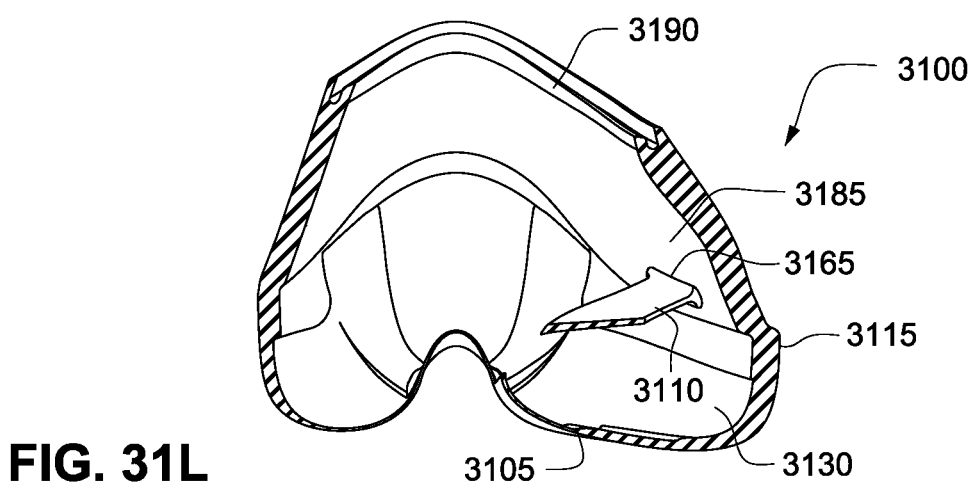

FIG. 31L is a cross-sectional view of a seal-forming structure for a nasal patient interface taken through line 31L-31L of FIG. 31B according to an example of the present technology.

Figure 31M:
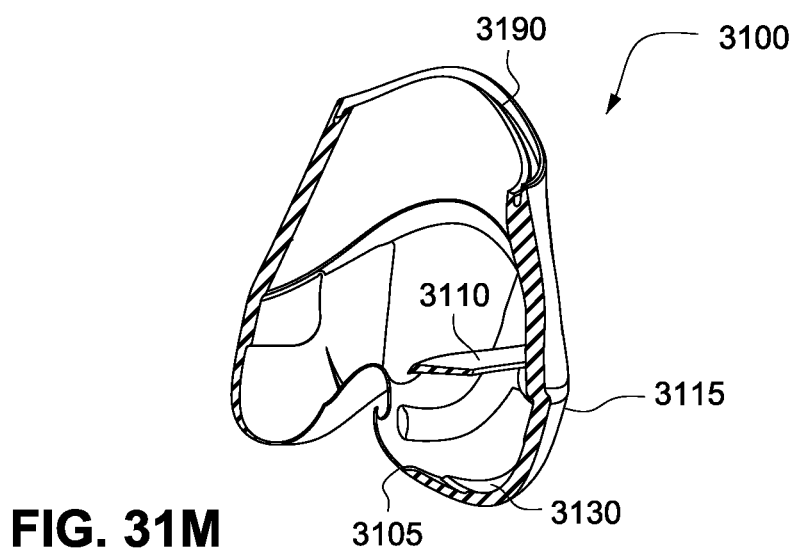

FIG. 31M is a perspective view of a seal-forming structure for a full-face patient interface shown in FIG. 31L.

Figure 32A:
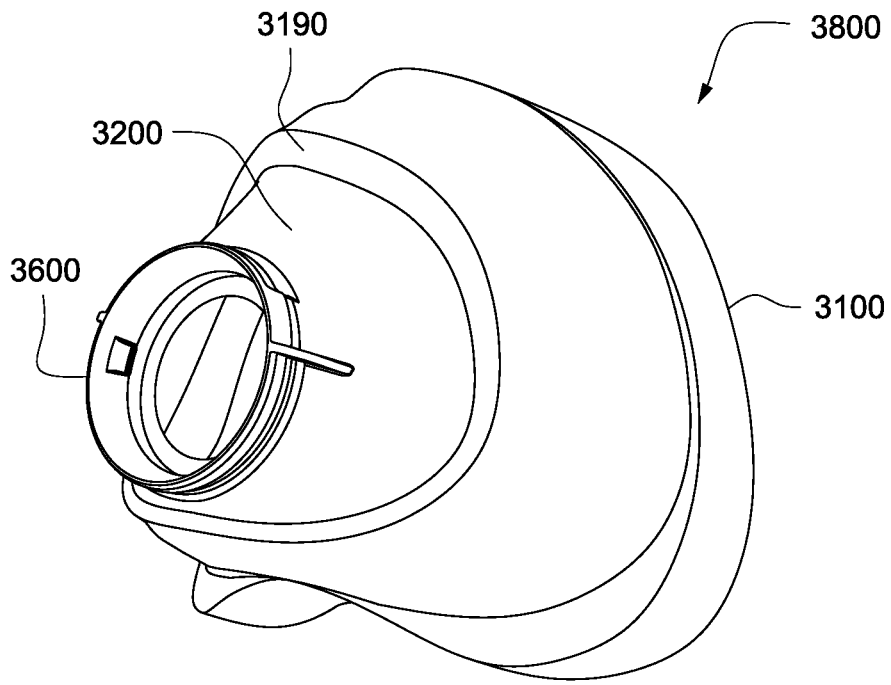

FIG. 32A is a top perspective view of an assembly of a seal-forming structure and a plenum chamber for a nasal patient interface according to an example of the present technology.

Figure 32B:
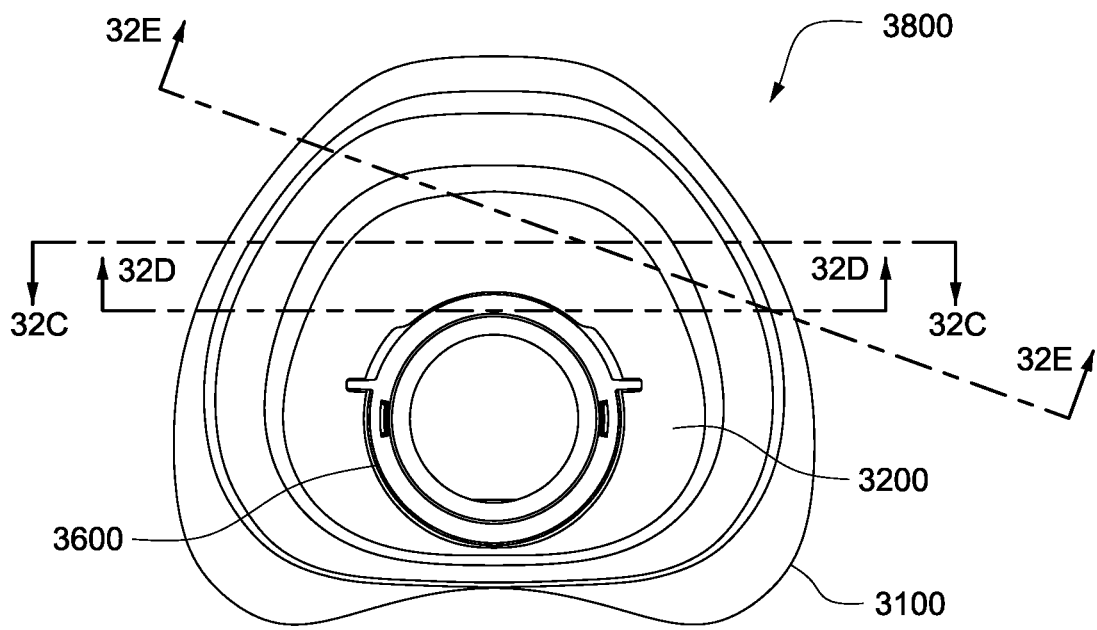

FIG. 32B is a front perspective view of an assembly of a seal-forming structure and a plenum chamber for a nasal patient interface according to an example of the present technology.

Figure 32C:
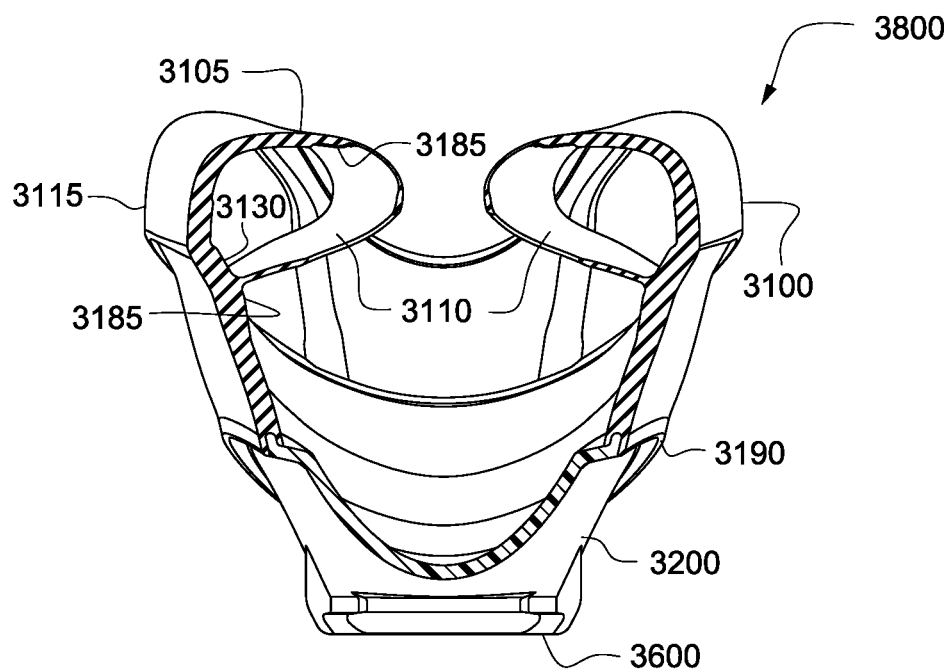

FIG. 32C is a cross-sectional view of an assembly of a seal-forming structure and a plenum chamber for a nasal patient interface taken through line 32C-32C of FIG. 32B according to an example of the present technology.

Figure 32D:
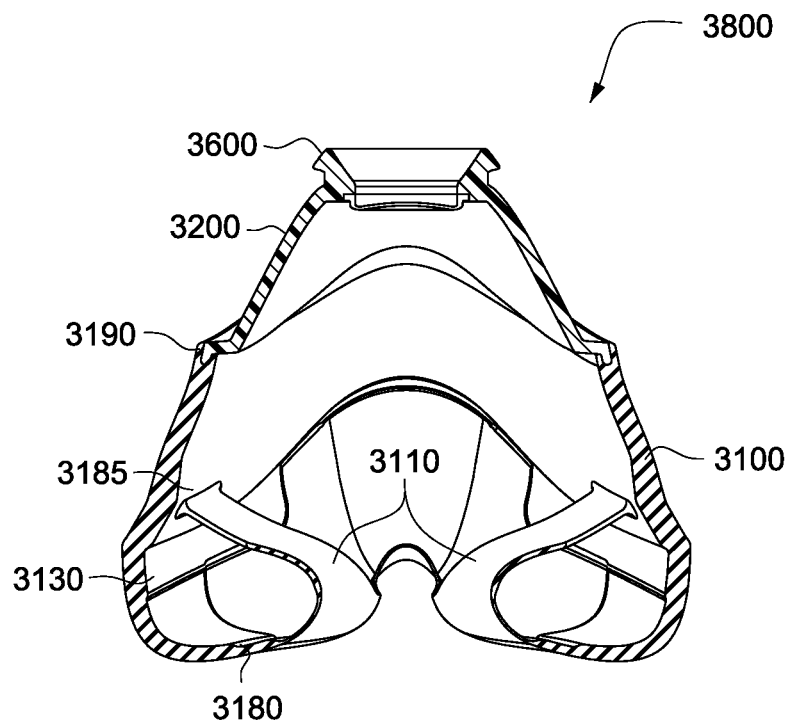

FIG. 32D is a cross-sectional view of an assembly of a seal-forming structure and a plenum chamber for a nasal patient interface taken through line 32D-32D of FIG. 32B according to an example of the present technology.

Figure 32E:
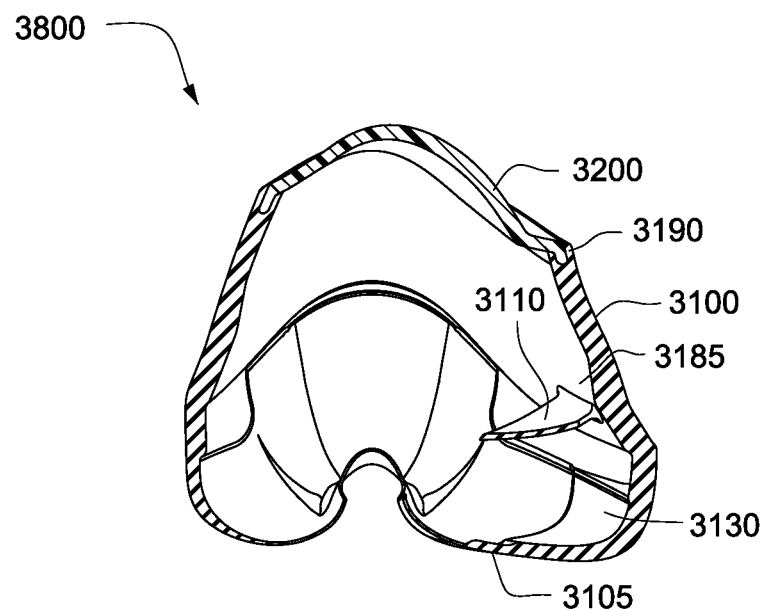

FIG. 32E is a cross-sectional view of an assembly of a seal-forming structure and a plenum chamber for a nasal patient interface taken through line 32E-32E of FIG. 32B according to an example of the present technology.

Figure 32F:
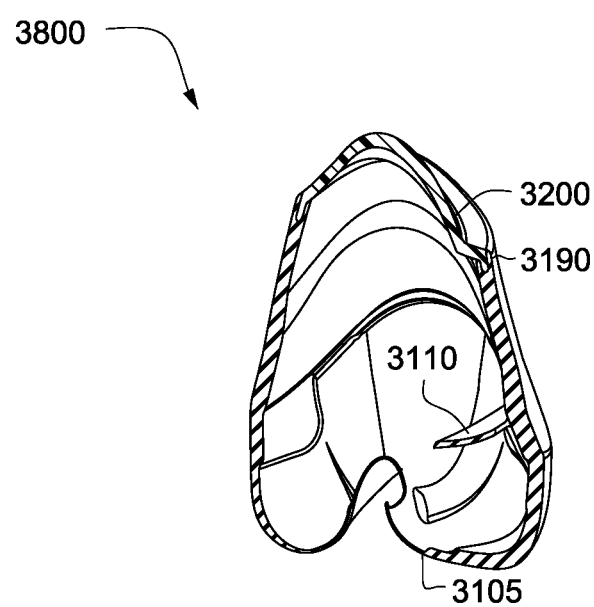

FIG. 32F is another cross-sectional view of an assembly of a seal-forming structure and a plenum chamber for a nasal patient interface according to an example of the present technology.

Figure 33A:
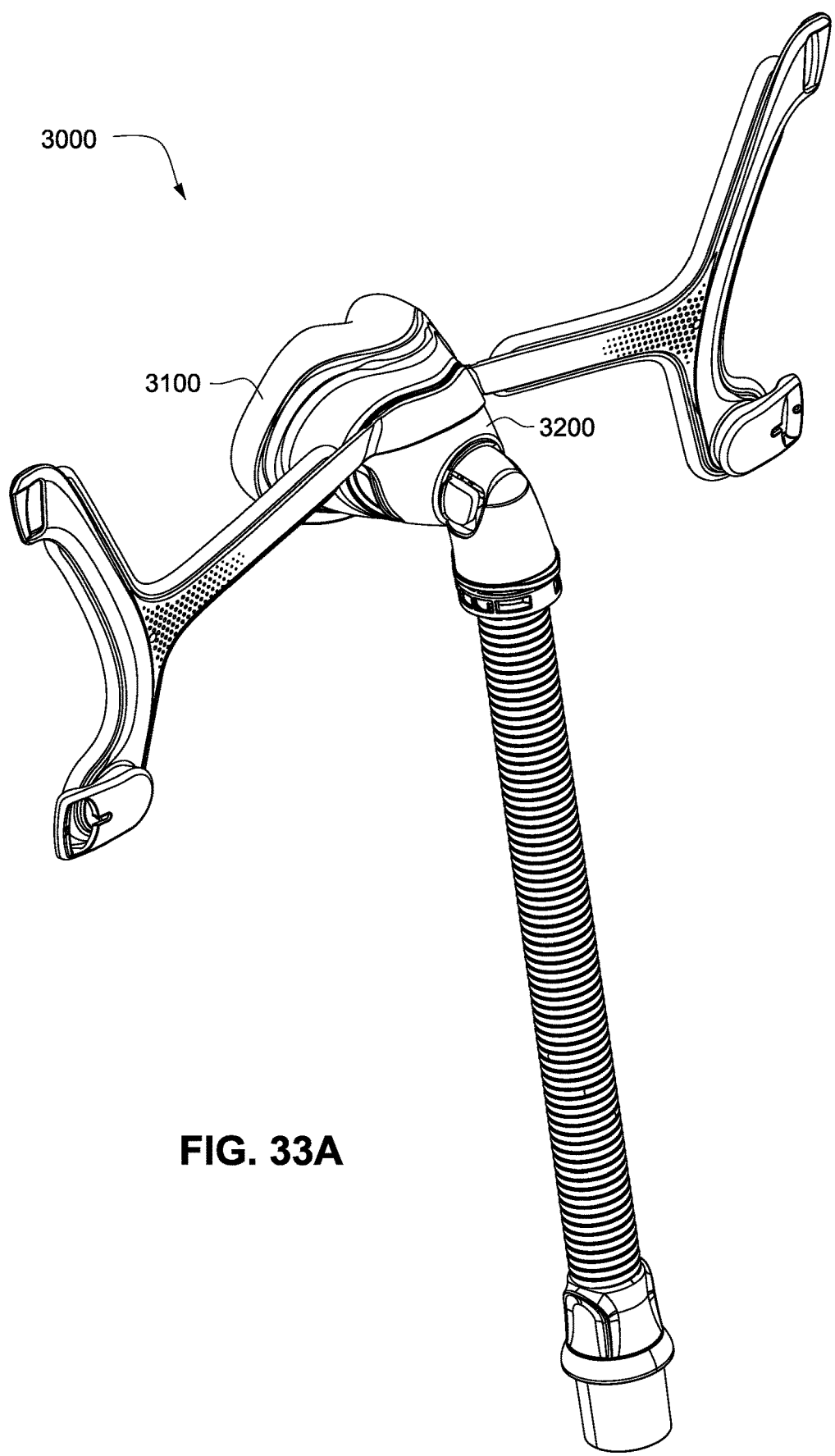

FIG. 33A is a top perspective view of a nasal patient interface according to an example of the present technology.

Figure 33B:
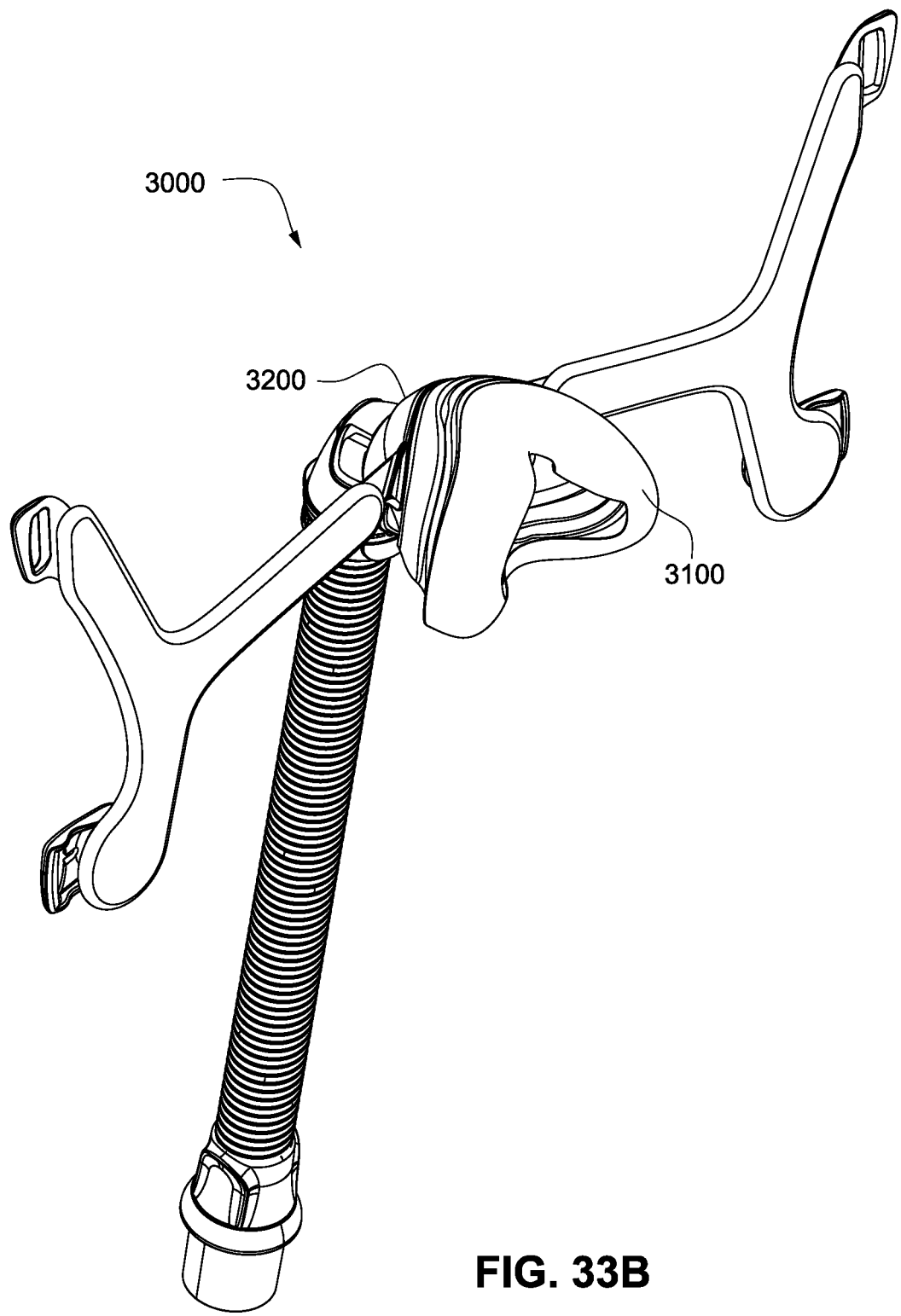

FIG. 33B is a top perspective view of a nasal patient interface according to an example of the present technology.

Figure 34A:
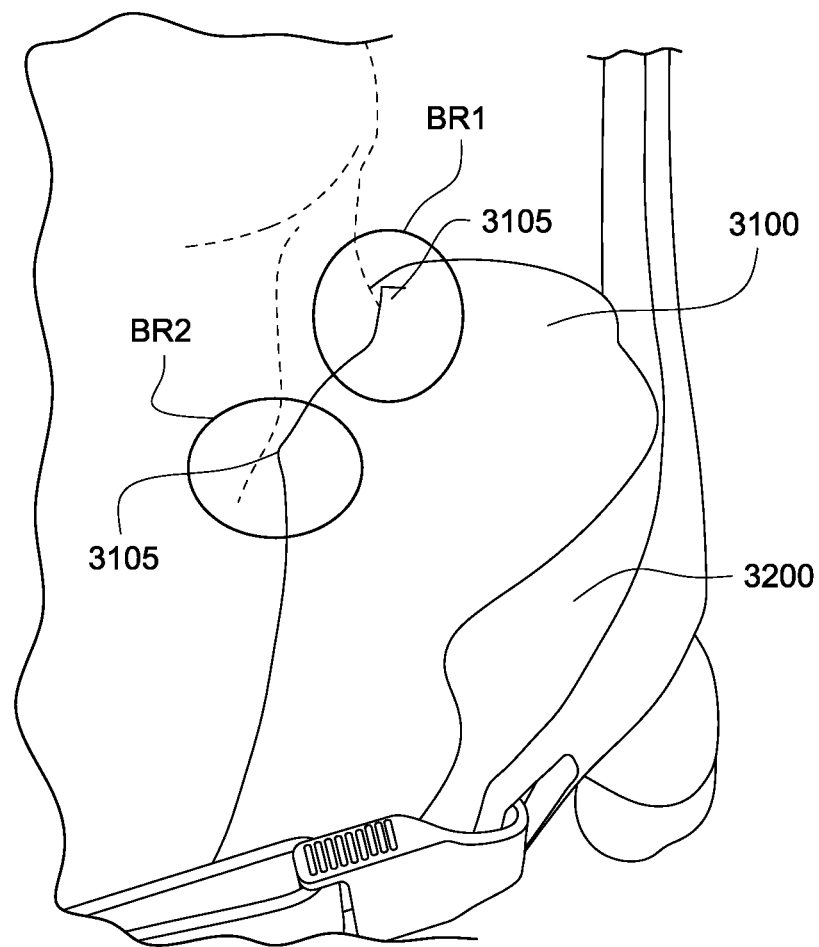

FIG. 34A is a detailed side view of a seal-forming structure for a full-face patient interface according to a related technology in which a therapy pressure is applied.

Figure 34B:
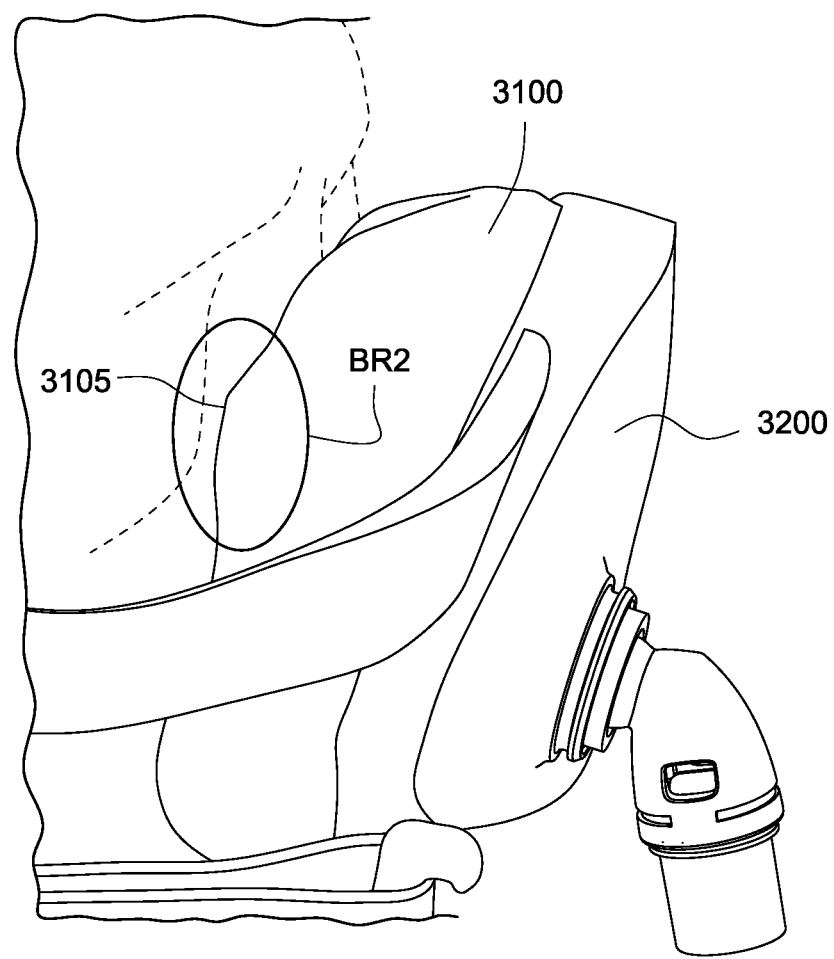

FIG. 34B is a detailed side view of a seal-forming structure for a full-face patient interface according to another related technology in which a therapy pressure is applied.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 THERAPY

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 TREATMENT SYSTEMS

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.3 PATIENT INTERFACE

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

The inventors have found that if a patient interface 3000 is unable to comfortably deliver a minimum level of positive pressure to the airways that treatment may be ineffective.

The patient interface 3000 in accordance with one form of the present technology is constructed and arranged to be able to provide a supply of air at a positive pressure of at least 6 cmH2O with respect to ambient.

The patient interface 3000 in accordance with one form of the present technology is constructed and arranged to be able to provide a supply of air at a positive pressure of at least 10 cmH2O with respect to ambient.

The patient interface 3000 in accordance with one form of the present technology is constructed and arranged to be able to provide a supply of air at a positive pressure of at least 20 cmH2O with respect to ambient.

4.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

In certain forms of the present technology, a system is provided comprising more than one a seal-forming structure 3100, each being configured to correspond to a different size and/or shape range. For example, the system may comprise one form of a seal-forming structure 3100 suitable for a large sized head, but not a small sized head and another suitable for a small sized head, but not a large sized head.

In certain forms of the present technology, the seal-forming structure 3100 is constructed from a biocompatible material, e.g. silicone rubber.

FIG. 4 illustrates a perspective view of a seal-forming structure 3100 separated from a remainder of the patient interface 3000. The seal forming structure includes a sealing surface 3105 that is configured to form a seal around a periphery of a patient's airways. The seal may be formed around the patient's nose or the patient's nose and mouth.

The seal forming structure 3100 includes a tie, connecting portion, or loop 3110 that folds the sealing structure 3100 inwards (e.g., towards the patient's face in use) of an outer perimeter 3115 of the sealing structure 3100. The outer perimeter 3115 may be generally defined as a wall that supports and/or is formed continuously with the sealing surface 3105. In this manner, the tie 3110 may form a substantially tube-shaped structure 3120 so that the tie 3110 forms a continuous structure (e.g., continuous circumference) with the sealing surface 3105 and the outer perimeter 3115. Thus the tie 3110 may include a portion of the sealing surface 3105, a portion of the outer perimeter 3115 and a portion that is neither the sealing surface 3105 nor the outer perimeter 3115. The portion that is neither the sealing surface 3105 nor the outer perimeter 3115 may be in the form of a flap or sheet attached or continuous with one end to the sealing surface and at another end with the outer perimeter 3115. The tie 3110 may be located to be alongside the patient's nose, e.g., along the alar, above the nasal bone or anywhere in between. Two ties 3110 may be provided on opposite sides of the patient's nose. The tie 3110 may be open internally, including one or both ends, so that the tie 3110 is internally pressurized (e.g., in fluid communication) with the patient's treatment pressure in use.

In one form of the present technology, the tie 3110 may extend only partially around the periphery of the seal forming structure 3100.

In one form, the tie 3110 and the seal forming structure 3100 do not form a closed, pressurizable structure (e.g., a bladder) such that the space between the tie 3110 and the seal forming structure 3100 is open to the pressure in the interior of the patient interface 3000.

In one form the seal forming structure 3100 has an edge and the tie 3110 holds the edge to prevent blowout at the edge.

Areas of the sealing surface 3105 other than the tie 3110 may include a sealing flap 3125 that protrudes inwards towards an inner perimeter of the sealing structure 3100. The sealing flap 3125 may have an unconnected edge at or near a radially inner portion of the sealing surface 3105. The sealing flap 3125 may include a portion 3125a that is configured to form a seal against the sides of the nose above the nasal bones of the patient. The sealing flap 3125 may be structured to avoid sealing against the alar, e.g., by being spaced sufficiently far radially outward with respect to the alar to avoid or minimize contact with the alar.

FIG. 5 illustrates a substantially opposite perspective view of the seal forming structure 3100 than that illustrated in FIG. 4. The substantially tube-shaped structure 3120 may be more readily apparent from this view. FIG. 5A illustrates the tie 3110 with a closed end 3111. This figure also illustrates the seal forming structure 3100 without an underlying cushion, and thus the seal forming structure 3100 may be referred to as a single layer cushion.

FIG. 6 illustrates a plan view of the seal forming structure 3100 and serves as the basis for two section views illustrated in FIGS. 7 and 8.

FIG. 7 is a cross-section taken through the tie 3110. The substantially tube-shaped structure 3120 may be more readily discerned from this view. The tie 3110 includes a relatively thick portion 3130 and a relatively thin portion 3135. The relatively thick portion 3130 may be between 1 mm and 2 mm thick, or between 1.3 mm and 1.7 mm thick, or about 1.5 mm thick. The relatively thin portion 3135 may be between 0.2 mm and 0.8 mm thick, or between 0.4 mm and 0.6 mm thick, or about 0.5 mm thick. Alternatively, the relatively thick portion 3130 may be about 2.5 to 5 times as thick as the relatively thin portion 3135, or about 2.8 to 3.3 times as thick as the relatively thin portion 3135, or three times as thick as the relatively thin portion 3135. The relatively thick portion 3130 is illustrated to include the outer perimeter 3115 and most of the sealing surface 3105 at the tie 3110. The relatively thin portion 3135 folds the sealing structure inwards and connects back to the seal forming structure 3100 at a connection point 3165 that is at or near a hinge structure 3140. The hinge structure 3140 is illustrated as a localized, relatively thin strip or line that may provide preferential bending or flexing at a predetermined location, which may provide flexibility for the seal forming structure 3100 to conform to the patient's face. The relatively thick portion 3130 may provide sufficient resilience to provide an effective seal against the patients face. The relatively thin portion 3135 may provide resistance to the sealing surface 3105 blowing out under pressure while not causing the sealing surface 3105 to have too much rigidity and be too stiff to form an effective seal. Alternatively, the thicknesses of the relatively thick portion 3130 and the relatively thin portion 3135 could be the reverse of what is illustrated in FIG. 7. Or the relatively thin portion 3135 could be extended to encompass the sealing surface 3105. Any combination of thicknesses may be employed to achieve a desired combination of sealing ability and resistance to blow out.

The connection point 3165 may be determined based upon the desired force to be applied by, or desired resilience of, the tie 3110. For example, as illustrated in FIG. 7A, the angle 3170 formed by the relatively thin portion 3135 may be varied. As the angle 3170 is varied, the tension in the relatively thin portion 3135 will also vary. The angle 3170 can thus be optimized to prevent blowout and/or for patient comfort.

Figure 7B:
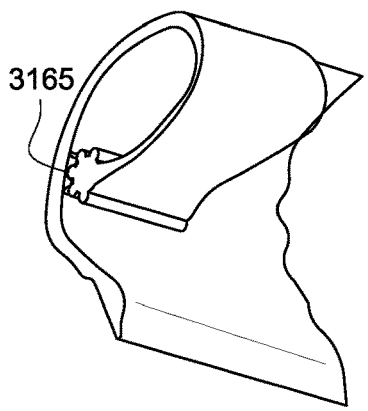
Figure 7C:
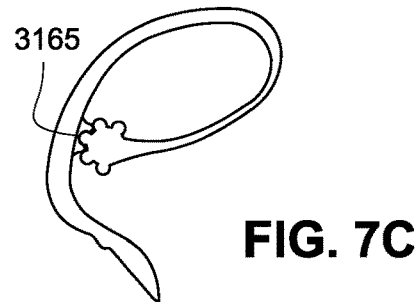
Figure 7D:
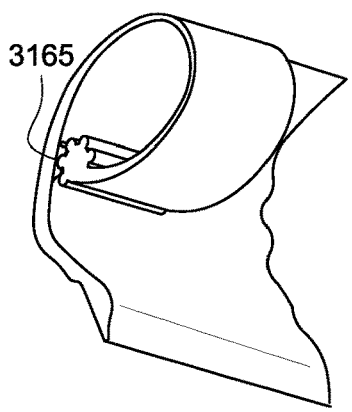
Figure 7E:
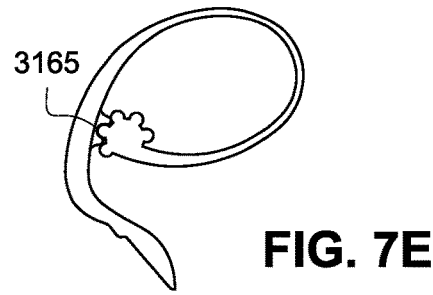
Figure 7F:
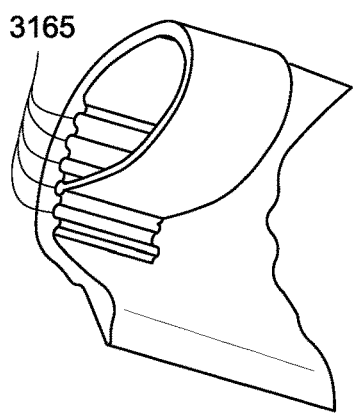
Figure 7G:
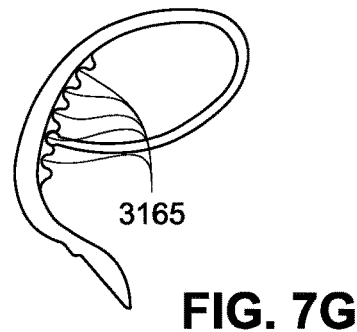
Figure 7H:
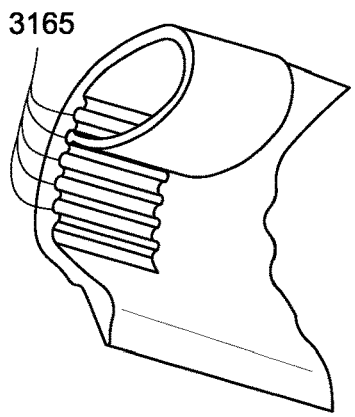
Figure 7I:
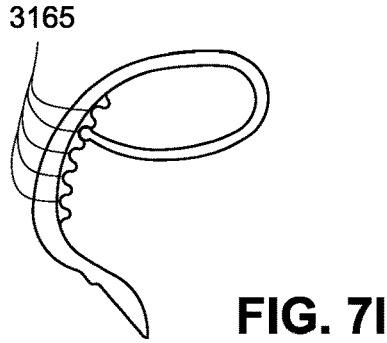

The angle 3170 may be predetermined in several ways. For example, if the seal forming structure 3100 is a single moulded piece, the mould used to form the seal forming structure 3100 will determine the angle 3170. Different angles can be achieved with different moulds. Alternatively, the relatively thin portion 3135 may be manufactured in an un-connected state so that the connection point 3165 is formed in a later assembly step. The connection point 3165 could be a mechanical connection or an adhesive bond. If an adhesive bond is used, the connection point 3165 may be continuously varied within an acceptable range of attachment. Alternatively, a mechanical attachment could be used. FIGS. 7B-7I illustrate exemplary mechanical attachments. In FIGS. 7B-7E, the connection point 3165 is keyed so that different angles can be achieved in a single connection point 3165. FIGS. 7B and 7C illustrate a first connection orientation of the keyed connection and FIGS. 7D and 7E illustrate a second connection orientation of the keyed connection. In FIGS. 7F-7I, multiple discrete connection points 3165 are provided. The connection point 3165 that is selected will determine the angle 3170. FIGS. 7F and 7G illustrate a first discrete connection of the discrete connection points and FIGS. 7H and 7I illustrate a second discrete connection of the discrete connection points. The particular geometry illustrated in FIGS. 7B-7I is exemplary only and should not be considered limiting. Other keyed or discrete connection geometries may be used.

As may be appreciated from FIG. 7, the tie 3110 may be positioned to contact a side wall of the nose including the alar. The tie 3110 may also provide a continuous surface to maintain contact with the sides of the nose above the nasal bones of the patient.

Figure 8A:
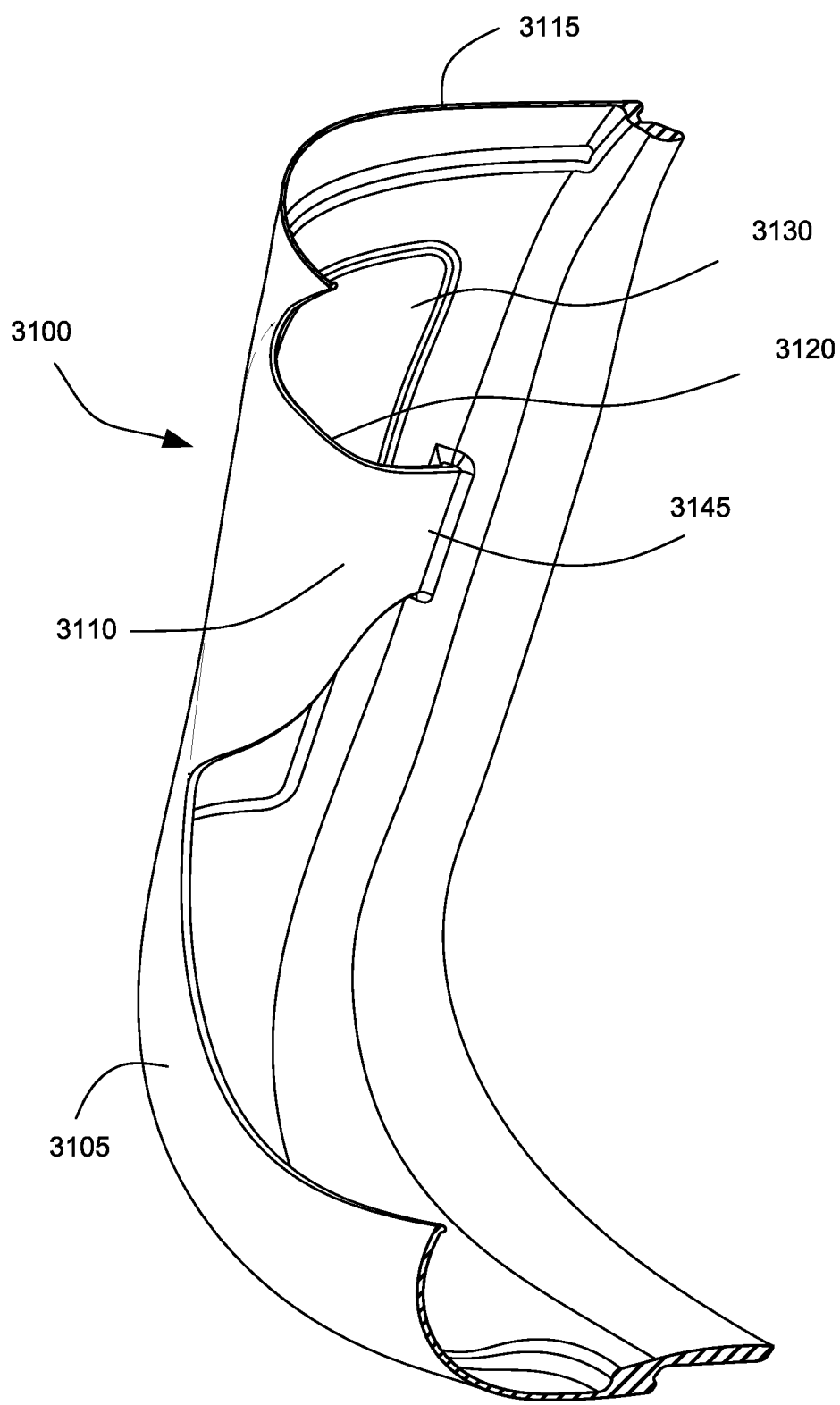
Figure 8B:
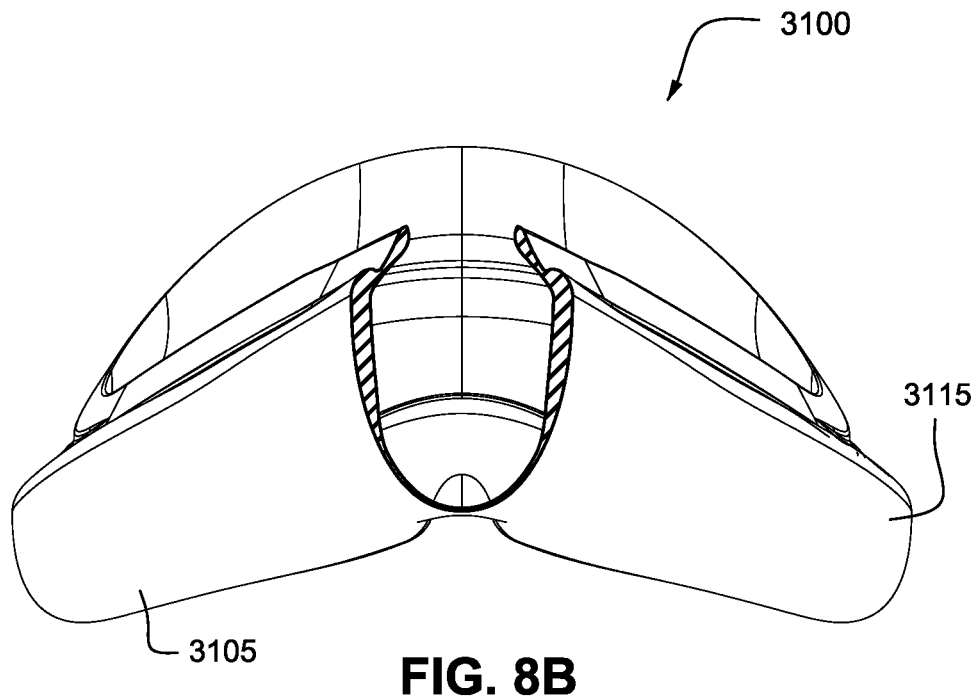
Figure 8C:
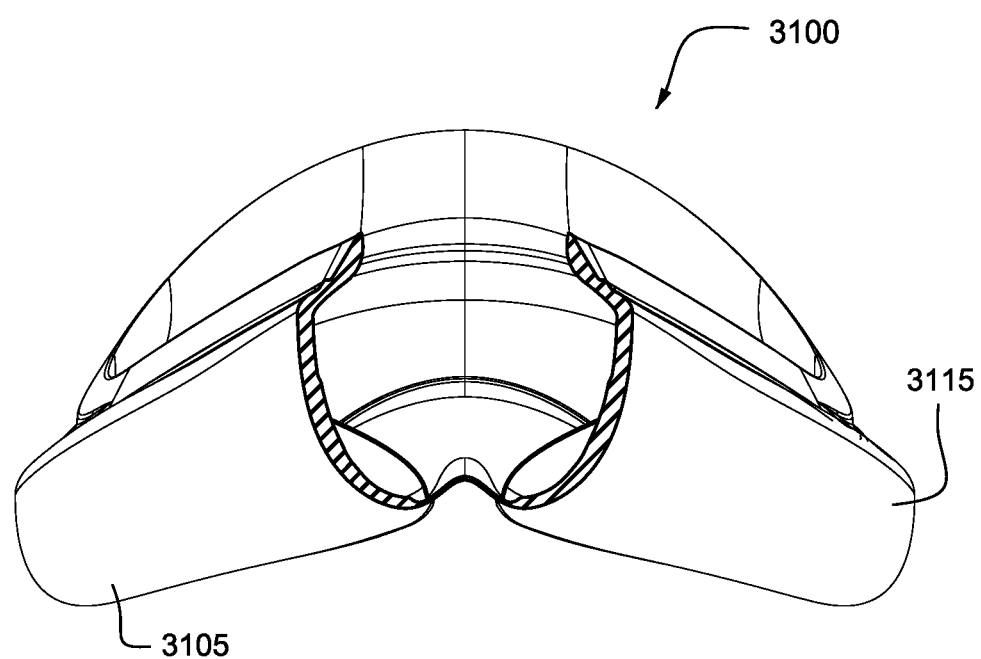
Figure 8D:
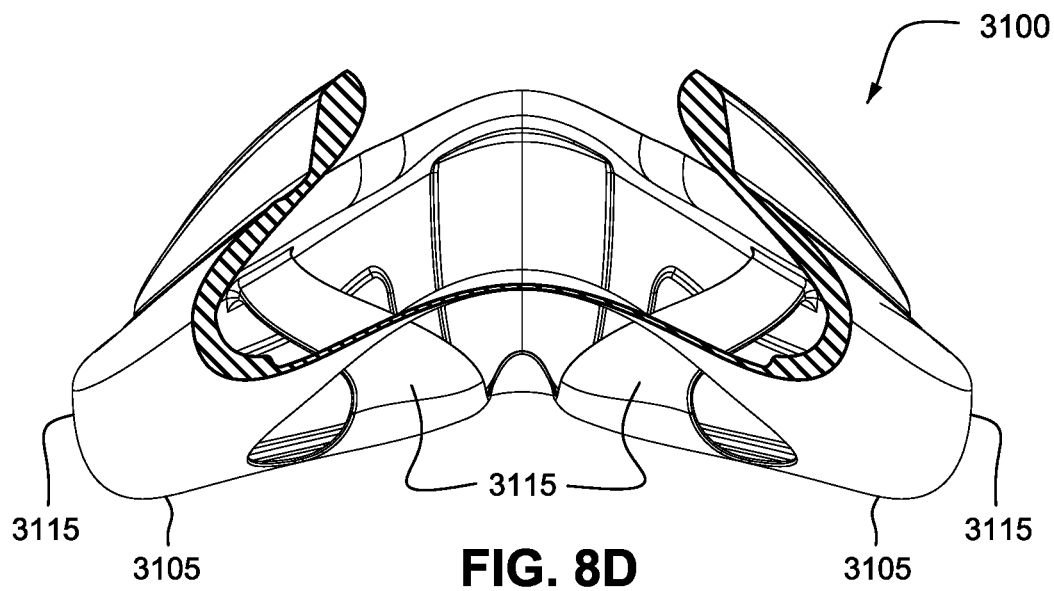
Figure 8E:
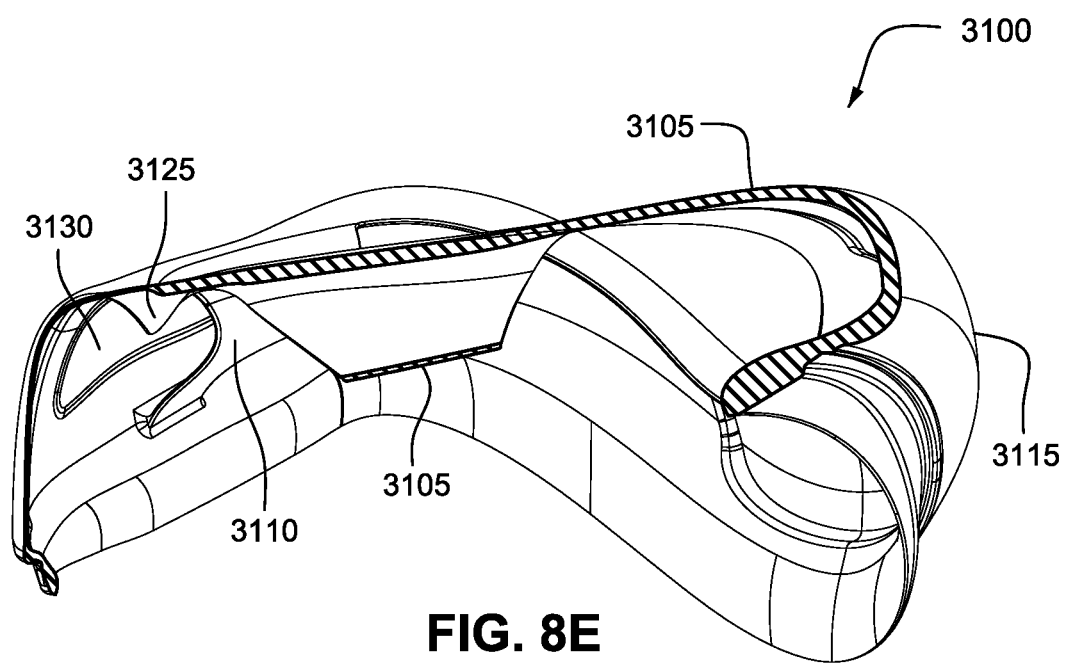
Figure 8F:
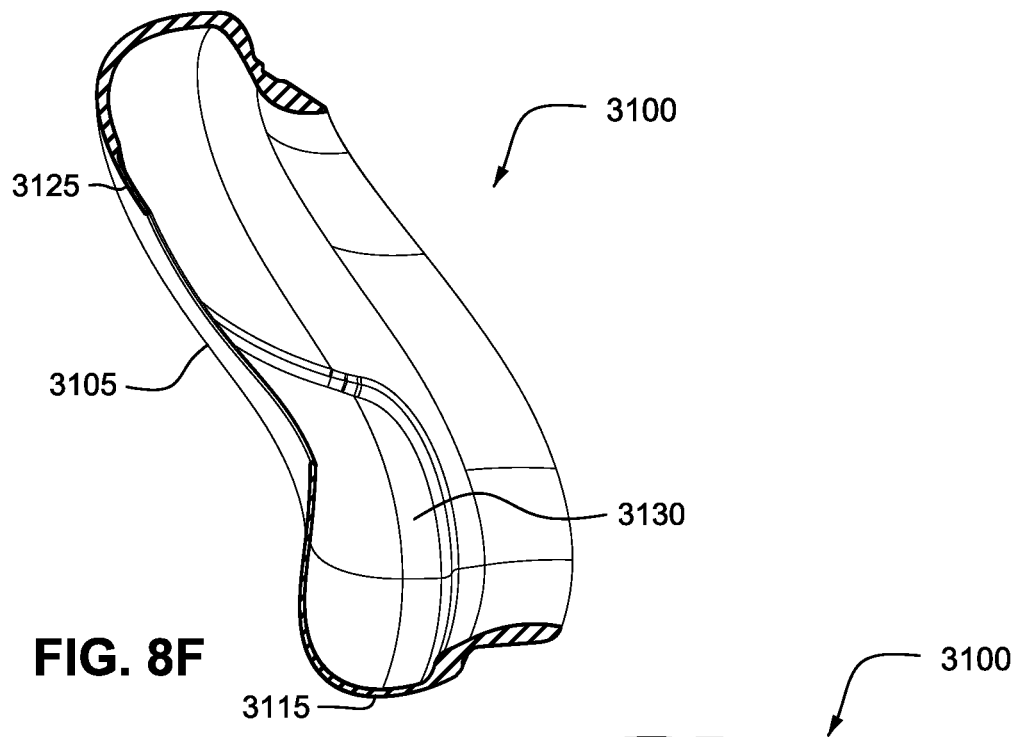
Figure 8G:
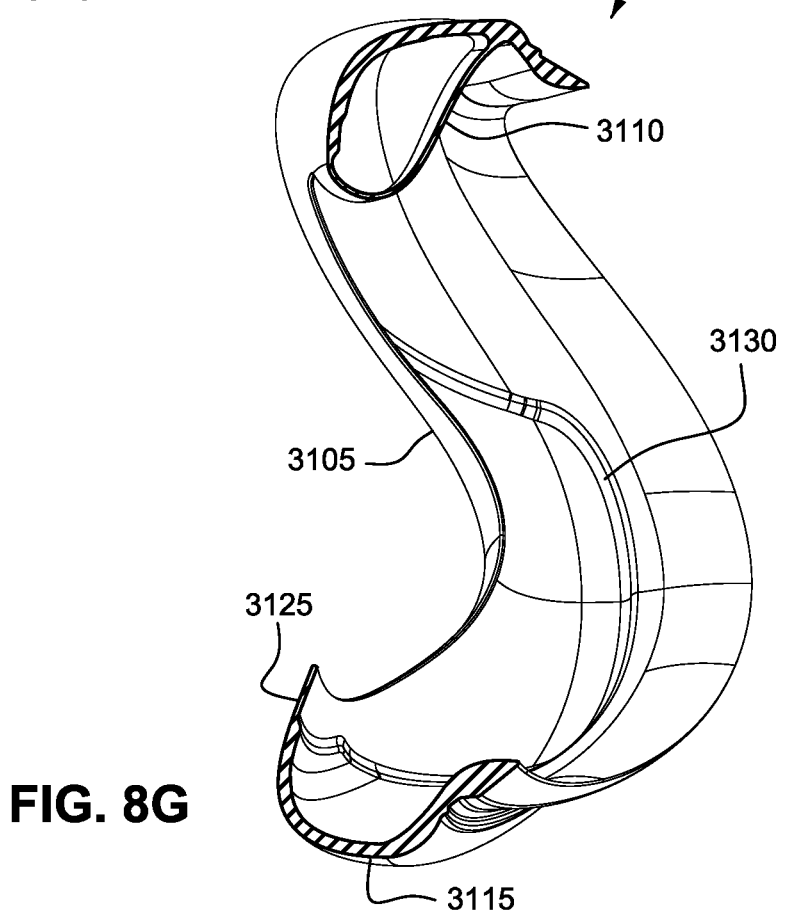

FIG. 8A illustrates a cross-section taken through a vertical plane in FIG. 6. As may be most readily seen in FIG. 8, the tie 3110 is attached to the wall forming the outer perimeter 3115 at an attachment portion 3145. As illustrated, the attachment portion 3145 is a continuous portion of the tie 3110, which can be achieved by moulding the seal forming structure 3100 in one piece. However, the attachment portion 3145 may also be achieved in any other convenient manner, e.g., by fastening a free end of the tie 3110 using some form of mechanical or chemical fastening like adhesive. The attachment portion 3145, along with the overall length of the tie 3110, may be chosen such that sufficient tension is provided to the tie 3110 to counteract a blowout of the sealing surface 3105 when pressure, e.g., therapy pressure, acts on an interior surface of the tie 3110 and the seal forming structure 3100 is pulled away from the patient's face and/or when insufficient headgear tension exists.

Some or all of the sealing surface 3105 may be a region of (relatively) reduced friction. This may be achieved by providing a so-called frosted surface. With a region of reduced friction, the sealing surface may adhere to the patient's face less than without the region of reduced friction. The region of reduced friction may be provided as part of the tie 3110 to allow the side(s) of the patient's nose to slide freely along the sealing surface 3105 and/or the tie 3110.

FIGS. 8A-8G also illustrate various cross-sections of FIG. 6 where the intersections of the cross-sections show that the seal forming structure 3100 includes various saddles and domes. For simplicity, the intersections of the various cross-sections are referred to herein by their two-letter combination. For example, the intersection of the cross-section taken along line 8A-8A and the cross-section taken along line 8B-8B is referred to as intersection AB.

Intersection AB is taken at a first dome region that is configured to contact the patient's nasal ridge inferior to the patient's sellion. Intersection AC is taken at a first saddle region that is configured to contact the patient's nasal ridge at a position inferior to intersection AB. Intersection AD is taken at a second saddle region that is configured to contact the patient's lip inferior and/or supramenton. Intersection EF is taken at a second dome region that is configured to contact the patient outside of but proximal to the patient's mouth, near the cheilion. Intersection EG is taken in a third saddle region that is configured to contact the patient's cheek adjacent the patient's nasal ala. In relation to one another, the first dome region has relatively large curvature along both cross sections and the second dome region has relatively small curvature along both cross section. The first saddle region has relatively large curvature along both cross-sections and the third saddle region has relatively small curvature along line 8E-8E and relatively large curvature along line 8G-8G. The second saddle region has curvature that is between the first saddle region and the third saddle region along line 8D-8D and line 8A-8A is similar to that along line 8G-8G.

FIG. 9 illustrates additional aspects of the present technology. For example, instead of the tie 3110 being continuous with the sealing surface 3105, FIG. 9 illustrates the tie 3110 underlying the sealing surface 3105. The tie 3110 is illustrated mostly as a dashed line. This configuration may be achieved by attaching or forming a strip or tube of material underneath the sealing surface 3105. The underlying tie 3110 may be more readily apparent in FIG. 10.

FIG. 9 also illustrates a flap 3150 that may extend from the sealing surface 3105 generally near the tie 3110 and/or the patient's nose. Such a flap 3150 may aid in sealing and/or comfort related to the patient's nose, above the maxilla and adjacent the endocanthion. This area of the patient's face may be difficult to seal with some known devices. Alternatively, the flap 3150 may extend from the tie 3110, which may fix the position of the flap 3150 with respect to the tie 3110. FIG. 11 illustrates a simplified representation of the tie 3110 as a substantially tube shaped structure 3120 with the flap 3150 extending therefrom.

FIG. 12 illustrates a simplified representation of the substantially tube-shaped structure 3120 illustrated in FIG. 11 attached to a seal forming structure 3100. In accordance with FIG. 12, the substantially tube-shaped structure 3120 may be fabricated separately and fastened to the seal forming structure 3100.

FIG. 13 illustrates how the substantially tube-shaped structure 3120 provides compliance to allow the seal forming structure 3100 to adapt to a patient's face. Even while compliant, the present technology may prevent a blowout.

Blowout may be understood to refer to the deformation of the seal forming structure 3100 that is caused, at least in part, by the pressure differential resulting from the application of pressure during therapy such that the sealing surface 3105 is displaced from sealing contact with the patient's face. For example, the patient may pull the patient interface 3000 away from the face during therapy (i.e., while pressure is being applied) and when the patient interface 3000 is displaced from the patient's face by the patient, the force of the therapy pressure may cause the seal forming structure 3100 to deform. When the patient interface 3000 is then reapplied to the patient's face by the patient, the sealing surface 3105 of the seal forming structure 3100 may be displaced due to deformation such that an ineffective seal is formed and pressurized gas leaks from the seal forming structure 3100. During this repositioning of the seal forming structure 3100, it is possible for the internal pressurisation of the plenum chamber 3200 to be disturbed and cause a pressure gradient proximal to the sealing flap 3125. The pressure gradient may provide a force, which may ultimately lead to blow out of the sealing flap. Displacement of the sealing flap during blow out may move the sealing flap into a position that interrupts seal by forming leak paths when the sealing structure is again repositioned onto the face. When blowout of the seal forming structure 3100 occurs at regions proximal to the patient's eyes (e.g., when the sealing surface 3105 proximal to the frontal process of the maxilla is displaced), the pressurized gas may flow towards the patient's, which may be particularly disruptive and bothersome to the patient. Accordingly, it is advantageous to reduce blowout.

The deformation that blowout may subject the seal forming structure 3100 to may be in an outward direction, e.g., away from the patient's face. Indeed, in extreme conditions under high internal pressurisation, blow out may include the seal forming structure 3100 folding backwards upon itself.

The sides of the nose, including above the nasal bones, proximal to the frontal process of the maxilla, and lateral cartilage can be highly variable in profile between users. Moreover, to seal in this region the inner edge of the sealing flap 3125 may bend inwards (e.g., into the plenum chamber and orthogonal to the Frankfort horizontal) and deform to follow the profile of the sides of the nose. As such, this area may be particularly prone to seal interruptions following blow out. That is, if the sealing flap 3125 is outwardly displaced (e.g., away from the patient's face) during blow out, it is often difficult to return the sealing flap to a sealing position due to resistance from the force of the pressurized gas.

However, blow out may also occur in other areas such as the cheek region or at the upper or lower lip regions which are less prone to seal interruption, but these regions have a generally flatter profile substantially along the coronal plane. During blow out, the sealing flap may not move significantly from a position that is required to seal along this plane and often the sealing force provided by the head gear vectors is sufficient to reposition the sealing flap to an orientation required to regain seal.

The posterior surface of the sealing flap at the sides of the nose region and down the bottom corners of the sealing flaps provides a larger surface area that is more prone to displacement under internal pressurisation.

While dual wall seal forming structures 3100 may be susceptible to blowout, single wall seal forming structures 3100 such as those disclosed in examples of the present technology, may be particularly susceptible to blowout. The absence of an additional undercushion structure supporting the outer, sealing wall may be understood to allow the outer, sealing wall to deform and deflect more easily. Moreover, the undercushion in a dual wall cushion may help to reposition the outer, sealing wall against the patient's face when the patient interface 3000 is repositioned, but this assistance may be absent in a single wall cushion.

FIGS. 34A and 34B depict examples of related art patient interfaces 3000 in which blowout has occurred. In FIG. 34A, the seal forming structure 3100 can be seen deformed such that the sealing surface 3105 at a blowout region BR1 is displaced from the patient's nose. Additionally, the seal forming structure 3100 can be seen deformed such that the sealing surface 3105 at another blowout region BR2 is displaced from the side of the patient's nose, e.g., proximal to the frontal process of the maxilla (see FIG. 2H). Similarly, FIG. 34B depicts displacement of the sealing surface 3105 of the seal forming structure 3200 at a blowout region BR2 at the side of the patient's nose, e.g., proximal to the frontal process of the maxilla.

In both examples of blowout described above, the patient interface 3000 is a full-face patient interface that seals around the nose and mouth. Such patient interfaces may be particularly susceptible to blowout because the relatively elongate lateral portions may be less supported at intermediate regions and blowout may occur in these regions. Additionally, the force vectors of the positioning and stabilising structure 3300 may be directed generally parallel to the Frankfort horizontal plane or the sagittal plane. Thus, these force vectors may not be directed to impart a force to the seal forming structure 3100 that is generally normal to the frontal process of the maxilla in an inward direction to thereby resist the deformation of the seal forming structure 3100 that results in blowout. In other words, the force of the therapy pressure that causes deformation of the seal forming structure 3100 may have a magnitude and direction that cannot be adequately opposed by the force vectors from the positioning and stabilizing structure 3100. While the phenomenon of blowout may be especially relevant for full-face patient interfaces, it should also be understood that nasal patient interfaces may also be susceptible to blowout based on the same principles. Accordingly, the ties 3110 disclosed herein may be incorporated with nasal and full-face patient interfaces to resist blowout.

Furthermore, there is also a relevant distinction in the context of the sealing surface 3105. The sealing surface 3105 may be understood to broadly refer to the region on the seal forming structure 3100 where a seal may be intended to occur. Since the anthropometry of each patient's head and face is different, the seal forming structure 3100 may be shaped and dimensioned to provide a comfortable fit and effective seal across a range of patients. Therefore, it should be understood that a seal may be intended to occur across various areas of the seal forming structure 3100 and the sealing surface 3105 may broadly refer to such areas. Once the seal forming structure 3100 is actually applied to a particular patient in use, a seal may be formed at a specific portion of the broader area in which a seal is intended to occur. That region at which the seal actually occurs in use may also be understood to be the sealing surface 3105. The particular meaning of the sealing surface 3105 may be understood to be subject to the particular contexts in which the term is used, as described above.

Referring back to the blowout discussion above, the occurrence of blowout may be understood to refer to the situation in which the sealing surface 3105 where a seal is intended to occur is displaced from the patient's face. When such displacement occurs, at least an effective seal may be prevented and, more severely, no sealing contact may occur at all.

FIG. 14 illustrates another aspect of the present technology that may prevent the seal forming structure 3100 from a blowout. Here, two ribs 3155 are illustrated but any number of ribs may be provided. For example, a single rib or three or more ribs may be provided. Similar to the tie 3110, each rib 3155 tends to prevent the seal forming structure 3100, for example the sealing surface 3105, from blowing out. The ribs may have the same thickness or different thicknesses. For example, one or both ribs 3155 may be about 1 mm thick and one or both ribs 3155 may be about 0.5 mm thick. Alternatively, the ribs may have a variable thickness. Where the ribs 3155 are attached, the sealing surface 3105 may be convex and an opposite side, where the ribs 3155 attach, may be concave. Thus the convex and concave surfaces define a thickness of material in that area. The ribs 3155 may be provided adjacent to a patient's nose.

FIG. 15 illustrates a cross section of the seal forming structure 3100 taken perpendicular to a plane of a rib 3155. The rib 3155 may be relatively compliant in compression or easily crushed under sealing loads, thus allowing seal forming structure 3100 and/or the sealing surface 3105 to adapt to the patient's face. This is illustrated in FIG. 16. However, as illustrated in FIG. 17, the rib 3155 may provide relatively greater resistance in tension, which may occur when the inside of the seal forming structure 3100, e.g., a surface 3105a opposed to the sealing surface 3105, is pressurized. In this manner, the rib 3155 may tend to resist blowout of the seal forming structure 3100, e.g., the rib 3155 may become a tensile member. For example, the ribs 3155 tend to keep the seal forming structure 3100 in an "as moulded" state or shape under a blow out condition.

FIGS. 18 and 19 illustrate an extended flap 3160 that may allow a greater distance D1 vs D2, to accommodate for facial variations where the distance between the sides of the nose and the sealing flap is varied. The sealing surface 3105 of the extended flap 3160 may also provide an effective seal against the cheeks. The arrows represent possible contact area with the patient. This type of structure is generally sealed using a membrane on traditional silicone masks and are prone to blow out when re-adjusting the position of the mask. The tie 3110 or rib 3155 may prevent blow out from happening while still allowing the variations in distance due to facial differences to be effectively sealed.

FIG. 20A illustrates a view similar to FIG. 6 except that patterns are included on the seal forming structure 3100. The patterns designate regions 3175 of similar thickness of the seal forming structure 3100.

Region 3175A may be a relatively thin region, for example, about 0.3 mm. This region may be thin for comfort and compliance at the nasal bridge.

Region 3175B may be a very thin region, for example, about 0.2 mm. This reduction in thickness relative to region 3175A may reduce tension significantly, which may result in minimal to no facial marking at the nasal bridge. The nasal bridge is quite bony for most patients and thus may be prone to marking and/or discomfort.

Region 3175C may be a semi-thin region, for example, about 1 mm. This region may be semi-thin to prevent pinching at the sides of the nose.

Region 3175D may be a semi-thick region, for example, about 1.5 mm. This region may seal on the cheeks alongside nose. This area on the face is typically fattier then the sides of the nose or nasal bridge, which allows for a relatively greater seal force to be applied without discomfort. The semi-thick region may also provide for more structural rigidity than thinner regions.

Region 3175E may be a thick region, for example, about 2.0 mm. This thicker peripheral region may provide a more rigid outer wall to provide support for the inner portion of the cushion. Region 3175E may act like an undercushion of prior dual layer cushion designs, e.g., the region 3175E may support the portion(s) of the seal forming structure 3100 that contacts the patient's face. For example, region 3175E may provide support to region 3175D and/or 3175F (discussed below). The overall cross sectional shape of the cushion may be curved to provide an air (pressure) assisted spring for seal and compliance. This configuration may provide an advantage over the previous thick undercushions of prior masks because the disclosed configuration with this thick region may still be able to compress to provide a level of compliance to support forming a seal. This may increase the overall distance range in which the cushion can compress when compared to previous dual layer designs.

Region 3175F may be a thin membrane region, for example, about 0.3-0.5 mm. The portion that seals below the lower lip may be thin, for example, about 0.3 mm, to allow for movement of the lower jaw. Such a thin membrane region may also provide a lighter load against the patient's gums for comfort. The portion of region 3175F adjacent region 3175D is where the ties 3110 are positioned. This portion of region 3175F may be thin, for example, about 0.5 mm, to allow compression of the ties 3110. The portion of region 3175F configured to contact on the sides of the patient's mouth may be about 0.5 mm and may act like the sealing membrane layer of the dual layer cushions, which maintain a seal with micro variations of the facial profile and movement during sleep.

Although distinct lines are illustrated between the regions 3175, the regions may smoothly transitions in relative thickness from region to region and thus the borders between regions are approximations. This may be advantageous because it limits the ability to identify thick and thin regions by the naked eye, which may also be more aesthetically pleasing. However, distinct transitions may also be provided.

FIG. 20B illustrates another seal forming structure 3100 with regions of similar elastomeric wall thickness of the seal forming structure 3100.

A region 3180A may be a relatively thin region, for example, about 0.3 mm elastomeric wall thickness. This region may be thin for comfort and compliance at the nasal bridge.

A region 3180B may be a very thin region, for example, about 0.2 mm elastomeric wall thickness. This reduction in thickness relative to region 3180A may reduce tension significantly, which may result in minimal to no facial marking at the nasal bridge. The nasal bridge is quite bony for most patients and thus may be prone to marking and/or discomfort. In addition, the region 3180A may extend from the region 3180B to a mask shell 3816 attached to the anterior side of the seal forming structure 3100.

Regions 3180A and 3180B may both straddle a sagittal plane 3185 that may bisect the seal forming structure 3100 into left and right sides. The sagittal plane 3185 may include a line 3190 that may be tangent to the seal forming structure 3100 at only two tangent points: a first tangent point (superior tangent point) 3195 and a second tangent point (inferior tangent point) 3196. Either region 3180A or region 3180B may include the first tangent point 3195. If not including the first tangent point 3195, the region 3180A or 3180B may be within the vicinity of the first tangent point 3195.

A portion of the region 3180B may also be configured to seal against the sides of the nose over the nasal bones and/or lateral cartilage. The portion of the region 3180B may be configured to, in use, contact the sides of the nose and/or the lateral cartilage prior to the seal forming structure contacting other parts of the face to form a seal. The portion of the region 3180B may also be very thin to prevent excessive force and pinching at the sides of the nose to avoid occlusion of the airways.

In addition, a central opening 3197 defined by a posterior side of the seal forming structure 3100 may be narrower in the region 3180B so that the seal forming structure 3100 is more compliant in the direction toward and away from the sides of the patient's nose (i.e., along a plane that is orthogonal to the sagittal plane 3185).

A region 3180C may be a semi-thin region, for example, about 0.85 mm. This region may be semi-thin to prevent pinching at the sides of the nose. In addition, the region 3180C may border on both the region 3180A and the region 3180B.

A region 3180D may be a transition region in which the elastomeric wall thickness varies. In particular, the elastomeric wall thickness of the seal forming structure 3100 in the region 3180D may decrease the direction toward the central opening 3197. For example, the elastomeric wall thickness may decrease from about 2.0 mm to 1.3 mm. The change in elastomeric wall thickness may be gradual or abrupt. In addition, the region 3180D may border on the regions 3180A and 3180C but not the region 3180B.

The tie 3110 may extend from the region 3180D and/or the region 3180C.

A region 3180E may be a thick region, for example, about 2.0 mm elastomeric wall thickness. This thicker peripheral region may provide a more rigid outer wall to provide support for the inner portion of the cushion. The region 3180E may act like an undercushion of prior dual layer cushion designs, e.g., the region 3180E may support the portion(s) of the seal forming structure 3100 that contacts the patient's face. In addition, the region 3180E may border on the regions 3180D and 3180A but not the regions 3180B and 3180C.

The overall cross sectional shape of the cushion may be curved to provide an air (pressure) assisted spring for seal and compliance. This configuration may provide an advantage over the previous thick undercushions of prior masks because the disclosed configuration with this thick region may still be able to compress to provide a level of compliance to support forming a seal. This may increase the overall distance range in which the cushion can compress when compared to previous dual layer designs.

The region 3180F may be a semi-thick region, for example, about 1.3 mm elastomeric wall thickness. This region may seal on the cheeks alongside the mouth. This area on the face is typically fattier then the sides of the nose or nasal bridge, which allows for a relatively greater seal force to be applied without discomfort. The semi-thick region may also provide for more structural rigidity than thinner regions. The region 3180*f* may border on the region 3180D and the region 3180C but not the regions 3180A, 3180B or 3180E.

The region 3180G may be a thin membrane region, for example, about 0.3 mm elastomeric wall thickness. The portion that seals below the lower lip may be thin to allow for movement of the lower jaw. Such a thin membrane region may also provide a lighter load against the patient's gums for comfort. The region 3180G may act like the sealing membrane layer of the dual layer cushions, which maintain a seal with micro variations of the facial profile and movement during sleep. In addition, the region 3180G may extend from the central opening 3197 to the mask shell 3816 attached to the anterior side of the seal forming structure 3100. The region 3180G may also border on the region 3180D, the region 3180E and the region 3180F but not the regions 3180A, 3180B or 3180C.

A region 3180H may be a flap region extending from the tie 3110. The elastomeric wall thickness in the region 3180H may be 0.5 mm. In addition, the region 3180H may be configured to move independently of the tie 3110. The region 3180H may border the region 3180B, the region 3180C and the region 3180F but not the regions 3180A, 3180D, 3180E or 3180G.

Although distinct lines are illustrated between the regions 3175, the regions may smoothly transitions in relative thickness from region to region and thus the borders between regions are approximations. This may be advantageous because it limits the ability to identify thick and thin regions by the naked eye, which may also be more aesthetically pleasing. However, distinct transitions may also be provided.

In view of FIGS. 8A-8G, it should be understood that the regions 3180A through 3180H have various curvatures. For example, at least a portion of the region 3180A may be a dome-shaped region, while the region 3180B may have a saddle shape. In addition, various portions of the regions 3180C, 3180D, 3180E, 3180F and 3180H may be saddle-shaped, dome-shaped or cylinder-shaped. In addition, the region 3180G may be saddle-shaped.

FIG. 20C illustrates the sealing surface 3105. A region 3198A in the upper portion of the sealing surface 3105 may have relatively reduced friction. This may be achieved by providing a so-called frosted surface. With a region of reduced friction, the sealing surface may adhere to the patient's face less than without the region of reduced friction. The region of reduced friction may be provided as part of the tie 3110 to allow the side(s) of the patient's nose to slide freely along the sealing surface 3105 and/or the tie 3110. The region 3198B in the remaining portion of the sealing surface 3105. The tackier surface may prevent or reduce the likelihood of leakage due to movement of the patient's chin.

FIG. 20C also shows a plurality of closed paths 3199A on the continuous surface around the central opening 3197. The closed paths 3199A may be concentric to the central opening 3197. For the purposes of this disclosure, paths that are concentric to the central opening 3197 may substantially follow the shape of the central opening 3197 and may be a particular distance from the central opening 3197 throughout the path when viewed head-on (i.e., the point of view shown in FIG. 20C). FIG. 20C also shows one of the plurality of open paths 3199B extending from the central opening 3197 to the mask shell 3816.

International Patent Application Publication No. WO 2006/074513 discloses cushions, which are incorporated by reference in their entirety. In such cushions, a thicker undercushion and thinner membrane layer are disclosed. The thinner membrane provides a light seal on the face under pressure (i.e. inflates), while the undercushion provides structural support to support sealing. The curved cross section provides a pressure assisted spring to support seal under headgear tension.

In contrast, a seal forming structure 3100 with the one or more of the regions 3175 described above may have only a single layer, which may combine functions of the membrane and undercushion of WO 2006/074513. The maximum thickness of the cross section of the regions 3175 (e.g., region 3175E) may be thinner than the maximum thickness of the undercushion of WO 2006/074513. However, combining the undercushion and membrane into a single layer allows for sufficient structural rigidity to hold the shape of the cushion and support sealing action. Moreover, the reduced maximum thickness allows the single layer of the seal forming structure 3100 to be compressible by a greater distance compared to the previous dual layer design, thereby allowing for added compliance before bottoming out.

International Patent Application Publication WO 2014/117227 discloses a system with a mask where a foam cushion is supported by a flexible clip that is attached to a second, more rigid clip, each of which is hereby incorporated by reference in its entirety. FIG. 21 discloses a similar system but with two ribs 3155 having been incorporated, where the ribs configured to be on opposed sides of a patient's nose. Only one rib is visible in FIG. 21. These ribs act as ties that prevent the flexible clip and attached foam seal from blowing out. Although ribs 3155 are illustrated, ties 3110 could be substituted for the ribs 3155.

Thus, in another example of the present technology, the seal forming structure 3100 may comprise a cushion 3810, which may be made with foam. The cushion defines a single area that peripherally covers the patient's nose, in the case of a nasal mask, and the nose and mouth, in the case of a full face mask. The foam cushion may, for example, be made from any suitable material such as one or more of the following example materials: Polyethylene, Polyurethane, Ethylene vinyl acetate (EVA). In some cases, the foam cushion may be a semi-open closed cell foam, such as one made of polyurethane. The cushion of semi-open cell foam may have a limited permeability such as in the ranges described in more detail in International Patent Application Publication WO 2014/117227, where the permeability disclosed therein is incorporated herein by reference.

The cushion 3810 may have a substantially triangular or pear-like shape with a sealing face that follows the contours of a user's face. The foam cushion is designed to be attached to a first support (e.g., flexible) clip 3812 that is itself attached to a second, more rigid, clip 3814 (as shown in FIG. 22) or directly to the mask shell 3816. In one embodiment, the first support clip 3812 can be a flexible clip that is more rigid than the foam cushion, but softer or more flexible than the second clip 3814. It is the combination of the foam and a flexible clip that define the physical properties of the overall sealing interface. The flexible clip allows the interface to accommodate major variations, and to successfully conform to the contours of the patient's face. The compliant nature of the foam cushion provides micro-adjustment and forms a comfort interface layer that interacts with the patient's skin.

The first support clip 3812 may be prone to blowing out due to its flexible and compliant nature. FIG. 21 illustrates another aspect of the present technology that may prevent the first support clip 3812 and the attached cushion 3810 from a blowout. Here, the configuration illustrated includes two ribs 3155 (only one being visible due to the symmetric nature and orientation of the figure) but any number of ribs may be provided. For example, a single rib or three or more ribs may be provided. Similar to the tie 3110, each rib 3155 tends to prevent the first support clip 3812 and the attached cushion 3810 from blowing out by functioning as a tensile member. The ribs may have the same thickness or different thicknesses. For example, one or both ribs 3155 may be about 1 mm thick and one or both ribs 3155 may be about 0.5 mm thick. Alternatively, the ribs may have a variable thickness. The ribs 3155 may be provided adjacent to a patient's nose.

FIG. 21 illustrates a side view of a cushion assembly 3800 comprising the seal forming structure 3100 including a mask shell 3816, a permanently attached flexible first supporting clip 3812 and a foam cushion 3810. As illustrated, the flexible first supporting clip may be fixed to the mask shell 3816 via a pair of ribs 3155 that act as ties to prevent blow out. The ribs 3155 may be relatively compliant in compression or easily crushed under sealing loads, thus allowing the seal forming structure 3100 to adapt to the patient's face. The tension provided by the ribs 3155 may be adjusted by altering any one or more of its material composition, geometry or position of the ribs 3155.

FIG. 23 illustrates the foam cushion 3810 and flexible first supporting clip 3812 where the patient contacting surface is visible. FIG. 23A is a cross-section taken along a vertical plane of symmetry through FIG. 23 and illustrates the foam cushion, flexible first supporting clip 3812 and rib 3155.

In another example of the present technology, the seal forming structure 3100 may comprise a pair of ties 3110 to prevent blow out of the first support clip 3812. Each tie 3110 is formed by an inward fold of the flexible supporting clip 3812 of an outer perimeter to form a connection point 3165. In this manner, the tie 3110 may form a substantially tube-shaped structure 3120. The tie forms a tie to resist blowing out from internal pressurisation of the plenum chamber. The tension provided by the ribs 3155 may be adjusted by altering any one or more of its material composition, geometry or position of the connection point 3165 of position the tie 3110.

FIGS. 24-27 illustrate a seal forming structure 6000 similar to the seal forming structure 3100 except as noted herein. Like reference numbers are similar to those described above regarding the seal forming structure 3100 and thus further description not repeated here. The seal forming structure 6000 illustrated in FIGS. 24-27 may have features generally suitable for use with a nasal mask.

FIGS. 25B-25G also illustrate various cross-sections of FIG. 25A where the intersections of the cross-sections show that the seal forming structure 6000 includes various saddles and domes. For simplicity, the intersections of the various cross-sections are referred to herein by their two-letter combination. For example, the intersection of the cross-section taken along line 25B-25B and the cross-section taken along line 25C-25C is referred to as intersection BC.

Intersection BC is taken at a first saddle region that is configured to contact the patient's nasal ridge inferior to the patient's sellion. Along line 25B-25B, the curvature is relatively small and along line 25C-25C the curvature is relatively large. The curvature along line 25B-25B is sufficiently large that the first saddle region is approaching a cylindrical region. The first saddle region may be a cylindrical region if so desired. Intersection BD is taken at a second saddle region that is configured to contact the patient's lip superior. Along line 25B-25B the curvature is relatively small compared to along line 25D-25D. Intersection CF is taken at a first dome region that is configured to contact the patient's nose adjacent the nasal ridge. Along line 25F-25F the and along line 25C-25C the curvatures are relatively similar. Intersection FG is taken at a third saddle region formed by the tie 3110 that is configured to contact alongside the patient's nose. The curvature along line 25F-25F is relatively small and is approaching zero curvature. The curvature along line 25G-25G is relatively large comparted to line 25F-25F. Thus the third saddle region is approaching a cylindrical region and thus may be a cylindrical region if preferred. Intersection EF is taken at a second dome region that is configured to contact the patient alongside the patient's nasal alar. The curvatures along lines 22E-22D and 22F-22F are relatively similar.

FIG. 27 illustrates a view of the seal forming structure 6000 except that patterns are included on the seal forming structure 6000. The patterns designate regions 6005 of similar properties and/or thickness of the seal forming structure 6000.

Region 6005A, referred to herein as a nasal region, may have a thickness of about 0.5 mm, which may prevent crinkling and/or creasing of the seal forming structure 6000 in this region.

Region 6005B, referred to herein as a base region, may have a thickness between about 2.9 mm to 3.45 mm. For example, the thickness may be 2.9 mm at 6005B2, 3.0 mm at 6005B1 and 6005B3 and 3.45 mm at 6005B4. Region 6005B may provide a support or base for the sealing flap 3125 and may provide and maintain the overall shape of the seal forming structure 6000.

Region 6005C, referred to herein as an under-cushion zone, may have a thickness ranging from 0.95 mm to 2.1 mm. As illustrated, this region may be the predominant region of the cushion. For example, region 6005C may be approximately 50% of the cushion. Thickness of the upper portion of the region 6005C1 may be between 0.95 mm and 1.6 mm whereas thickness of the lower portion of the region 6005C2 may be between 1.25 mm and 2.1 mm. The thickness may be continuously varying between these values to provide a smooth appearance.

Region 6005D, referred to herein as a membrane region, may form approximately one third of the seal forming structure 6000 and may include the ties 3110. The thickness may be about 0.35 mm. This region may be relatively thin so that it may function as an energized (e.g., pressure activated) seal against the patient's face. The side sections 6005D1 may be substantially parallel to the patient's face, which may reduce the likelihood of creasing and thus causing a leak. Such creases may be more likely to occur during dynamic situations, e.g., when the seal is under movement.

Region 6005F, referred to herein as a spring zone, may have a thickness ranging from 1.1 mm to 1.8 mm. This zone may function as a spring and allow for compression on the lip superior to reduce pressure thereon. This region may get progressively stiffer from the center of the lip superior to the corners of the nose (e.g., the alar crest point) where region 6005F is stiffest.

Region 6005G, referred to herein as a nose dip region, may be relatively deeper to better accommodate patients that have a relatively high nasal bridge and/or provide a more comfortable seal. This region may have a thickness similar to that of region 6005D (e.g., about 0.35 mm) and thus may be a sub-region of region 6005D.

The expressions "soft" and "flexible", as well as their derivatives, when used in this specification to describe the first support clip 3812, are intended to have the meaning of the expression "resilient" as specifically defined in section "Terms used in relation to patient interface". This is to say, the flexible supporting clip is able to deform substantially elastically, and to quickly release substantially all of the energy upon unloading.

The seal forming structure 3100 may have advantages in one or more forms of the present technology. For example, the human facial structure may include variations from person to person that provide challenges when designing a seal for use with many facial variations. The variations may include different shapes of the facial structure (e.g., differently shaped noses and/or differently curved cheeks) and/or different tissue content (e.g., more or less fatty tissue). These variations may result in a prior seal forming structure that works very well for one person but poorly for another. Also, perceived comfort may vary from person to person independent of facial structure. With the seal forming structure 3100 described herein, a higher percentage of users may use the seal forming structure 3100 effectively (e.g., a higher percentage of users may have the seal forming structure 3100 form an effective seal and/or a higher percentage of users may perceive the seal forming structure 3100 to be comfortable) than compared to prior seal forming structures.

FIGS. 28A to 28M depict an exemplary full-face seal forming structure 3100 that includes the ties 3110. As can be seen in FIG. 28K, for example, the ties 3110 may extend between a first interior surface region 3180 and a second interior surface region 3185. The first interior surface region 3180 may be understood to be opposite the sealing surface 3105 of the seal forming structure. The second interior surface region 3185 may be understood to be located elsewhere. In the example depicted in FIG. 28k, the second interior surface region 3185 is located on the interior of the seal forming structure 3100. In other examples, the second interior surface region 3185 may be located on the interior of the plenum chamber 3200 such that the tie 3110 extends between the seal forming structure 3100 and the plenum chamber 3200. The location of the second interior surface region 3185 may be selected based on the desired directional component of the tension vector of the tie 3110 that resists the blowout force.

FIGS. 28L and 28M show detailed cross-sectional views and, in particular, the connection point 3165 where the tie 3110 extends from the second interior surface region 3165. The connection point 3165 in this example may be curved to reduce stress concentration in this region, thereby reducing the tendency for the tie 3110 to tear. Furthermore, the tie 3110 may extend from the second interior surface region 3185 at a distance from a bonding region 3190 where the seal forming structure 3100 is bonded to the plenum chamber 3200 during production. This may prevent damage to the tie 3110 when the seal forming structure 3100 is bonded to the plenum chamber 3200. FIGS. 29C to 29E also show how the tie 3110 extends from the second interior surface region 3185 at a distance from the bonding region 3190 and the plenum chamber 3200.

The cross-sectional views of FIGS. 28J to 28L also show where the tie 3110 may extend from the first interior surface region 3180. As can be seen in these examples, the tie 3110 extends from the first interior surface region 3180 near, but not at the edge of the sealing flap 3125. However, in alternative examples the tie 3110 may extend from the first interior surface region 3180 closer to or at the edge of the sealing flap 3125.

FIGS. 30A and 30B depict examples of a full-face patient interface 3000 including a seal forming structure 3100 with features of the present technology, but without a positioning and stabilizing structure 3300 depicted.

FIGS. 31A to 31M depict another example of the present technology which is a nasal seal forming structure 3100. As can be seen in FIG. 31K, for example, the tie 3110 extends contiguously from the sealing flap 3125. Accordingly, there may not be a defined edge in this region. Moreover, it should also be understood that at least a portion of the tie 3110 in such an arrangement may form part of the sealing surface 3105 in use, depending on the patient's facial anthropometry.

FIGS. 32C to 32E show that in the nasal patient interface 3000 example that the tie 3110 may extend from the second interior surface region 3185 at a further distance from the bonding region 3190 as compared to the full-face patient interface 3000.

4.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

4.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises tie material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another. suitable for a small sized head, but not a large sized head.

4.3.4 Vent

In one form, the patient interface 3000 includes a vent 3400 constructed and arranged to allow for the washout of exhaled gases, e.g. carbon dioxide.

One form of the vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

4.3.5 Decoupling Structure(s)

In one form the patient interface 3000 includes at least one decoupling structure, for example, a swivel or a ball and socket.

4.3.6 Connection Port

Connection port 3600 allows for connection to the air circuit 4170.

4.3.7 Forehead Support

In one form, the patient interface 3000 includes a forehead support 3700.

4.3.8 Anti-Asphyxia Valve

In one form, the patient interface 3000 includes an anti-asphyxia valve.

4.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

4.4 RPT DEVICE

An RPT device 4000 in accordance with one aspect of the present technology comprises mechanical, pneumatic, and/or electrical components and is configured to execute one or more algorithms 4300. The RPT device 4000 may be configured to generate a flow of air for delivery to a patient's airways, such as to treat one or more of the respiratory conditions described elsewhere in the present document.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.4.1 RPT Device Mechanical & Pneumatic Components

An RPT device may comprise one or more of the following components in an integral unit. In an alternative form, one or more of the following components may be located as respective separate units.

4.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

4.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

4.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

4.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

4.4.2 RPT Device Electrical Components

4.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

4.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to a central controller.

4.4.2.3 Output Devices Including Optional Display, Alarms

An output device in accordance with the present technology may take the form of one or more of a visual, audio and haptic unit. A visual display may be a Liquid Crystal Display (LCD) or Light Emitting Diode (LED) display.

4.5 AIR CIRCUIT

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

4.6 HUMIDIFIER

4.6.1 Humidifier Overview

In one form of the present technology there is provided a humidifier 5000 (e.g. as shown in FIGS. 3V and 3W) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 3V and FIG. 3W, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.6.2 Humidifier Components

4.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 3V and FIG. 3W.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

4.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

4.6.2.3 Humidifier Reservoir Dock

In one form, the humidifier 5000 may comprise a humidifier reservoir dock 5130 (as shown in FIG. 3V) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

4.6.2.4 Water Level Indicator

The humidifier reservoir 5110 may comprise a water level indicator 5150 as shown in FIG. 3V-3W. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

4.6.2.5 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

4.7 GLOSSARY

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water (H2O) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including cmH$_2$O, g-f/cm$^2$ and hectopascal. 1 cmH$_2$O is equal to 1 g-f/cm$^2$ and is approximately 0.98 hectopascal. In this specification, unless otherwise stated, pressure is given in units of cmH$_2$O.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

4.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

4.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

4.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.7.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

4.7.4 Anatomy 4.7.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 4.7.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.7.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.7.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example, the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.7.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a cushion structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

4.7.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill) See FIG. 3E (relatively small negative curvature compared to FIG. 3F) and FIG. 3F (relatively large negative curvature compared to FIG. 3E). Such curves are often referred to as convex.

4.7.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

4.7.6.3 Space Curves

Space curves: Unlike a plane curve, a space curve does not necessarily lie in any particular plane. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

4.7.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

4.8 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

4.9 REFERENCE SIGNS LIST 1000 patient
1100 bed partner
3000 patient interface
3100 seal-forming structure
3105 sealing surface
3110 tie
3111 end
3115 outer perimeter
3120 tube-shaped structure
3125 sealing flap
3130 thick portion
3135 thin portion
3140 hinge structure
3145 attachment portion
3150 flap
3155 rib
3160 flap
3165 connection point
3170 angle
3175 region
3175A region
3175B region
3175C region
3175D region
3175E region
3175F region
3180A region
3180B region
3180C region
3180D region
3180E region
3180F region
3180G region
3180H region
3185 sagittal plane
3190 line
3195 first tangent
3196 second tangent
3197 central opening
3198A region
3198B region
3199A closed path
3199B open path
3200 plenum chamber
3210 perimeter
3220 marginal edge
3300 structure
3400 vent
3600 connection port
3700 forehead support
3800 cushion assembly
3810 cushion
3810 foam cushion
3812 flexible supporting clip
3814 second clip
3816 mask shell
4000 RPT device
4170 air circuit
5000 humidifier
6000 structure
6005 region
6005A region
6005B region
6005C region
6005D region
6005F region
6005G region

The invention claimed is:

1. A cushion assembly for a patient interface for sealed delivery of a flow of air at a continuously positive pressure with respect to ambient air pressure to an entrance to a patient's airways including at least entrance of the patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing, the cushion assembly comprising:

an elastomeric seal-forming portion that is bisected by a sagittal plane that includes a line tangent to the elastomeric seal-forming portion at a superior tangent point and at an inferior tangent point, the elastomeric seal-forming portion terminating at an unsupported edge and forming at least part of a plenum chamber, the elastomeric seal-forming portion having an interior surface inside the plenum chamber and an exterior surface outside the plenum chamber, the elastomeric seal-forming portion comprising:

a superior region that is intersected by the sagittal plane in the vicinity of the superior tangent point, the exterior surface of the elastomeric seal-forming portion at the superior region being dome-shaped;

an inferior region that is intersected by the sagittal plane and includes the inferior tangent point, the exterior surface of the elastomeric seal-forming portion at the inferior region being saddle-shaped; and a first support region located on one side of the sagittal plane between the inferior region and the superior region, the exterior surface of the elastomeric seal-forming portion at the first support region being cylinder-shaped and/or saddle-shaped; and a blowout prevention system configured to counter a force acting on the unsupported edge of the elastomeric seal-forming portion due to a pressure within the plenum chamber, the blowout prevention system comprising a tie with opposing ends that are attached to the first support region of the elastomeric seal-forming portion and a middle portion between the opposing ends, the middle portion being separated from the elastomeric seal-forming portion so that gas in the plenum chamber is allowed to flow between the tie and the elastomeric seal-forming portion.

2. The cushion assembly of claim 1, wherein the exterior surface of the elastomeric seal-forming portion is dome-shaped between the first support region and the inferior region.

3. The cushion assembly of claim 1, wherein the tie is elastomeric.

4. The cushion assembly of claim 1, wherein the unsupported edge of the elastomeric seal-forming portion extends inwardly beyond the tie.

5. The cushion assembly of claim 1, wherein the tie is configured to be positioned alongside the patient's nose above the patient's nasal base in use.

6. The cushion assembly of claim 1, wherein the elastomeric seal-forming portion further comprises a second support region located on an opposite side of the sagittal plane from the first support region between the inferior region and the superior region, the exterior surface of the elastomeric seal forming portion at the second support region being cylinder-shaped and/or saddle-shaped.

7. The cushion assembly of claim 6, wherein the tie of the blowout prevention system is a first tie, and wherein the blowout prevention system further comprises a second tie with opposing ends that are attached to the second support region of the elastomeric seal-forming portion and a middle portion between the opposing ends, the middle portion of the second tie being separated from the elastomeric seal-forming portion so that gas in the plenum chamber is allowed to flow between the second tie and the elastomeric seal-forming portion.

8. The cushion assembly of claim 7, wherein the exterior surface of the elastomeric seal-forming portion is dome-shaped between the second support region and the inferior region.

9. The cushion assembly of claim 8, wherein the second tie is elastomeric.

10. The cushion assembly of claim 8, wherein the unsupported edge of the elastomeric seal-forming portion extends inwardly beyond the second tie.

11. The cushion assembly of claim 8, wherein the second tie is configured to be positioned alongside the patient's nose above the patient's nasal base in use.

12. The cushion assembly of claim 1, wherein the tie of the blowout prevention system is a first tie and the blowout prevention system further comprises a second tie, wherein the elastomeric seal-forming portion further comprises a second support region located on an opposite side of the sagittal plane from the first support region between the inferior region and the superior region, wherein the second tie comprises opposing ends that are attached to the second support region of the elastomeric seal-forming portion and a middle portion between the opposing ends, the middle portion of the second tie being separated from the elastomeric seal-forming portion so that gas in the plenum chamber is allowed to flow between the second tie and the elastomeric seal-forming portion, wherein the exterior surface of the elastomeric seal-forming portion is dome-shaped between the first support region and the inferior region, wherein the first tie and the second tie are elastomeric, wherein the unsupported edge of the elastomeric seal-forming portion extends inwardly beyond the first tie, wherein the first tie is configured to be positioned alongside the patient's nose above the patient's nasal base in use, wherein the exterior surface of the elastomeric seal-forming portion at the second support region is cylinder-shaped and/or saddle-shaped, wherein the exterior surface of the elastomeric seal-forming portion is dome-shaped between the second support region and the inferior region, wherein the unsupported edge of the elastomeric seal-forming portion extends inwardly beyond the second tie, and wherein the second tie is configured to be positioned alongside the patient's nose above the patient's nasal base in use.

13. A patient interface comprising:
the cushion assembly of claim 1;
a rigid shell removably connected to the cushion assembly; and
headgear removably attached to the rigid shell.

14. A CPAP system comprising:
the patient interface according to claim 13;
a flow generator configured to pressurize a flow of gas; and
an air delivery tube configured to deliver the pressurized gas to the patient interface.

15. A cushion assembly for a patient interface for sealed delivery of a flow of air at a continuously positive pressure with respect to ambient air pressure to an entrance to a patient's airways including at least entrance of the patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing, the cushion assembly comprising:

an elastomeric seal-forming portion that is bisected by a sagittal plane that includes a line tangent to the elastomeric seal-forming portion at a superior tangent point and at an inferior tangent point, the elastomeric seal-forming portion terminating at an unsupported edge and forming at least part of a plenum chamber, the elastomeric seal-forming portion having an interior surface inside the plenum chamber and an exterior surface outside the plenum chamber, the elastomeric seal-forming portion comprising:

a superior region that is intersected by the sagittal plane in the vicinity of the superior tangent point;

an inferior region that is intersected by the sagittal plane and includes the inferior tangent point;

a first support region located on one side of the sagittal plane between the inferior region and the superior region; and a second support region located on an opposite side of the sagittal plane from the first support region between the inferior region and the superior region; and a blowout prevention system configured to counter a force acting on the unsupported edge of the elastomeric seal-forming portion due to a pressure within the plenum chamber, the blowout prevention system being attached to the elastomeric seal-forming portion at the first support region and the second support region of the elastomeric seal-forming portion, wherein a part of the exterior surface of the elastomeric seal-forming portion in the inferior region is tackier than a part of the exterior surface of the elastomeric seal-forming portion in the superior region.

16. The cushion assembly of claim 15, wherein the blowout prevention system is attached to the elastomeric seal-forming portion at a region where the exterior surface of the elastomeric seal-forming portion is relatively less tacky than the tackiness in the inferior region.

17. The cushion assembly of claim 15, wherein a transition from the relatively tackier exterior surface of the elastomeric seal-forming portion to the relatively less tacky surface is located in the first support region.

18. The cushion assembly of claim 15, wherein a transition from the relatively tackier exterior surface of the elastomeric seal-forming portion to the relatively less tacky surface is located in the second support region.

19. The cushion assembly of claim 15, wherein a transition from the relatively tackier exterior surface of the elastomeric seal-forming portion to the relatively less tacky surface is located at the unsupported edge of the elastomeric seal-forming portion.

20. The cushion assembly of claim 15, wherein the blowout prevention system comprises a first tie anchored to the elastomeric seal-forming portion at the first support region and a second tie anchored to the elastomeric seal-forming portion at the second support region.

21. The cushion assembly of claim 20, wherein the unsupported edge of the elastomeric seal-forming portion extends inwardly beyond the first tie and inwardly beyond the second tie.

22. The cushion assembly of claim 20, wherein the first tie has opposing ends that are attached to the first support region of the elastomeric seal-forming portion and a middle portion between the opposing ends, the middle portion being separated from the elastomeric seal-forming portion so that gas in the plenum chamber is allowed to flow between the first tie and the elastomeric seal-forming portion.

23. The cushion assembly of claim 20, wherein the second tie has opposing ends that are attached to the second support region of the elastomeric seal-forming portion and a middle portion between the opposing ends, the middle portion being separated from the elastomeric seal-forming portion so that gas in the plenum chamber is allowed to flow between the second tie and the elastomeric seal-forming portion.

24. The cushion assembly of claim 20, wherein the first tie and the second tie are configured to be positioned alongside the patient's nose above the patient's nasal base in use.

25. The cushion assembly of claim 20, wherein the first tie and the second tie are elastomeric.

26. The cushion assembly of claim 15, wherein the blowout prevention system is attached to the elastomeric seal-forming portion at a region where the exterior surface of the elastomeric seal-forming portion is relatively less tacky than the tackiness in the inferior region, wherein a transition from the relatively tackier exterior surface of the elastomeric seal-forming portion to the relatively less tacky surface is located in the first support region, wherein a transition from the relatively tackier exterior surface of the elastomeric seal-forming portion to the relatively less tacky surface is located in the second support region, wherein a transition from the relatively tackier exterior surface of the elastomeric seal-forming portion to the relatively less tacky surface is located at the unsupported edge of the elastomeric seal-forming portion, wherein the blowout prevention system comprises a first tie anchored to the elastomeric seal-forming portion at the first support region and a second tie anchored to the elastomeric seal-forming portion at the second support region, wherein the unsupported edge of the elastomeric seal-forming portion extends inwardly beyond the first tie and inwardly beyond the second tie, wherein the first tie has opposing ends that are attached to the first support region of the elastomeric seal-forming portion and a middle portion between the opposing ends, the middle portion being separated from the elastomeric seal-forming portion so that gas in the plenum chamber is allowed to flow between the first tie and the elastomeric seal-forming portion, wherein the second tie has opposing ends that are attached to the second support region of the elastomeric seal-forming portion and a middle portion between the opposing ends, the middle portion being separated from the elastomeric seal-forming portion so that gas in the plenum chamber is allowed to flow between the second tie and the elastomeric seal-forming portion, wherein the first tie and the second tie are configured to be positioned alongside the patient's nose above the patient's nasal base in use, and wherein the first tie and the second tie are elastomeric.

27. A patient interface comprising:
the cushion assembly of claim 15;
a rigid shell removably connected to the cushion assembly; and
headgear removably attached to the rigid shell.

28. A CPAP system comprising:
the patient interface according to claim 27;
a flow generator configured to pressurize a flow of gas; and
an air delivery tube configured to deliver the pressurized gas to the patient interface.

\* \* \* \* \*